(12) United States Patent
Bethiel et al.

(10) Patent No.: US 7,348,335 B2
(45) Date of Patent: *Mar. 25, 2008

(54) COMPOSITIONS USEFUL AS INHIBITORS OF JAK AND OTHER PROTEIN KINASES

(75) Inventors: Randy S. Bethiel, Lexington, MA (US); Young-Choon Moon, Belle Mead, NJ (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 249 days.

This patent is subject to a terminal disclaimer.

(21) Appl. No.: 10/702,113

(22) Filed: Nov. 5, 2003

(65) Prior Publication Data

US 2004/0176271 A1 Sep. 9, 2004

Related U.S. Application Data

(60) Provisional application No. 60/424,043, filed on Nov. 5, 2002.

(51) Int. Cl.
| | | |
|---|---|---|
| C07D 239/42 | (2006.01) | |
| C07D 401/04 | (2006.01) | |
| C07D 403/04 | (2006.01) | |
| A61K 31/506 | (2006.01) | |
| A61P 11/06 | (2006.01) | |
| A61P 19/02 | (2006.01) | |
| A61P 25/26 | (2006.01) | |
| A61P 37/05 | (2006.01) | |
| A61P 11/00 | (2006.01) | |
| C07D 401/14 | (2006.01) | |
| C07D 403/14 | (2006.01) | |
| A61K 31/53 | (2006.01) | |
| A61K 31/501 | (2006.01) | |
| A61K 31/4427 | (2006.01) | |

(52) U.S. Cl. .................. 514/275; 544/330; 544/331; 544/180; 544/181; 544/238; 514/241; 514/242; 514/252.01

(58) Field of Classification Search ............... 544/330, 544/331; 514/275
See application file for complete search history.

(56) References Cited

U.S. PATENT DOCUMENTS

| 6,949,544 B2 | 9/2005 | Bethiel et al. ............ 514/235.8 |
| 2004/0147507 A1 | 7/2004 | Ledeboer et al. ....... 514/217.04 |

FOREIGN PATENT DOCUMENTS

| WO | WO 95/09847 | 4/1995 |
| WO | WO 95/09851 | 4/1995 |
| WO | WO 95/09853 | 4/1995 |
| WO | WO 97/19065 A1 | 5/1997 |
| WO | WO 99/65897 | 12/1999 |
| WO | WO 01/29009 A1 | 4/2001 |
| WO | WO-02/20495 A2 * | 3/2002 |
| WO | WO 02/22601 | 3/2002 |
| WO | WO 02/46170 | 6/2002 |
| WO | WO 02/46171 A2 | 6/2002 |
| WO | WO 02/079193 | 10/2002 |
| WO | WO 02/079197 | 10/2002 |
| WO | WO 03/030909 | 4/2003 |

OTHER PUBLICATIONS

Cecil Textbook of Medicine, edited by Bennet, J.C., and Plum F., 20th edition,vol. 1, 1004-1010, 1996.*
Duhe et al. Cell Biochem. Biophys. 34(1): 17-59, 2001.*
Rane et al., Oncogene 19(49): 5662-79, 2000.*
, Kim et al., Curr. Opin Genet Dev. 10(5): 508-514, 2000.*
Mass, R. D., Int. J. Radiation Oncology Bio. Phys.vol. 58(3): 932-940, 2004.*
Fabbro et al. Pharmacology & therapeutics 93, 79-98, 2002.*
Ivashkiv et al., Arthritis & Rheumatism 48(8)2092-2096, 2003.*
Changelian et al., "Prevention of organ allograft rejection by a specific janus kinase 3 inhibitor," Science, 302:875-878, (2003).
Malaviya et al., "Treatment of allergic asthma be targeting janus kinase 3-dependent leukotriene synthesis in mast cells with 4-(3',5'—dibromo-4'-hydroxyphenyl)amino-6,7-dimethoxyquinazoline (WHI-P97)," The Journal of Pharmacology and Experimental Therapeutics, 295(3):912-926, (2000).
Trieu et al., "A specific inhibitor of janus kinase-3 increases survival in a transgenic mouse model of amyotrophic lateral sclerosis," Biochemical and Biophysical Research Communications, 267:22-25, (2000).

* cited by examiner

Primary Examiner—Venkataraman Balasubramanian
(74) Attorney, Agent, or Firm—Karen E. Brown

(57) ABSTRACT

The present invention provides a compound of formula I:

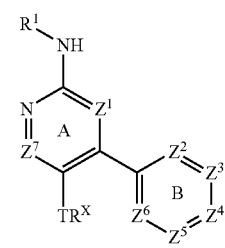

or a pharmaceutically acceptable salt thereof. The invention also provides pharmaceutically acceptable compositions comprising the compounds of the invention and methods of utilizing those compounds and compositions in the treatment of various protein kinase mediated disorders.

19 Claims, No Drawings

COMPOSITIONS USEFUL AS INHIBITORS OF JAK AND OTHER PROTEIN KINASES

CROSS-REFERENCE TO RELATED APPLICATIONS

The present application claims priority under 35 U.S.C. § 119(e) to U.S. Provisional Application No. 60/424,043, filed Nov. 5, 2002, entitled "Compositions Useful as Inhibitors of Jak and Other Protein Kinases, the entire contents of which is hereby incorporated by reference.

TECHNICAL FIELD OF INVENTION

The present invention relates to compounds useful as inhibitors of protein kinases. The invention also provides pharmaceutically acceptable compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents.

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [Frank *Mol. Med.* 5, 432-456 (1999) & Seidel, et al, *Oncogene* 19, 2645-2656 (2000)].

JAK1, JAK2, and TYK2 are ubiquitously expressed, while JAK3 is predominantly expressed in hematopoietic cells. JAK3 binds exclusively to the common cytokine receptor gamma chain ($\gamma_c$) and is activated by IL-2, IL-4, IL-7, IL-9, and IL-15. The proliferation and survival of murine mast cells induced by IL-4 and IL-9 have, in fact, been shown to be dependent on JAK3- and $\gamma_c$-signaling [Suzuki et al, *Blood* 96, 2172-2180 (2000)].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al, *Nature* 346, 274-276 (1990) & Galli, *N. Engl. J. Med.*, 328, 257-265 (1993)]. A crucial role for JAK3 in IgE receptor-mediated mast cell responses in vitro and in vivo has been established [Malaviya, et al, *Biochem. Biophys. Res. Commun.* 257, 807-813 (1999)]. In addition, the prevention of type I hypersensitivity reactions, including anaphylaxis, mediated by mast cell-activation through inhibition of JAK3 has also been reported [Malaviya et al, *J. Biol. Chem.* 274,27028-27038 (1999)]. Targeting mast cells with JAK3 inhibitors modulated mast cell degranulation in vitro and prevented IgE receptor/antigen-mediated anaphylactic reactions in vivo.

A recent study described the successful targeting of JAK3 for immune suppression and allograft acceptance. The study demonstrated a dose-dependent survival of Buffalo heart allograft in Wistar Furth recipients upon administration of inhibitors of JAK3 indicating the possibility of regulating unwanted immune responses in graft versus host disease [Kirken, *Transpl. Proc.* 33, 3268-3270 (2001)].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demostrated that IL-4-mediated activation of IL-4/STAT pathway is mediated through the Janus Kinases (JAK 1 & 3) and that IL-4-associated JAK kinases are expressed in the RA synovium [Muller-Ladner, et al, *J. Immunol.* 164, 3894-3901 (2000)].

Familial amyotrophic lateral sclerosis (FALS) is a fatal neurodegenerative disorder affecting about 10% of ALS patients. The survival rates of FALS mice were increased upon treatment with a JAK3 specific inhibitor. This suggested that JAK3 plays a role in FALS [Trieu, et al, *Biochem. Biophys. Res. Commun.* 267, 22-25 (2000)].

Signal transducer and activator of transcription (STAT) proteins are activated by, among others, the JAK family kinases. Results form a recent study suggested the possibility of intervention in the JAK/STAT signaling pathway by targeting JAK family kinases with specific inhibitors for the treatment of leukemia [Sudbeck, et al, *Clin. Cancer Res.* 5, 1569-1582 (1999)]. JAK3 specific compounds were shown to inhibit the clonogenic growth of JAK3-expressing cell lines DAUDI, RAMOS, LC1;19, NALM-6, MOLT-3 and HL-60.

In animal models, TEL/JAK2 fusion proteins have induced myeloproliferative disorders and in hematopoietic cell lines, introduction of TEL/JAK2 resulted in activation of STAT1, STAT3, STAT5, and cytokine-independent growth [Schwaller, et al, *EMBO J.* 17, 5321-5333 (1998)].

Inhibition of JAK 3 and TYK 2 abrogated tyrosine phosphorylation of STAT3, and inhibited cell growth of mycosis fungoides, a form of cutaneous T cell lymphoma. These results implicated JAK family kinases in the constitutively activated JAK/STAT pathway that is present in mycosis fungoides [Nielsen, et al, Proc. *Nat. Acad. Sci. U.S.A.* 94, 6764-6769 (1997)]. Similarly, STAT3, STAT5, JAK1 and JAK2 were demonstrated to be constitutively activated in mouse T cell lymphoma characterized initially by LCK over-expression, thus further implicating the JAK/STAT pathway in abnormal cell growth [Yu, et al, *J. Immunol.* 159, 5206-5210 (1997)]. In addition, IL-6-mediated STAT3 activation was blocked by an inhibitor of JAK, leading to sensitization of myeloma cells to apoptosis [Catlett-Falcone, et al, *Immunity*10, 105-115 (1999)].

Glycogen synthase kinase-3 (GSK-3) is a serine/threonine protein kinase comprised of $\alpha$ and $\beta$ isoforms that are each encoded by distinct genes [Coghlan et al., *Chemistry & Biology*, 7, 793-803 (2000); Kim and Kimmel, *Curr. Opinion Genetics Dev.*, 10, 508-514 (2000)]. GSK-3 has been implicated in various diseases including diabetes, Alzheimer's disease, CNS disorders such as manic depressive disorder and neurodegenerative diseases, and cardiomyocete hypertrophy [WO 99/65897; WO 00/38675; and Haq et al., *J. Cell Biol.* (2000) 151, 117]. These diseases may be caused by, or result in, the abnormal operation of certain cell signaling pathways in which GSK-3 plays a role. GSK-3 has been found to phosphorylate and modulate the activity of a number of regulatory proteins. These include glycogen synthase which is the rate limiting enzyme necessary for glycogen synthesis, the microtubule associated protein Tau, the gene transcription factor $\beta$-catenin, the translation initiation factor e1F2B, as well as ATP citrate lyase, axin, heat shock factor-1, c-Jun, c-Myc, c-Myb, CREB, and CEPB$\alpha$. These diverse targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS*, 93, 8455-9 (1996); Cross et al., *Biochem. J.*, 303, 21-26 (1994); Cohen, *Biochem. Soc. Trans.*, 21, 555-567 (1993); Massillon et al., *Biochem J.* 299, 123-128 (1994)]. However, in a diabetic patient where the insulin response is impaired, glycogen synthesis and glucose uptake fail to increase despite the presence of relatively high blood levels of insulin. This leads to abnormally high blood levels of glucose with acute and long term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [WO 00/38675]. Therapeutic inhibitors of GSK-3 are therefore potentially useful for treating diabetic patients suffering from an impaired response to insulin.

GSK-3 activity has also been associated with Alzheimer's disease. This disease is characterized by the well-known $\beta$-amyloid peptide and the formation of intracellular neurofibrillary tangles. The neurofibrillary tangles contain hyperphosphorylated Tau protein where Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., *Current Biology* 4, 1077-86 (1994); Brownlees et al., *Neuroreport* 8, 3251-55 (1997)]. Therefore, it is believed that GSK-3 activity may promote generation of the neurofibrillary tangles and the progression of Alzheimer's disease.

Another substrate of GSK-3 is $\beta$-catenin which is degradated after phosphorylation by GSK-3. Reduced levels of $\beta$-catenin have been reported in schizophrenic patients and have also been associated with other diseases related to increase in neuronal cell death [Zhong et al., *Nature*, 395, 698-702 (1998); Takashima et al., *PNAS*, 90, 7789-93 (1993); Pei et al., *J. Neuropathol. Exp*, 56, 70-78 (1997)].

Syk is a tyrosine kinase that plays a critical role in Fc$\epsilon$RI mediated mast cell degranulation and eosiniphil activation. Accordingly, Syk kinase is implicated in various allergic disorders, in particular asthma. It has been shown that that Syk binds to the phosphorylated gamma chain of the Fc$\epsilon$RI receptor via N-terminal SH2 domains and is essential for downstream signaling [Taylor et al, Mol Cell Biol 1995; 15:4149.

Inhibition of eosinophil apoptosis has been proposed as key mechanisms for the development of blood and tissue eosinophilia in asthma. IL-5 and GM-CSF are upregulated in asthma and are proposed to cause blood and tissue eosinophilia by inhibition of eosinophil apoptosis. Inhibition of eosinophil apoptosis has been proposed as a key mechanism for the development of blood and tissue eosinophilia in asthma. It has been reported that Syk kinase is required for the prevention of eosinophil apoptosis by cytokines (using antisense)[Yousefi et al, J Exp Med 1996; 183: 1407].

The role of Syk in Fc$\gamma$R dependent and independent response in bone marrow derived macrophages has been determined by using irradiated mouse chimeras reconstituted with fetal liver cells from Syk-/-embryos. Syk deficient macrophages were defective in phagocytosis induced by Fc$\gamma$R but showed normal phagocytosis in response to complement [Kiefer et al, Mol Cell Biol 1998; 18:4209]. It has also been reported that aerosolized Syk antisense suppresses Syk expression and mediator release from macrophages [Stenton et al, J Immunology 2000; 164: 3790].

Cyclin-dependent kinases (CDKs) are serine/threonine protein kinases consisting of a $\beta$-sheet rich amino-terminal lobe and a larger carboxy-terminal lobe which is largely $\alpha$-helical. The CDKs display the 11 subdomains shared by all protein kinases and range in molecular mass from 33 to 44 kD. This family of kinases, which includes CDK1, CKD2, CDK4, and CDK6, requires phosphorylation at the residue corresponding to CDK2 Thr160 in order to be fully active [Meijer, L., *Drug Resistance Updates*, 3, 83-88 (2000)].

Each CDK complex is formed from a regulatory cyclin subunit (e.g., cyclin A, B1, B2, D1, D2, D3, and E) and a catalytic kinase subunit (e.g., CDK1, CDK2, CDK4, CDK5, and CDK6). Each different kinase/cyclin pair functions to regulate the different and specific phases of the cell cycle known as the G1, S, G2, and M phases [Nigg, E., *Nature Reviews*, 2, 21-32 (2001); Flatt, P., Pietenpol, J., *Drug Metabolism Reviews*, 32, 283-305 (2000)].

The CDKs have been implicated in cell proliferation disorders, particularly in cancer. Cell proliferation is a result of the direct or indirect deregulation of the cell division cycle and the CDKs play a critical role in the regulation of the various phases of this cycle. For example, the overexpression of cyclin D1 is commonly associated with numerous human cancers including breast, colon, hepatocellular carcinomas and gliomas [Flatt, P., Pietenpol, J., *Drug Metabolism Reviews*, 32, 283-305 (2000)]. The CDK2/cyclin E complex plays a key role in the progression from the early $G_1$ to S phases of the cell cycle and the overexpression of cyclin E has been associated with various solid tumors. Therefore, inhibitors of cyclins D1, E, or their associated CDKs are useful targets for cancer therapy [Kaubisch, A., Schwartz, G., *The Cancer Journal*, 6, 192-212 (2000)].

CDKs, especially CDK2, also play a role in apoptosis and T-cell development. CDK2 has been identified as a key regulator of thymocyte apoptosis [Williams, O., et al, *European Journal of Immunology*, 709-713 (2000)]. Stimulation of CDK2 kinase activity is associated with the progression of apoptosis in thymocytes, in response to specific stimuli. Inhibition of CDK2 kinase activity blocks this apoptosis resulting in the protection of thymocytes.

In addition to regulating the cell cycle and apoptosis, the CDKs are directly involved in the process of transcription. Numerous viruses require CDKs for their replication process. Examples where CDK inhibitors restrain viral replication include human cytomegakovirus, herpes virus, and varicella-zoster virus [Meijer, L., *Drug Resistance Updates*, 3, 83-88 (2000)].

Inhibition of CDK is also useful for the treatment of neurodegenerative disorders such as Alzheimer's disease. The appearance of Paired Helical Filaments (PHF), associated with Alzheimer's disease, is caused by the hyperphosphorylation of Tau protein by CDK5/p25 [Meijer, L., *Drug Resistance Updates*, 3, 83-88 (2000)].

JNK is a member of the mitogen-activated protein (MAP) kinase family. MAP kinases (MAPKs) are activated by a variety of signals including growth factors, cytokines, UV radiation, and stress-inducing agents. MAPKs are serine/threonine kinases and their activation occur by dual phosphorylation of threonine and tyrosine at the Thr-X-Tyr segment in the activation loop. MAPKs phosphorylate various substrates including transcription factors, which in turn regulate the expression of specific sets of genes and thus mediate a specific response to the stimulus.

Three distinct genes, JNK1, JNK2, JNK3 have been identified for this kinase family and at least ten different splicing isoforms of JNKs exist in mammalian cells [Gupta et al., *EMBO J.*, 15, 2760-70 (1996)]. Members of the JNK family are activated by proinflammatory cytokines, such as tumor necrosis factor-α (TNFα) and interleukin-1 β (IL-1β), as well as by environmental stress, including anisomycin, UV irradiation, hypoxia, and osmotic shock [Minden et al., *Biochemica et Biophysica Acta*, 1333, F85-F104 (1997)].

The down-stream substrates of JNKs include transcription factors c-Jun, ATF-2, Elk1, p53 and a cell death domain protein (DENN) [Zhang et al. *Proc. Natl. Acad. Sci. USA*, 95, 2586-91 (1998)]. Each JNK isoform binds to these substrates with different affinities, suggesting a regulation of signaling pathways by substrate specificity of different JNKs in vivo (Gupta et al., supra).

JNKs, along with other MAPKs, have been implicated in having a role in mediating cellular response to cancer, thrombin-induced platelet aggregation, immunodeficiency disorders, autoimmune diseases, cell death, allergies, osteoporosis and heart disease. The therapeutic targets related to activation of the JNK pathway include chronic myelogenous leukemia (CML), rheumatoid arthritis, asthma, osteoarthritis, ischemia, cancer and neurodegenerative diseases.

Several reports have detailed the importance of JNK activation associated with liver disease or episodes of hepatic ischemia [*Nat. Genet.* 21, 326-9 (1999); *FEBS Lett.* 420, 201-4 (1997); *J. Clin. Invest.* 102, 1942-50 (1998); *Hepatology* 28, 1022-30 (1998)]. Therefore, inhibitors of JNK may be useful to treat various hepatic disorders.

A role for JNK in cardiovascular disease such as myocardial infarction or congestive heart failure has also been reported as it has been shown JNK mediates hypertrophic responses to various forms of cardiac stress [*Circ. Res.* 83, 167-78 (1998); *Circulation* 97, 1731-7 (1998); *J. Biol. Chem.* 272, 28050-6 (1997); *Circ. Res.* 79, 162-73 (1996); *Circ. Res.* 78, 947-53 (1996); *J. Clin. Invest.* 97, 508-14 (1996)].

It has been demonstrated that the JNK cascade also plays a role in T-cell activation, including activation of the IL-2 promoter. Thus, inhibitors of JNK may have therapeutic value in altering pathologic immune responses [*J. Immunol.* 162, 3176-87 (1999); *Eur. J. Immunol.* 28, 3867-77 (1998); *J. Exp. Med.*186, 941-53 (1997); *Eur. J. Immunol.* 26, 989-94 (1996)].

A role for JNK activation in various cancers has also been established, suggesting the potential use of JNK inhibitors in cancer. For example, constitutively activated JNK is associated with HTLV-1 mediated tumorigenesis [*Oncogene* 13, 135-42 (1996)]. JNK may play a role in Kaposi's sarcoma (KS) because it is thought that the proliferative effects of βFGF and OSM on KS cells are mediated by their activation of the JNK signaling pathway [*J. Clin. Invest.* 99, 1798-804 (1997)]. Other proliferative effects of other cytokines implicated in KS proliferation, such as vascular endothelial growth factor (VEGF), IL-6 and TNFα, may also be mediated by JNK. In addition, regulation of the c-jun gene in p210 BCR-ABL transformed cells corresponds with activity of JNK, suggesting a role for JNK inhibitors in the treatment for chronic myelogenous leukemia (CML) [*Blood* 92, 2450-60 (1998)].

JNK1 and JNK2 are widely expressed in a variety of tissues. In contrast, JNK3, is selectively expressed in the brain and to a lesser extent in the heart and testis [Gupta et al., supra; Mohit et al., *Neuron* 14, 67-78 (1995); Martin et al., *Brain Res. Mol. Brain Res.* 35, 47-57 (1996)]. JNK3 has been linked to neuronal apoptosis induced by kainic acid, indicating a role of JNK in the pathogenesis of glutamate neurotoxicity. In the adult human brain, JNK3 expression is localized to a subpopulation of pyramidal neurons in the CA1, CA4 and subiculum regions of the hippocampus and layers 3 and 5 of the neocortex [Mohit et al., supra]. The CA1 neurons of patients with acute hypoxia showed strong nuclear JNK3-immunoreactivity compared to minimal, diffuse cytoplasmic staining of the hippocampal neurons from brain tissues of normal patients [Zhang et al., supra]. Thus, JNK3 appears to be involved involved in hypoxic and ischemic damage of CA1 neurons in the hippocampus.

In addition, JNK3 co-localizes immunochemically with neurons vulnerable in Alzheimer's disease [Mohit et al., supra]. Disruption of the JNK3 gene caused resistance of mice to the excitotoxic glutamate receptor agonist kainic acid, including the effects on seizure activity, AP-1 transcriptional activity and apoptosis of hippocampal neurons, indicating that the JNK3 signaling pathway is a critical component in the pathogenesis of glutamate neurotoxicity (Yang et al., *Nature*, 389, 865-870 (1997)].

Based on these findings, JNK signalling, especially that of JNK3, has been implicated in the areas of apoptosis-driven neurodegenerative diseases such as Alzheimer's Disease, Parkinson's Disease, ALS (Amyotrophic Lateral Sclerosis), epilepsy and seizures, Huntington's Disease, traumatic brain injuries, as well as ischemic and hemorrhaging stroke.

Accordingly, there is a great need to develop inhibitors of JAK, JNK, GSK, SYK, and CDK protein kinases that are useful in treating various diseases or conditions associated with JAK, JNK, GSK, SYK, and CDK activation, particularly given the inadequate treatments currently available for the majority of these disorders.

SUMMARY OF THE INVENTION

It has now been found that compounds of this invention, and pharmaceutically acceptable compositions thereof, are effective as inhibitors of JAK, JNK, GSK, SYK, and CDK protein kinases. In certain embodiments, these compounds are effective as inhibitors of JAK-3, JNK-3, GSK-3, SYK, and CDK-2 protein kinases. These compounds have the general formula I:

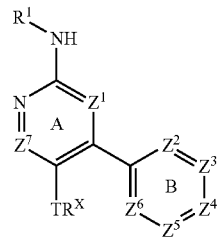

or a pharmaceutically acceptable derivative thereof, wherein $R^1$, T, $R^X$, $Z^1$, $Z^2$, $Z^3$, $Z^4$, $Z^5$, $Z^6$, and $Z^7$ are as defined below.

These compounds and pharmaceutical compositions thereof are useful for treating or preventing a variety of disorders, such as heart disease, diabetes, Alzheimer's disease, immunodeficiency disorders, inflammatory diseases, allergic diseases, autoimmune diseases, destructive bone disorders such as osteoporosis, proliferative disorders, infectious diseases, immunologically-mediated diseases, and viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. The compositions are especially useful for disorders such as chronic myelogenous leukemia (CML), rheumatoid arthritis, asthma, osteoarthritis, ischemia, cancer, liver disease including hepatic ischemia, heart disease such as myocardial infarction and congestive heart failure, pathologic immune conditions involving T cell activation, and neurodegenerative disorders.

DETAILED DESCRIPTION OF THE INVENTION

1. General Description of Compounds of the Invention

The present invention relates to a compound of formula I:

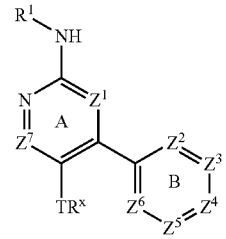

or a pharmaceutically acceptable salt thereof, wherein:
  $R^1$ is Q-$Ar^1$,
    wherein Q is a bond or is a $C_{1-2}$ alkylidene chain wherein one methylene unit of Q is optionally replaced by O, NR, NRCO, NRCONR, NRCO$_2$, CO, CO$_2$, CONR, OCONR, SO$_2$, SO$_2$NR, NRSO$_2$, NRSO$_2$NR, COCO, or COCH$_2$CO;
  $Ar^1$ is a 5-7 membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $Ar^1$ is optionally substituted with q independent occurrences of Z-$R^Z$; wherein q is 0-5, Z is a bond or is a $C_1$-$C_6$ alkylidene chain wherein up to two methylene units of Z are optionally and independently replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of $R^Z$ is independently selected from R', halogen, NO$_2$, CN, OR', SR', N(R')$_2$, NR'COR', NR'CON(R')$_2$, NR°CO$_2$R', COR', CO$_2$R', OCOR', CON(R')$_2$, OCON(R')$_2$, SOR', SO$_2$R', SO$_2$N(R')$_2$, NR'SO$_2$R', NR'SO$_2$N(R')$_2$, COCOR', or COCH$_2$COR';
  each occurrence of R is independently hydrogen or an optionally substituted $C_{1-6}$ aliphatic group; and each occurrence of R' is independently hydrogen or an optionally substituted $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;
  $Z^1$ is N or CH;
  $Z^7$ is N or C—$UR^Y$;
  T and U are each independently a bond or a saturated or unsaturated $C_{1-6}$ alkylidene chain, wherein up to two methylene units of the chain are optionally and independently replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR;

$R^X$ and $R^Y$ are each independently halogen, CN, $NO_2$, or R';

$Z^2$, $Z^5$ and $Z^6$ are each independently N or CH, provided that no more than two of $Z^2$, $Z^5$, and $Z^6$ are N;

$Z^3$ is $CR^3$;

$Z^4$ is $CR^4$;

wherein one of $R^3$ or $R^4$ is $R^U$, and the other of $R^3$ or $R^4$ is $R^{V1}$, wherein: $R^U$ is $(CH_2)_tCN$, $(CH_2)_tNO_2$, $(CH_2)_tN(R)_2$, $(CH_2)_tNRC(O)R$, $(CH_2)_tCON(R)_2$, $(CH_2)_tCOOR$, $(CH_2)_tSO_2N(R)_2$, $(CH_2)_tNRSO_2R$, $(CH_2)_tNRCON(R)_2$, $(CH_2)_tNRSO_2N(R)_2$, $(CH_2)_tCOCOR$, $(CH_2)_tAr^2$, wherein t is 0, 1, or 2, and $Ar^2$ is an optionally substituted 5-7 membered saturated, partially unsaturated, or fully unsaturated monocyclic ring having 0-3 heteroatoms independently selected from nitrogen, oxygen, or sulfur; and $R^{V1}$ is OR'.

In certain embodiments, for compounds of general formula I:

a) when $Z^1$ is N, and $Z^7$ is CH; then $R^1$ is not phenyl only substituted with two or three occurrences of OR';

b) when $Z^1$ is N, $Z^7$ is CH; and ring B is phenyl, then $R^1$ is not phenyl substituted in the meta position with nitro, fluorine-substituted lower alkoxy, or —NRCOOR', $NRCON(R')_2$, NRCSOR', or $NRCSN(R')_2$; and c) when $Z^1$ is N, $Z^7$ is CH, and ring B is pyridyl, pyrazinyl, pyrimidinyl, or pyridazinyl substituted with one or more occurrences of halogen, cyano, carbamoyl, COOR, COR, $SO_2N(R)_2$, $N(R)_2$, OR, or fluorine substituted lower alkyl, then $R^1$ is not phenyl substituted in the meta position with halogen, cyano, carbamoyl, COOR, COR, $SO_2N(R)_2$, $N(R)_2$, OR, or fluorine substituted lower alkyl.

In yet other embodiments, for the compounds of formula I described generally above, those compounds where $TR^x$ is halogen are excluded.

In still other embodiments, for the compounds of formula I described generally above, those compounds where $TR^x$ is cyano are excluded.

In certain other embodiments, for the compounds of formula I described generally above, those compounds where $TR_x$ is alkynyl are excluded.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention.

It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means nonaromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise defined above and herein, suitable substituents on the unsaturated carbon atom of an aryl or heteroaryl group are generally selected from halogen; —$R°$; —$OR°$; —$SR°$; phenyl (Ph) optionally substituted with $R°$; —$O(Ph)$ optionally substituted with $R°$; —$(CH_2)_{1-2}(Ph)$, optionally substituted with $R°$; —$CH=CH(Ph)$, optionally substituted with $R°$; —$NO_2$; —$CN$; —$N(R°)_2$; —$NR°C(O)R°$; —$NR°C(S)R°$; —$NR°C(O)N(R°)_2$; —$NR°C(S)N(R°)_2$; —$NR°CO_2R°$; —$NR°NR°C(O)R°$; —$NR°NR°C(O)N(R°)_2$; —$NR°NR°CO_2R°$; —$C(O)C(O)R°$; —$C(O)CH_2C(O)R°$; —$CO_2R°$; —$C(O)R°$; —$C(S)R°$; —$C(O)N(R°)_2$; —$C(S)N(R°)_2$; —$OC(O)N(R°)_2$; —$OC(O)R°$; —$C(O)N(OR°)R°$; —$C(NOR°)R°$; —$S(O)_2R°$; —$S(O)_3R°$; —$SO_2N(R°)_2$; —$S(O)R°$; —$NR°SO_2N(R°)_2$; —$NR°SO_2R°$; —$N(OR°)R°$; —$C(=NH)—N(R°)_2$; —$P(O)_2R°$; —$PO(R°)_2$; —$OPO(R°)_2$; —$(CH_2)_{0-2}NHC(O)R°$; phenyl (Ph) optionally substituted with $R°$; —$O(Ph)$ optionally substituted with $R°$; —$(CH_2)_{1-2}(Ph)$, optionally substituted with $R°$; or —$CH=CH(Ph)$, optionally substituted with $R°$; wherein each independent occurrence of $R°$ is selected from hydrogen, optionally substituted $C_{1-6}$ aliphatic, an unsubstituted 5-6 membered heteroaryl or heterocyclic ring, phenyl, —$O(Ph)$, or —$CH_2(Ph)$, or, notwithstanding the definition above, two independent occurrences of $R°$, on the same substituent or different substituents, taken together with the atom(s) to which each $R°$ group is bound, to form an optionally substituted 3-12 membered saturated, partially unsaturated, or fully unsaturated, or fully unsaturated monocyclic or bicyclic ring having 0-4 heteroatoms independently selected from nitrogen, oxygen, or sulfur.

Optional substituents on the aliphatic group of $R°$ are selected from $NH_2$, $NH(C_{1-4}aliphatic)$, $N(C_{1-4}aliphatic)_2$, halogen, $C_{1-4}aliphatic$, $OH$, $O(C_{1-4}aliphatic)$, $NO_2$, $CN$, $CO_2H$, $CO_2(C_{1-4}aliphatic)$, $O(haloC_{1-4}$ aliphatic), or $haloC_{1-4}$ aliphatic, wherein each of the foregoing $C_{1-4}$aliphatic groups of $R°$ is unsubstituted.

An aliphatic or heteroaliphatic group, or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =$NN(R^*)_2$, =NNHC(O)R*, =$NNHCO_2$(alkyl), =$NNHSO_2$(alkyl), or =NR*, where each R* is independently selected from hydrogen or an optionally substituted $C_{1-6}$ aliphatic group.

Unless otherwise defined above and herein, optional substituents on the nitrogen of a non-aromatic heterocyclic ring are generally selected from —$R^+$, —$N(R^+)_2$, —$C(O)R^+$, —$CO_2R^+$, —$C(O)C(O)R^+$, —$C(O)CH_2C(O)R^+$, —$SO_2R^+$, —$SO_2N(R^+)_2$, —$C(=S)N(R^{+1})_2$, —$C(=NH)—N(R^+)_2$, or —$NR^+SO_2R^+$; wherein $R^+$ is hydrogen, an optionally substituted $C_{1-6}$ aliphatic, optionally substituted phenyl, optionally substituted —$O(Ph)$, optionally substituted —$CH_2(Ph)$, optionally substituted —$(CH_2)_{1-2}(Ph)$; optionally substituted —$CH=CH(Ph)$; or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group or the phenyl ring of $R^+$ are selected from —$NH_2$, —$NH(C_{1-4}$ aliphatic), —$N(C_{1-4}$ aliphatic$)_2$, halogen, $C_{1-4}$ aliphatic, —$OH$, —$O(C_{1-4}$ aliphatic), —$NO_2$, —$CN$, —$CO_2H$, —$CO_2(C_{1-4}$ aliphatic), —$O$(halo $C_{1-4}$ aliphatic), or halo($C_{1-4}$ aliphatic), wherein each of the foregoing $C_{1-4}$aliphatic groups of $R^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of $R°$ (or $R^+$, R, R' or any other variable similarly defined herein), are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

Exemplary rings that are formed when two independent occurrences of $R°$ (or $R^+$, R, R' or any other variable similarly defined herein), are taken together with the atom(s) to which each variable is bound include, but are not limited to the following: a) two independent occurrences of $R°$ (or R+, R, R' or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R+, R, R' or any other variable similarly defined herein) that are bound to different atoms and are taken together with both of those atoms to form a ring, for example where a phenyl group is substituted with two occurrences of OR°

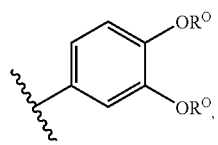

these two occurrences of R° are taken together with the oxygen atoms to which they are bound to form a fused 6-membered oxygen containing ring:

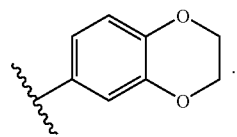

It will be appreciated that a variety of other rings can be formed when two independent occurrences of R° (or R+, R, R' or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

3. Description of Exemplary Compounds

In certain exemplary embodiments, $Z^1$ is N and amino pyrimidines of general formula II are provided:

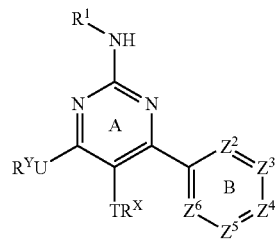

II wherein $R^1$, UR$^Y$, TR$^X$, $Z^2$, $Z^3$, $Z^4$, $Z^5$, and $Z^6$ are as defined generally above and in classes and subclasses herein.

In certain other exemplary embodiments, $Z^1$ is CH and amino pyridines of general formula III are provided:

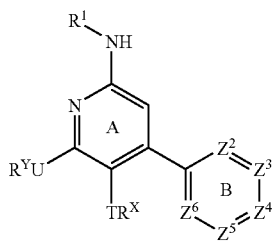

III wherein $R^1$, UR$^Y$, TR$^X$, $Z^2$, $Z^3$, $Z^4$, $Z^5$, and $Z^6$ are as defined generally above and in classes and subclasses herein.

As described generally above, $R^1$ is Q-Ar$^1$. Certain exemplary substituents for $R^1$ include optionally substituted group selected from phenyl, cyclohexyl, cyclopentyl, pyridyl, naphthyl, morpholino, piperazinyl, or piperidinyl. In other embodiments, $R^1$ is an optionally substituted group selected from phenyl, cyclohexyl, or pyridyl. In still other embodiments, $R^1$ is optionally substituted phenyl.

As described generally above, in certain embodiments, Ar$^1$ is substituted with 0-5 occurrences of ZR$^Z$. Exemplary ZR$^Z$ groups are selected from halogen, R', CN, NO$_2$, —N(R)(R'), —OR', —SR', —S(O)$_2$N(R)(R'), CO(C$_{1-4}$alkyl), —NRSO$_2$R', COO(C$_{1-4}$alkyl). In other embodiments, q is 1 or 2 and ZR$^Z$ is F, Cl, Br, COO(C$_{1-4}$alkyl), C$_{1-4}$alkyl, CN, NO$_2$, —NH$_2$, —OH, C$_{1-4}$alkoxy, —S(O)$_2$NH$_2$, or an optionally substituted benzyloxy, phenyloxy, or phenyl group. In yet other embodiments, q is 1, and ZR$^Z$ is in the meta or para position and ZR$^Z$ is F, Cl, Br, methyl, ethyl, benzyloxy, phenyl, phenyloxy, COO(C$_{1-4}$alkyl), —NH$_2$, —OH, C$_{1-4}$alkoxy, or —S(O)$_2$NH$_2$.

Exemplary TR$^X$ and UR$^Y$ groups of formula I, and classes and subclasses thereof as described herein, are each independently hydrogen, halogen, NO$_2$, CN, OR, SR or N(R)$_2$, or C$_{1-4}$aliphatic optionally substituted with oxo, OR, SR, N(R)$_2$, halogen, NO$_2$ or CN. In other embodiments, TR$^X$ and UR$^Y$ are each independently hydrogen, Me, OH, OMe or N(R)$_2$. In yet other embodiments, TR$^X$ and UR$^Y$ are each hydrogen.

In certain other embodiments, ring B is selected from one of the rings i-viii depicted below.

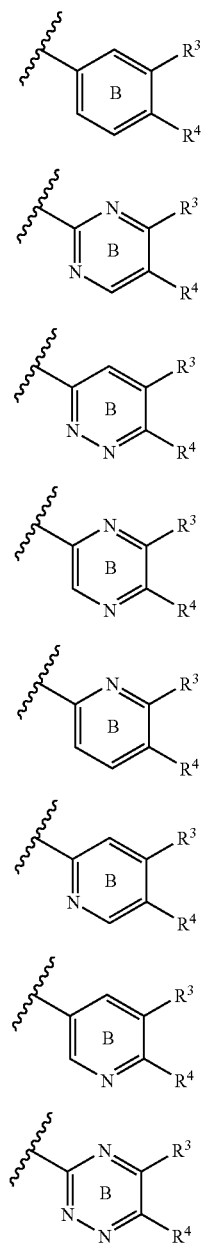

thiadiazole, oxadiazole or pyridyl group. In certain exemplary embodiments, compounds have one of the structures depicted below:

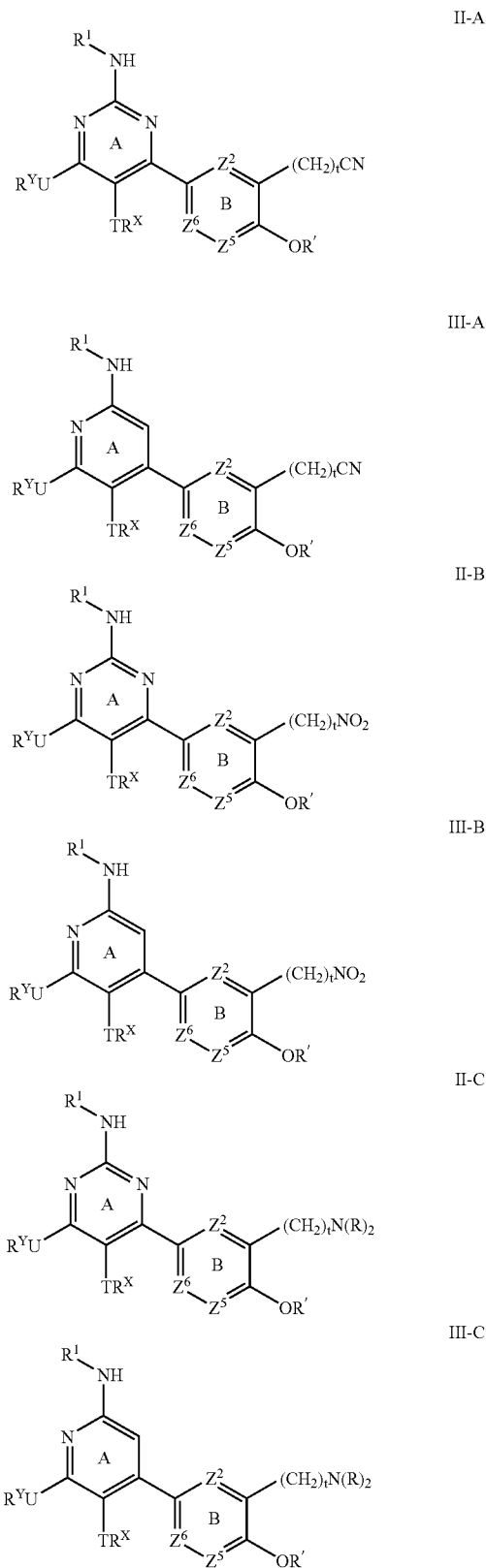

In still other embodiments, ring B is i, ii, v, vi, or vii. In yet other embodiments, ring B is i.

As described generally above, one of $R^3$ or $R^4$ is $R^U$, and the other of $R^3$ or $R^4$ is $R^{V1}$, wherein $R^U$ is $(CH_2)_tCN$, $(CH_2)_tNO_2$, $(CH_2)_tN(R)_2$, $(CH_2)_tNRC(O)R$, $(CH_2)_tCON(R)_2$, $(CH_2)_tCOOR$, $(CH_2)_tSO_2N(R)_2$, $(CH_2)_tNRSO_2R$, $(CH_2)_tNRCON(R)_2$, $(CH_2)_tNRSO_2N(R)_2$, $(CH_2)_tCOCOR$, $(CH_2)_tAr^2$, wherein t is 0, 1, or 2, and $Ar^2$ is an optionally substituted 5-7 membered saturated, partially unsaturated, or fully unsaturated monocyclic ring having 0-3 heteroatoms independently selected from nitrogen, oxygen, or sulfur; and $R^{V1}$ is OR'. In certain exemplary embodiments $Ar^2$ is an optionally substituted tetrazole, triazole, oxazole, thiazole, -continued
II-D
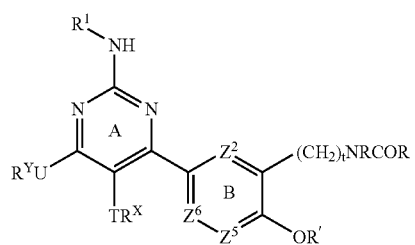
III-D
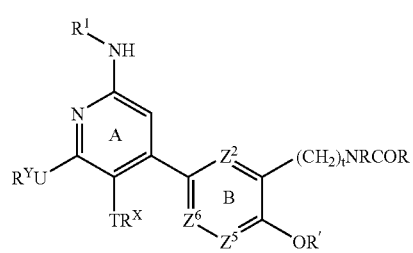
II-E
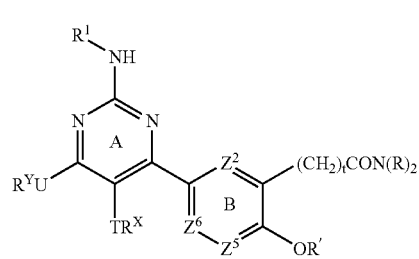
III-E
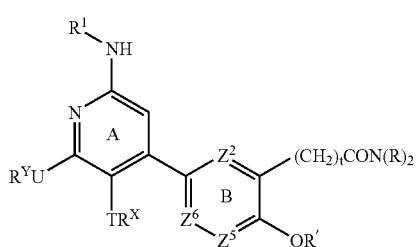
II-F
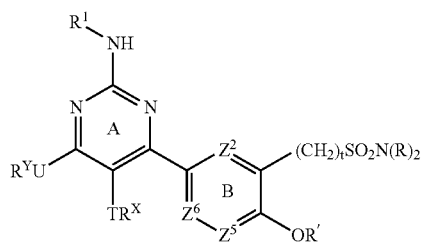
III-F
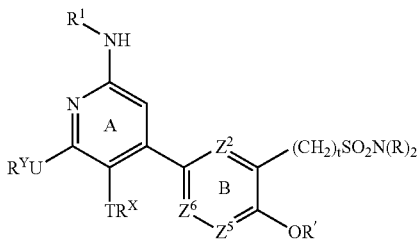
-continued
II-G
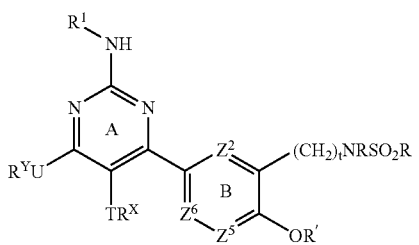
III-G
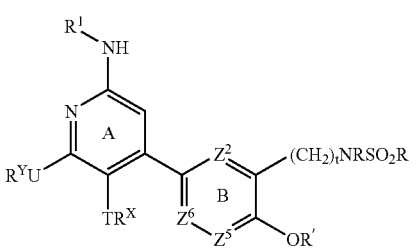
II-H
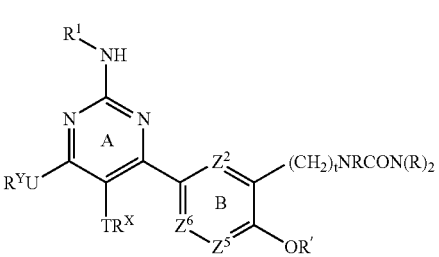
III-H
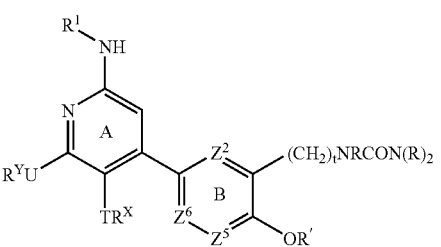
II-I
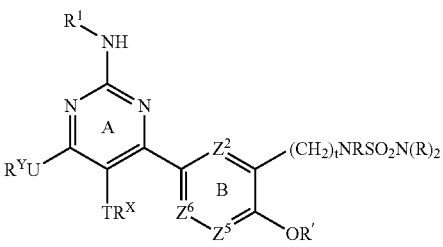
III-I
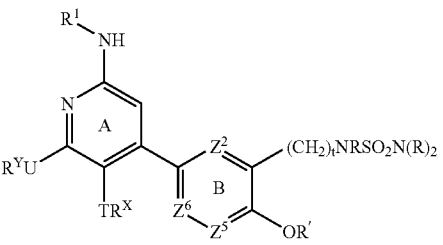

-continued
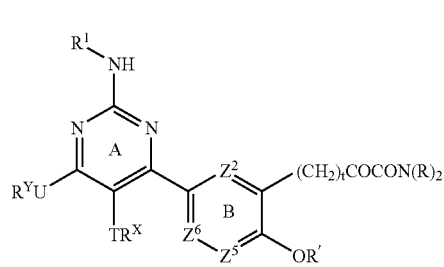
II-J
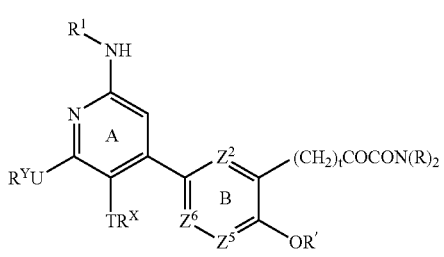
III-J
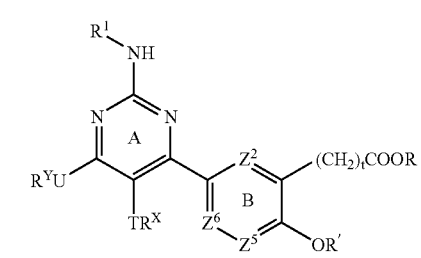
II-K
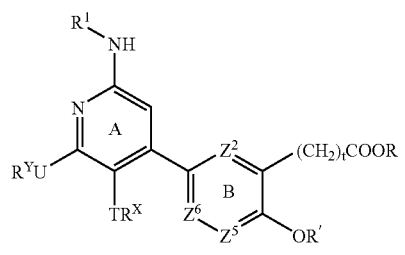
III-K
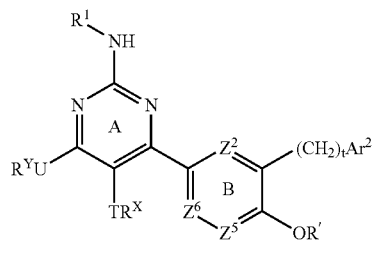
II-L
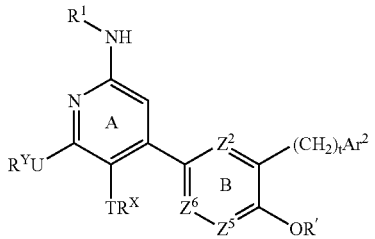
III-L
-continued
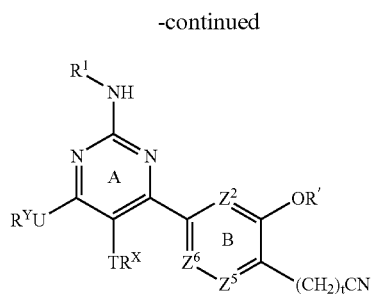
II-M
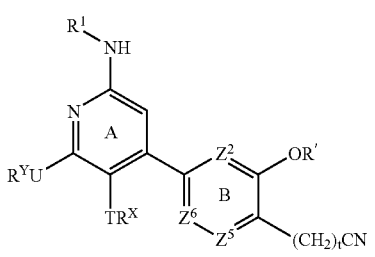
III-M
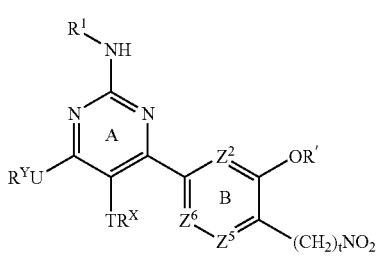
II-N
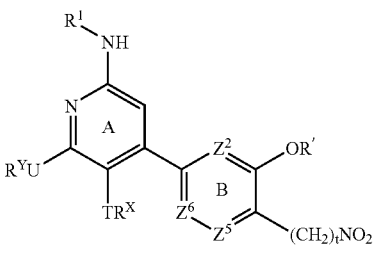
III-N
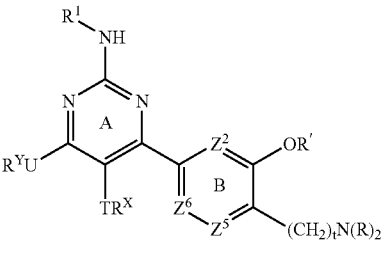
II-O
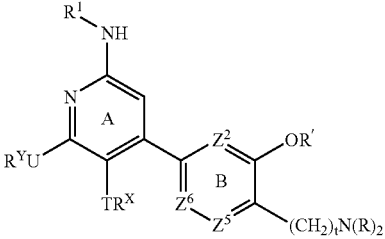
III-O -continued
II-P
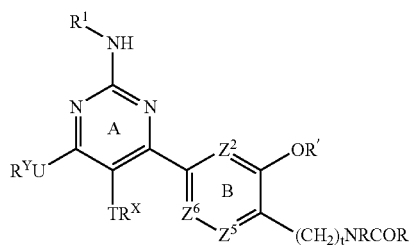
III-P
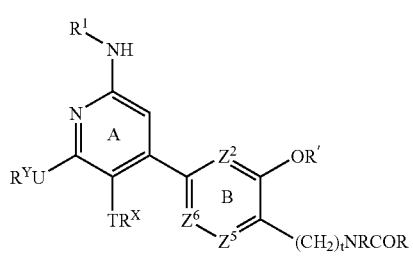
II-Q
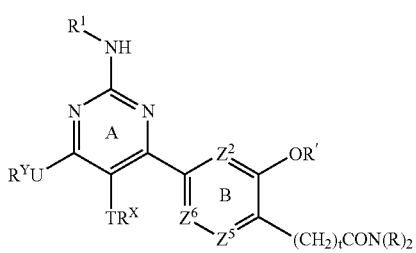
III-Q
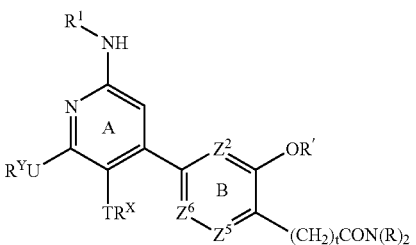
II-R
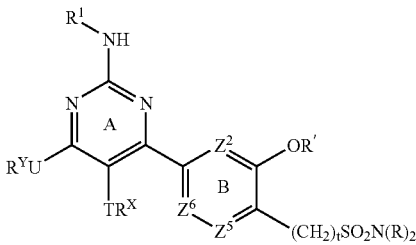
III-R
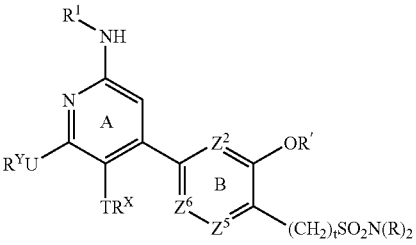
-continued
II-S
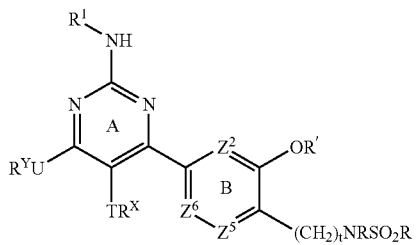
III-S
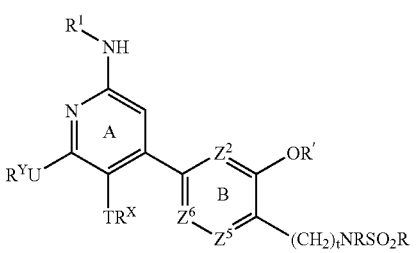
II-T
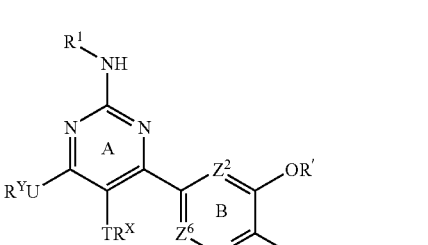
III-T
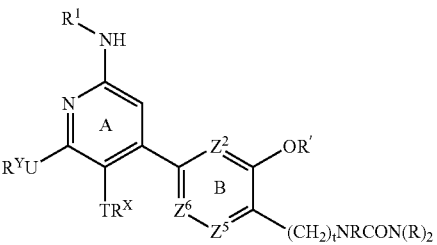
II-U
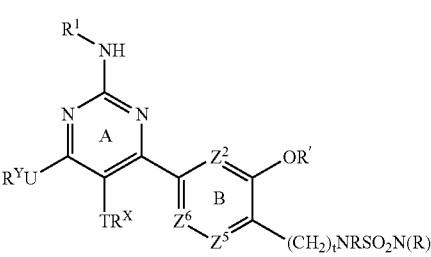
III-U
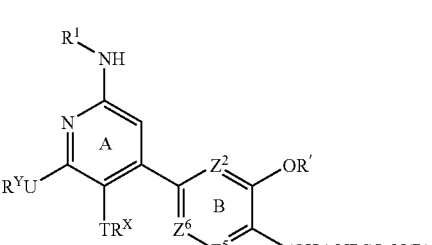

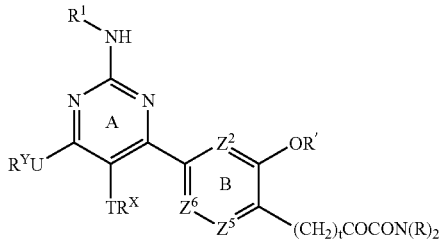

II-V

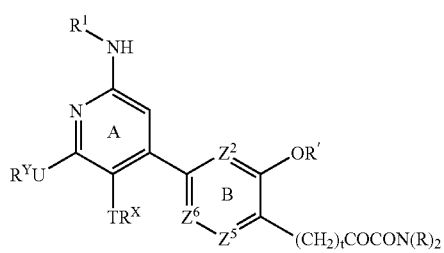

III-V

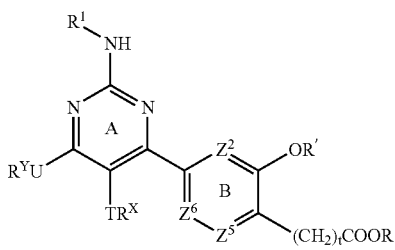

II-W

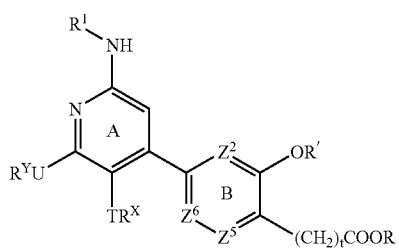

III-W

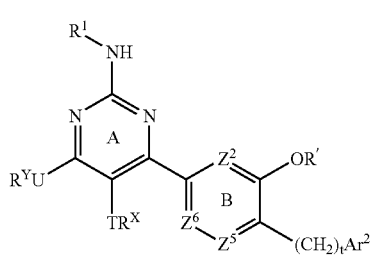

II-X

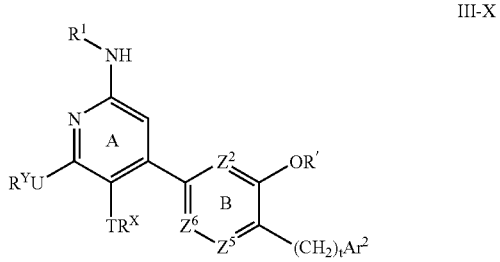

III-X

It will be appreciated that for compounds described above, ring B is selected from one of structures i, ii, v, vi, or vii. In certain exemplary embodiments, ring B is selected from i.

Certain subclasses of the foregoing compounds are described in more detail below. It will be appreciated that, for each of the compounds generally described above (formula I) and classes thereof, any combination of the subsets set forth below may be utilized to describe exemplary subclasses of the invention. In particular, certain preferred subsets include, but are not limited to the following:

i) compounds where $R^1$ is selected from an optionally substituted group selected from phenyl, cyclohexyl, cyclopentyl, pyridyl, morpholino, piperazinyl, or piperidinyl;

ii) compounds where $R^1$ is an optionally substituted group selected from phenyl, cyclohexyl, or pyridyl;

iii) compounds where $R^1$ is optionally substituted phenyl;

iv) compounds where $Ar^1$ is substituted with up to five occurrences of $ZR^Z$, and $ZR^Z$ groups are selected from halogen, R', CN, $NO_2$, —N(R)(R'), —OR', —SR', —S(O)$_2$N(R)(R'), CO($C_{1-4}$alkyl), —NRSO$_2$R', COO($C_{1-4}$alkyl).

v) compounds where q is 1 and $ZR^Z$ is F, Cl, Br, COO($C_{1-4}$alkyl), $C_{1-4}$alkyl, CN, $NO_2$, —$NH_2$, —OH, $C_{1-4}$alkoxy, —S(O)$_2NH_2$, or an optionally substituted benzyloxy, phenyloxy, or phenyl group;

vi) compounds where q is 1, and $ZR^Z$ is in the meta or para position and $ZR^Z$ is F, Cl, Br, benzyloxy, phenyl, phenyloxy, COO($C_{1-4}$alkyl), —$NH_2$, —OH, $C_{1-4}$alkoxy, or —S(O)$_2NH_2$;

vii) compounds where $TR^X$ and $UR^Y$ are selected from hydrogen, halogen, $NO_2$, CN, OR, SR or N(R)$_2$, or $C_{1-4}$aliphatic optionally substituted with oxo, OR, SR, N(R)$_2$, halogen, $NO_2$ or CN;

viii) compounds where $TR^X$ and $UR^Y$ groups are selected from hydrogen, Me, OH, OMe or N(R)$_2$;

ix) compounds where $TR^X$ and $UR^Y$ are each hydrogen;

x) compounds where $Z^2$ and $Z^6$ are each CH;

xi) compounds where t is 0;

xii) compounds where t is 1; and xiii) compounds where $Ar^2$ is an optionally substituted tetrazole, triazole, oxazole, thiazole, thiadiazole, oxadiazole or pyridyl group Certain other exemplary embodiments relate to those compounds where $R^1$ is optionally substituted phenyl and ring B is phenyl and compounds have one of the structures depicted below:

II-A-(i)
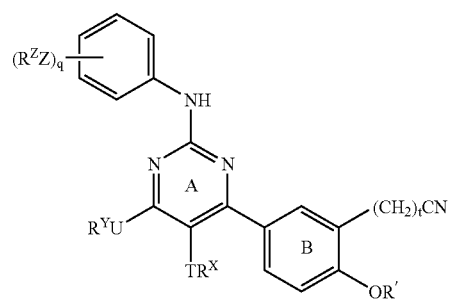
III-C-(i)
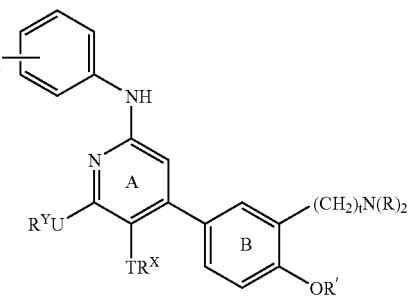
III-A-(i)
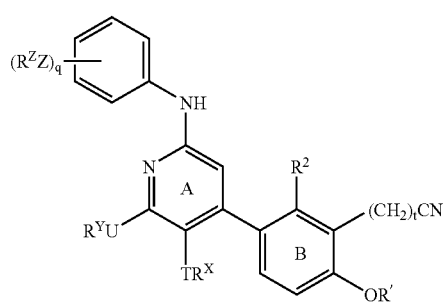
II-D-(i)
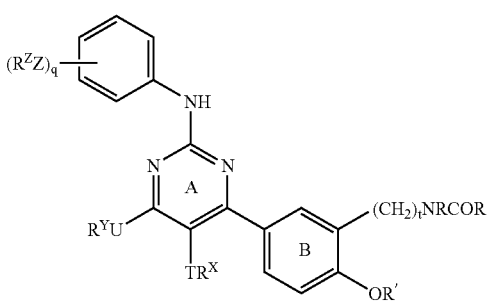
II-B-(i)
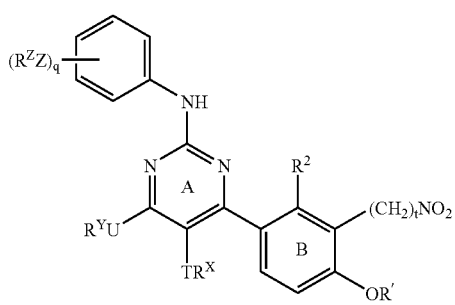
III-D-(i)
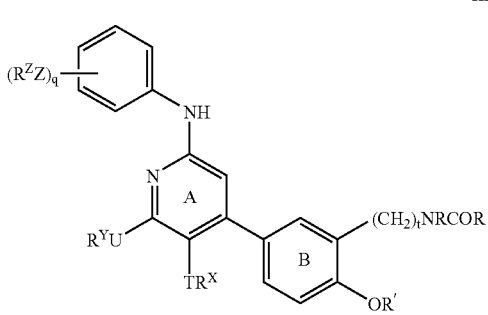
III-B-(i)
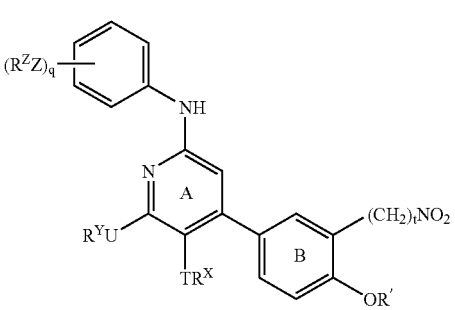
II-E-(i)
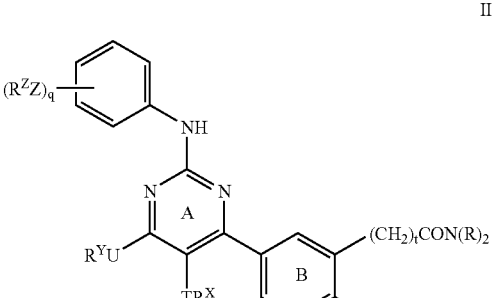
II-C-(i)
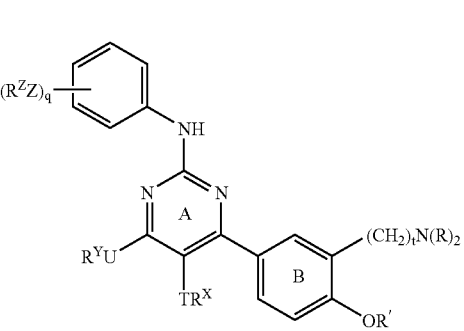
III-E-(i)
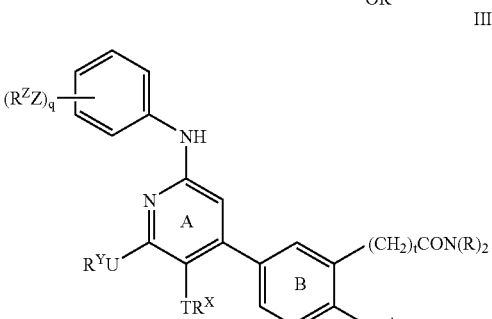

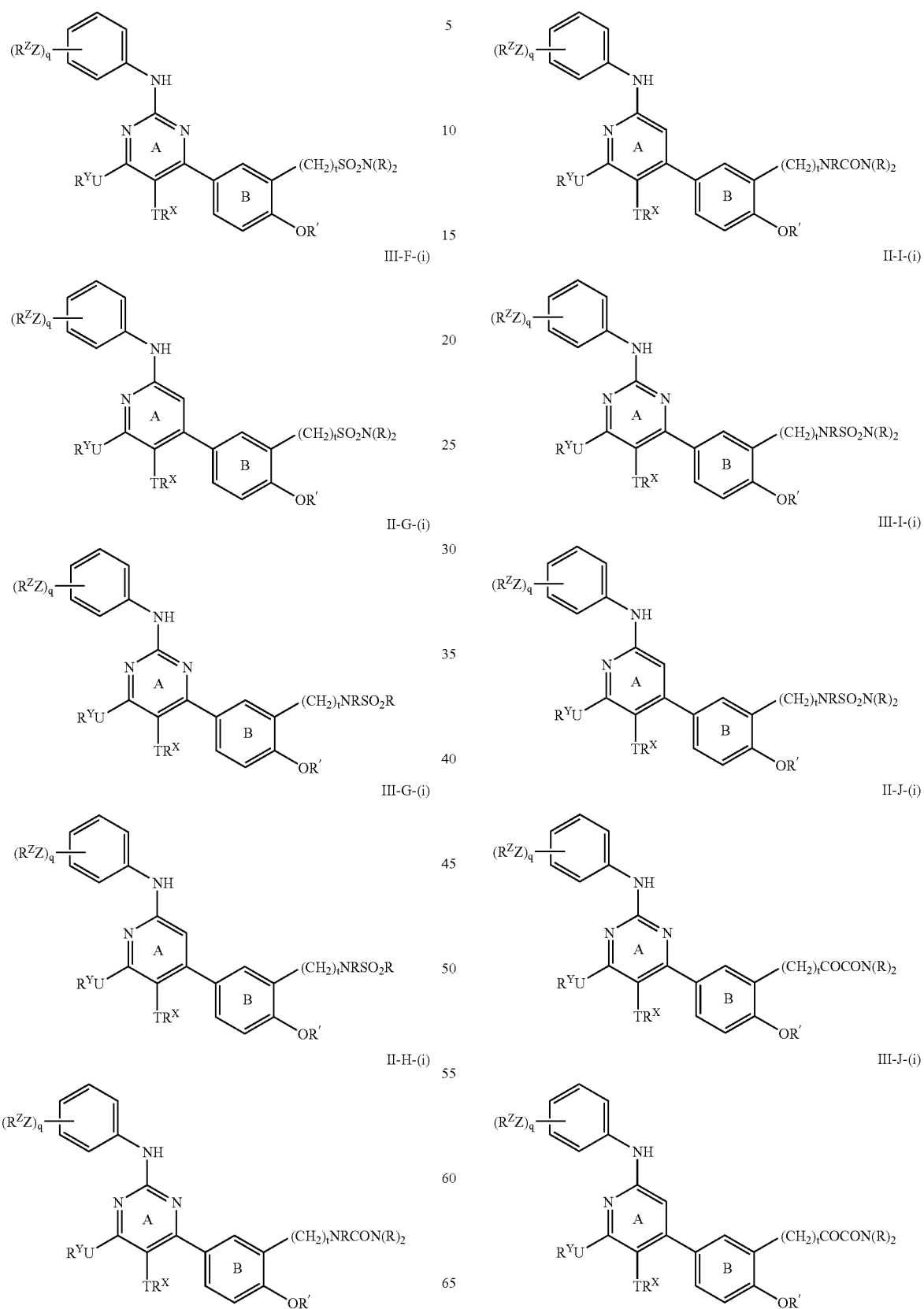

-continued
II-K-(i)
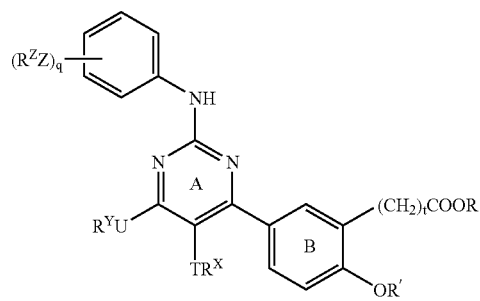
III-K-(i)
II-L-(i)
III-L-(i)
II-M-(i)
-continued
III-M-(i)
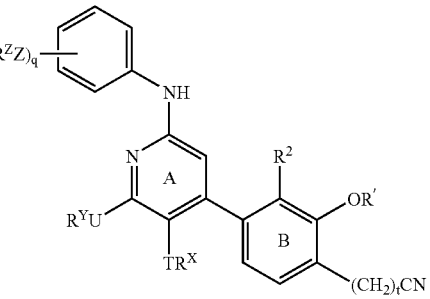
II-N-(i)
III-N-(i)
II-O-(i)
III-O-(i)

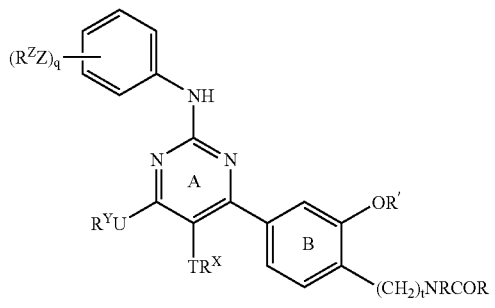
II-P-(i)
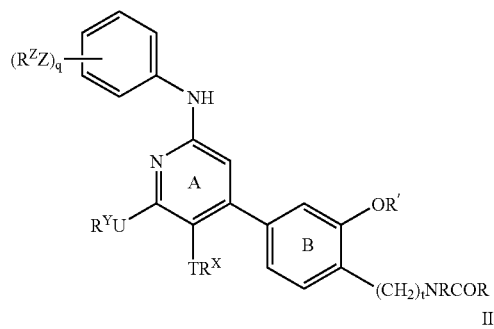
III-P-(i)
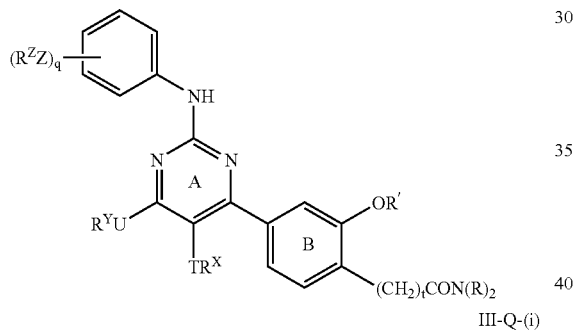
II-Q-(i)
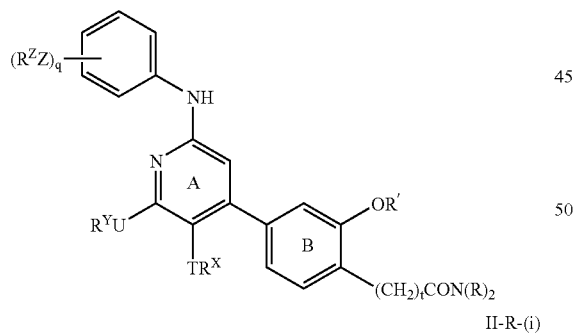
III-Q-(i)
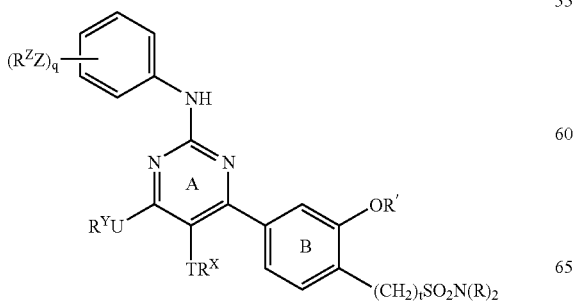
II-R-(i)
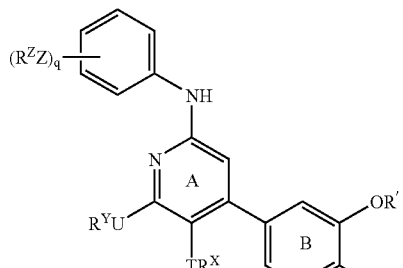
III-R-(i)
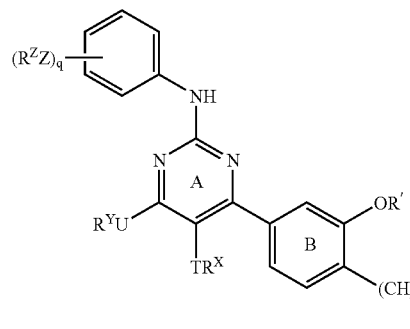
II-S-(i)
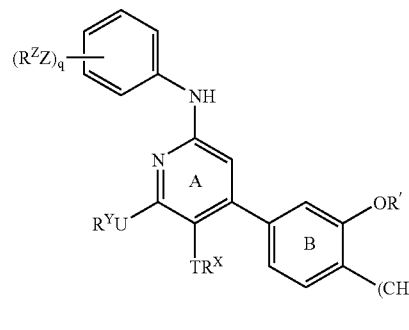
III-S-(i)
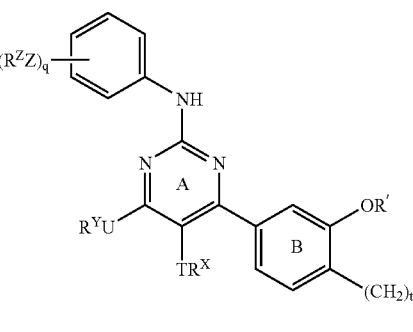
II-T-(i)
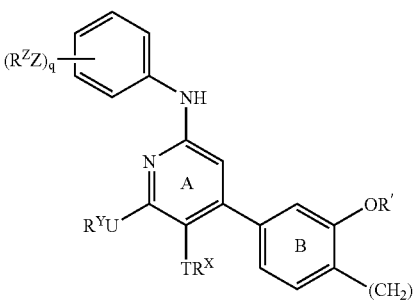
III-T-(i)

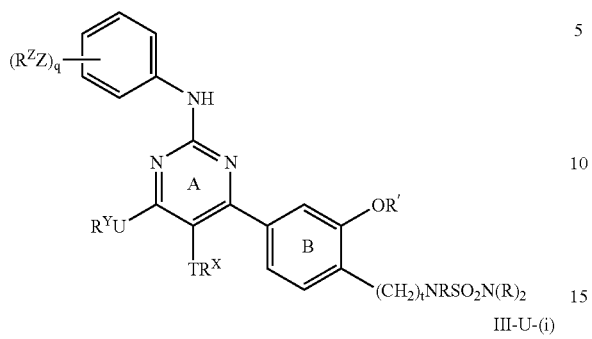
II-U-(i)
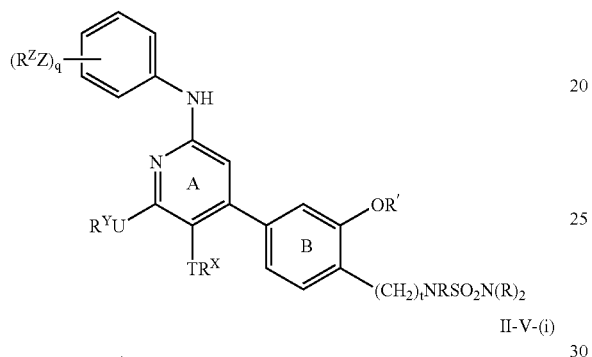
III-U-(i)
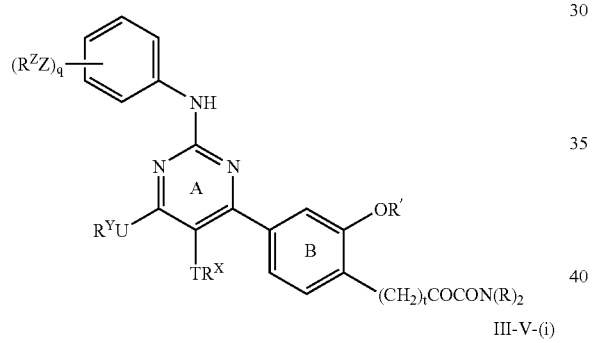
II-V-(i)
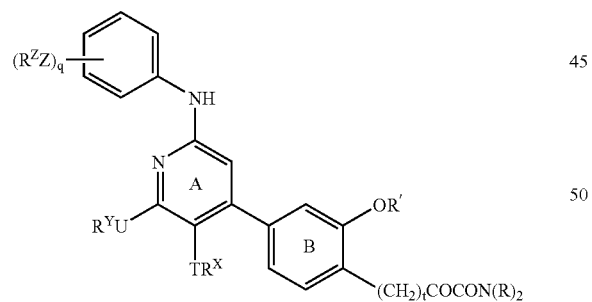
III-V-(i)
II-W-(i)
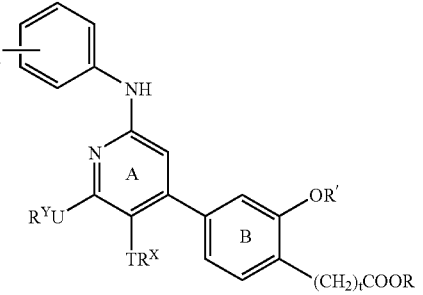
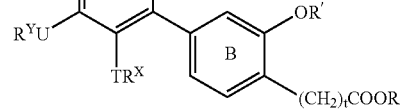
III-W-(i)
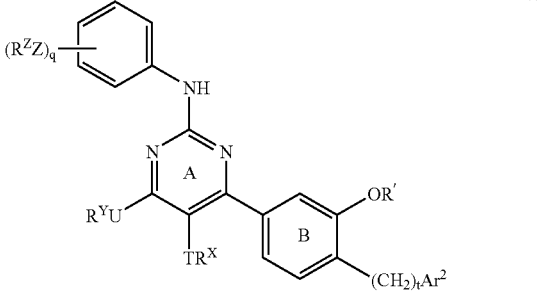
II-X-(i)
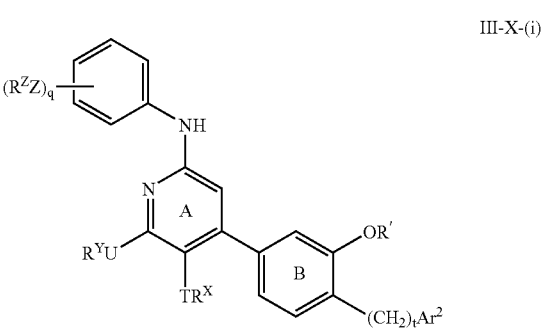
III-X-(i)
Certain exemplary embodiments also relate to those compounds where ring A is a pyrimidine; $UR^Y$, and $TR^X$ are each hydrogen, and the compounds have the general structures depicted generally below:
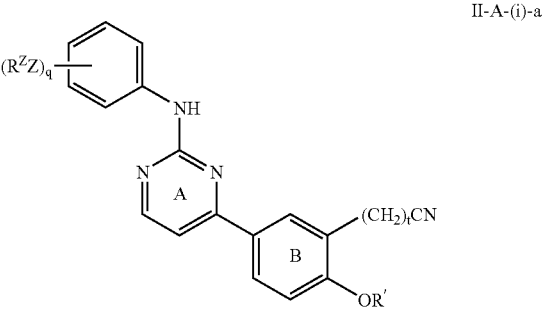
II-A-(i)-a II-B-(i)-a
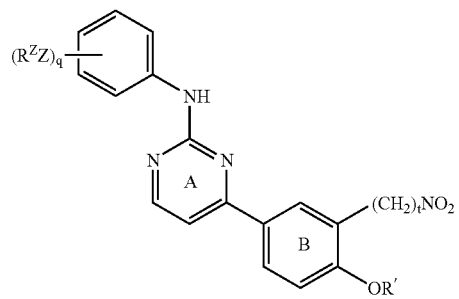
II-C-(i)-a
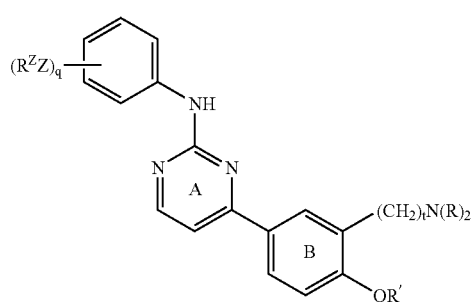
II-D-(i)-a
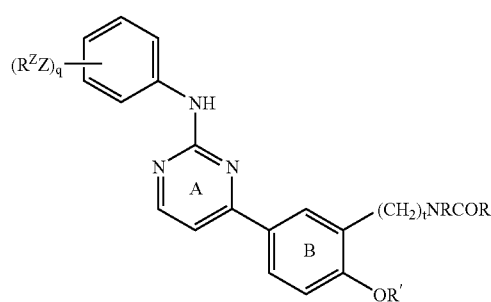
II-E-(i)-a
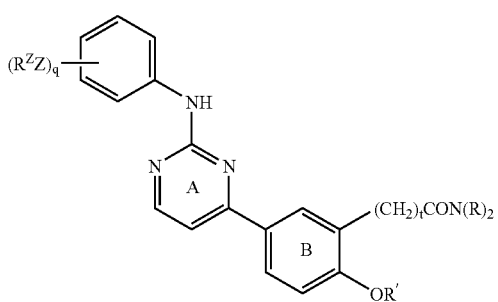
II-F-(i)-a
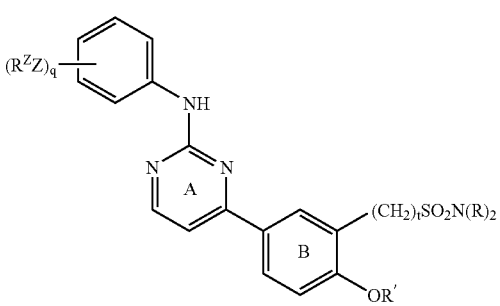
II-G-(i)-a
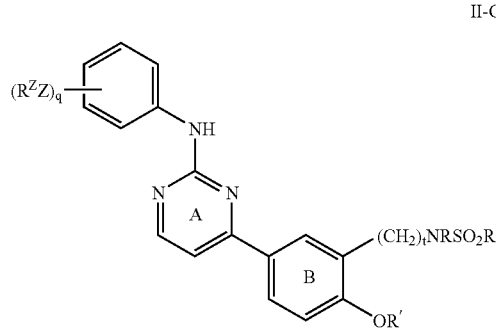
II-H-(i)-a
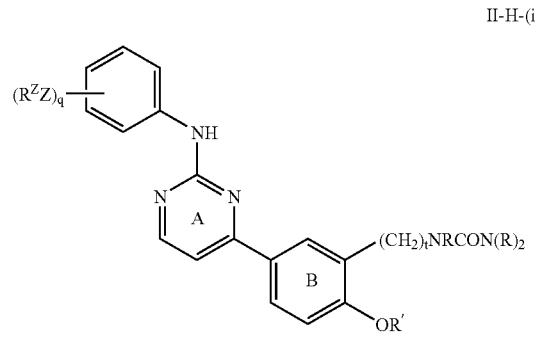
II-I-(i)-a
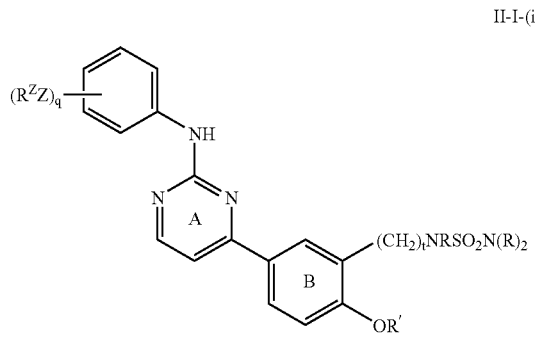
II-J-(i)-a
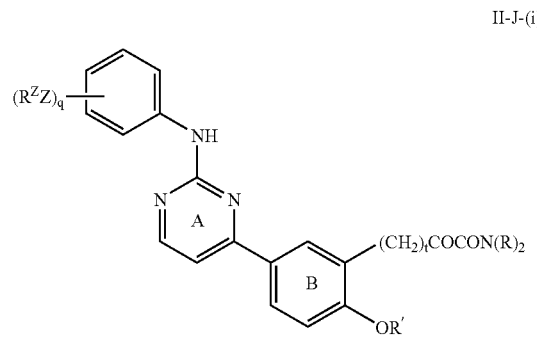
II-K-(i)-a
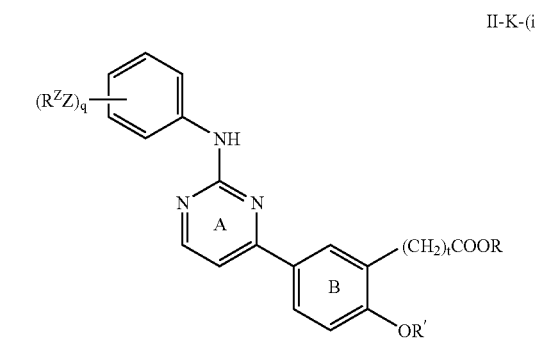

-continued
II-L-(i)-a
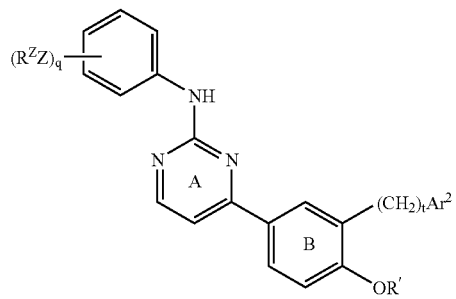
II-M-(i)-a
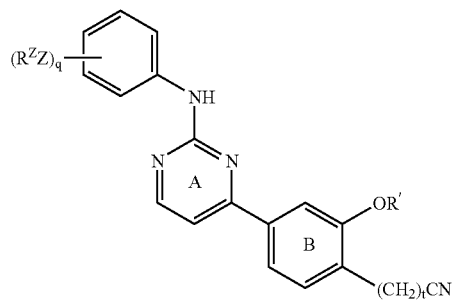
II-N-(i)-a
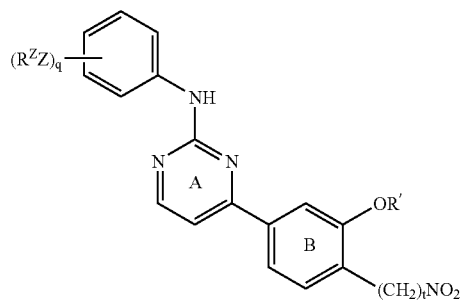
II-O-(i)-a
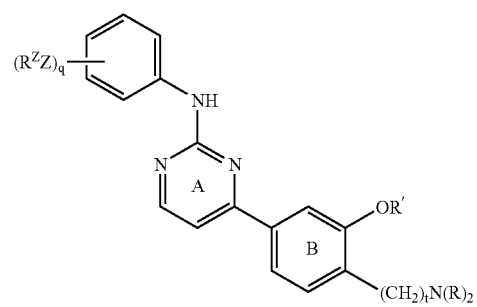
II-P-(i)-a
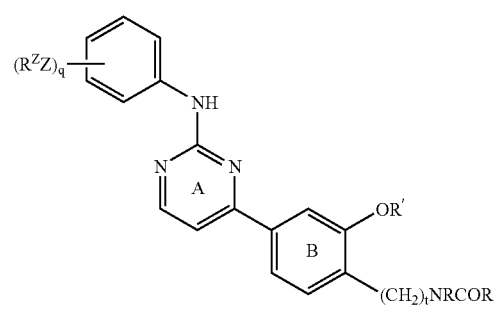
-continued
II-Q-(i)-a
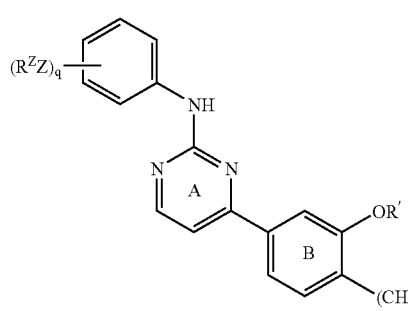
II-R-(i)-a
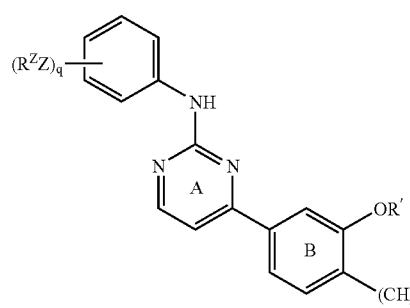
II-S-(i)-a
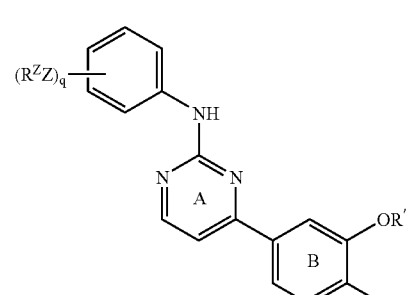
II-T-(i)-a
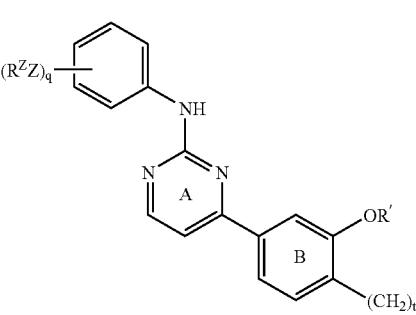
II-U-(i)-a
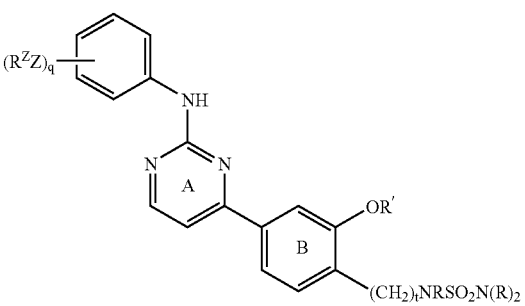

-continued

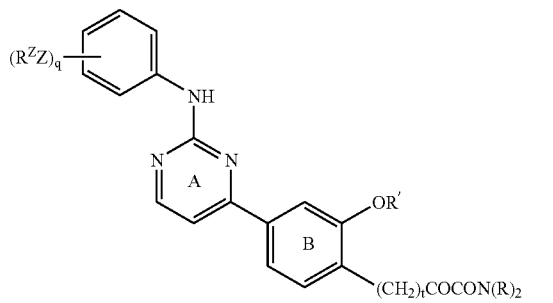

Certain exemplary subsets for each of the compounds described above include those compounds where:

a. q is 0, 1, or 2, and $ZR^Z$ is halogen, R', CN, $NO_2$, —N(R)(R'), —OR', —SR', —S(O)$_2$N(R)(R'), CO(C$_{1-4}$ alkyl), —NRSO$_2$R', COO(C$_{1-4}$alkyl);
b. t is 0;
c. R is optionally substituted C$_{1-6}$alkyl or hydrogen; and
d. R' is optionally substituted C$_{1-6}$alkyl or hydrogen.

Representative examples of compounds of formula II and III are set forth below in Tables 1 and 2 below.

TABLE 1

Examples of Compounds of Formula II:

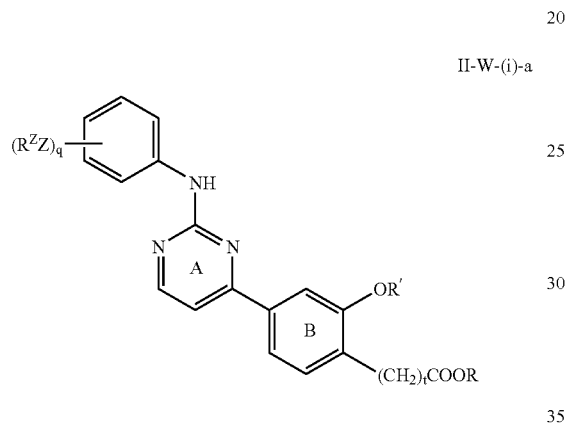

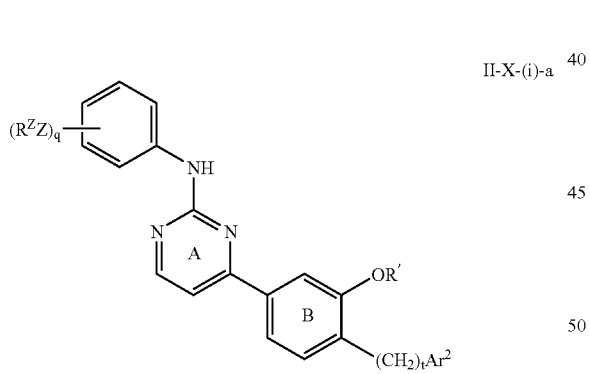

TABLE 1-continued
Examples of Compounds of Formula II:
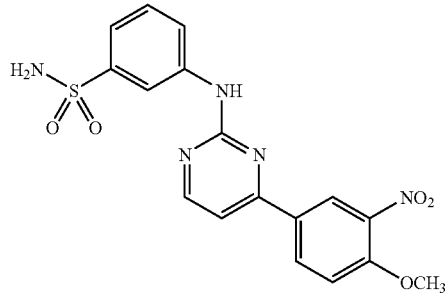
II-5
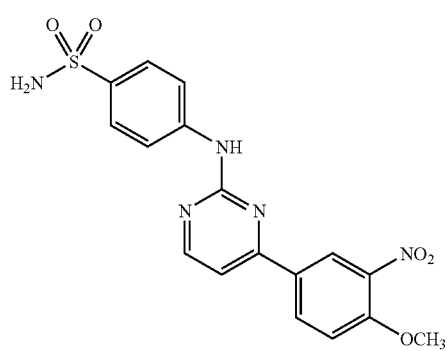
II-6
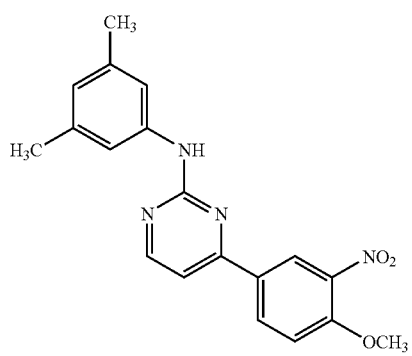
II-7
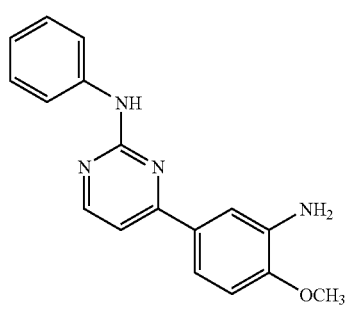
II-8
TABLE 1-continued
Examples of Compounds of Formula II:
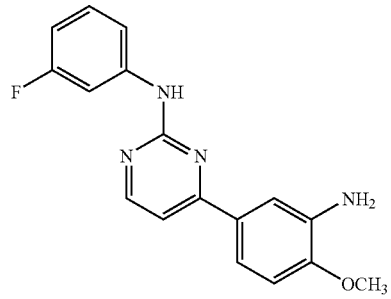
II-9
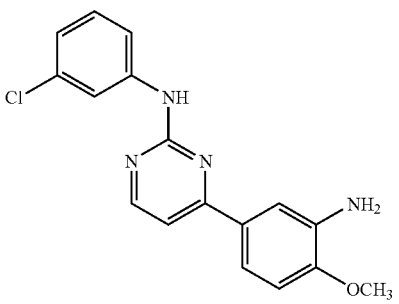
II-10
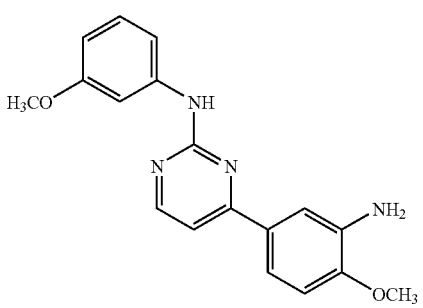
II-11
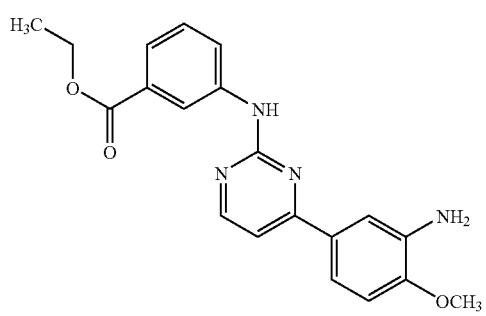
II-12

TABLE 1-continued
Examples of Compounds of Formula II:
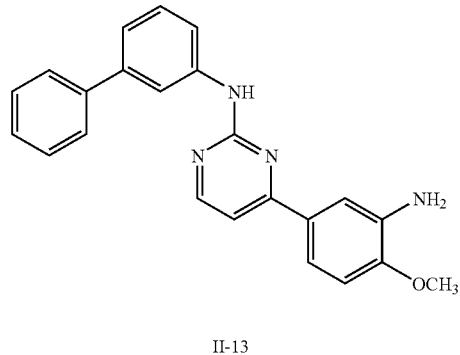
II-13
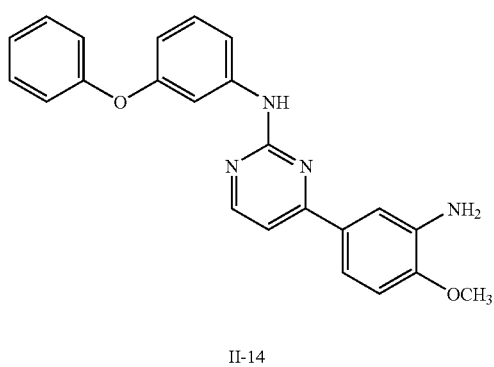
II-14
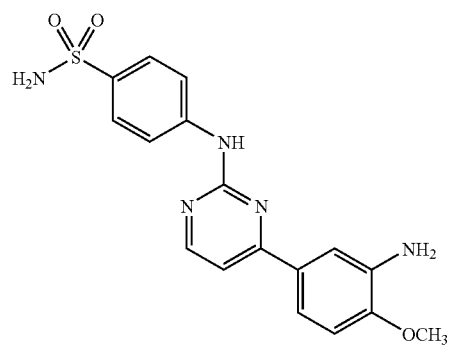
II-15
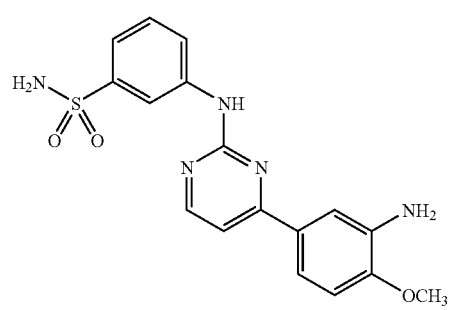
II-16
TABLE 1-continued
Examples of Compounds of Formula II:
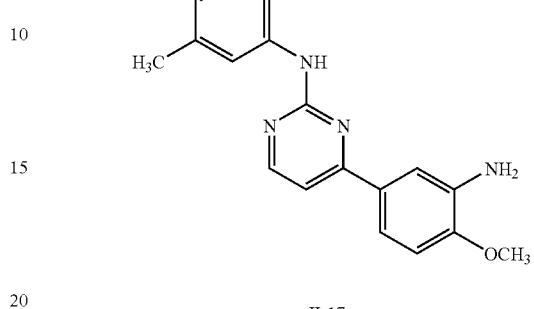
II-17
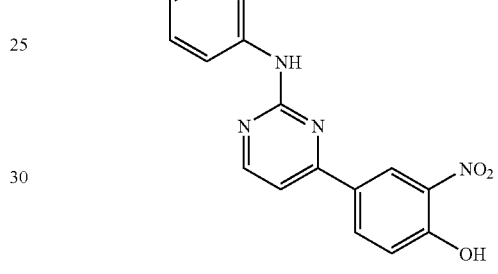
II-18
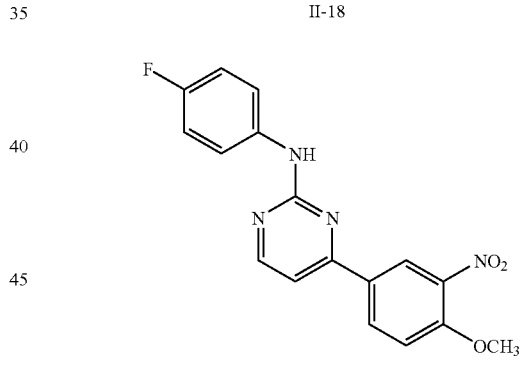
II-19
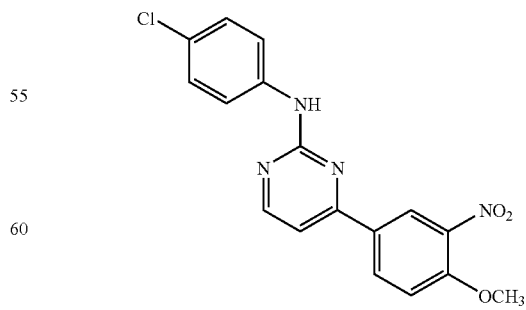
II-20

TABLE 1-continued
Examples of Compounds of Formula II:
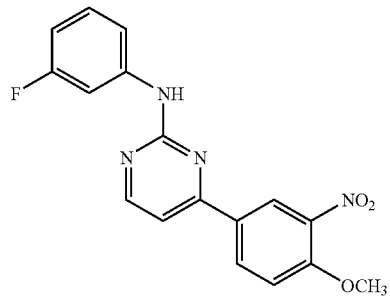
II-21
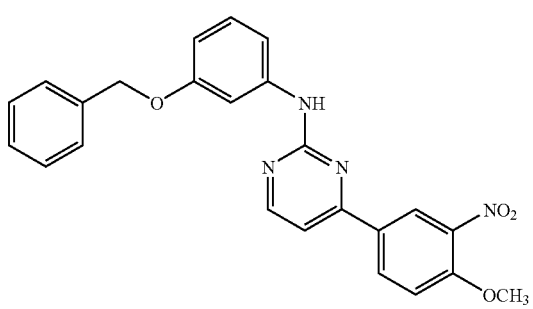
II-22
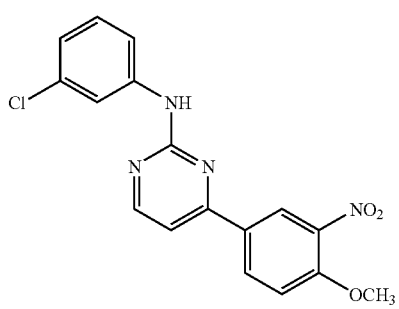
II-23
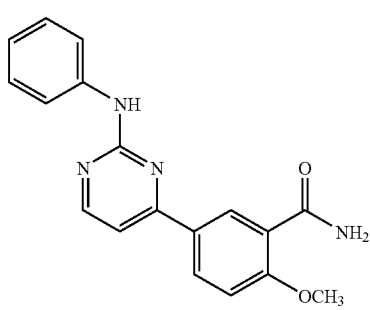
II-24
TABLE 1-continued
Examples of Compounds of Formula II:
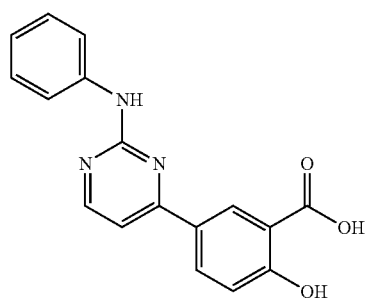
II-25
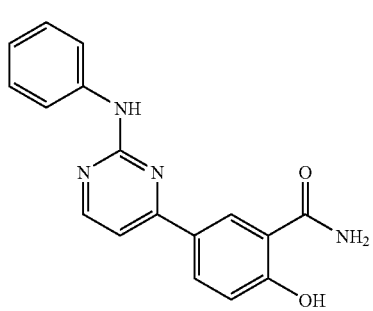
II-26
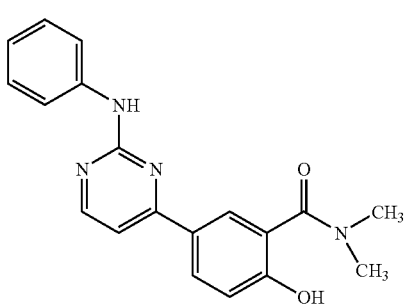
II-27
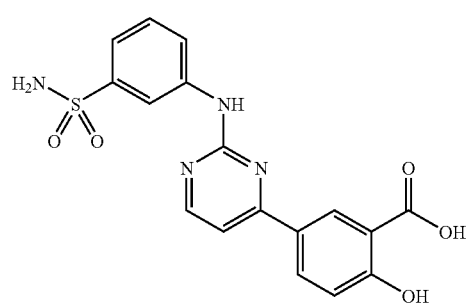
II-28

TABLE 1-continued
Examples of Compounds of Formula II:
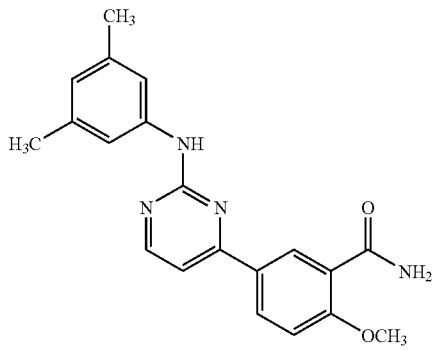
II-29
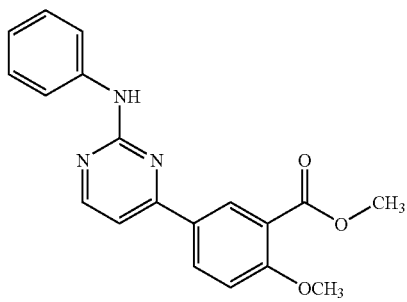
II-30
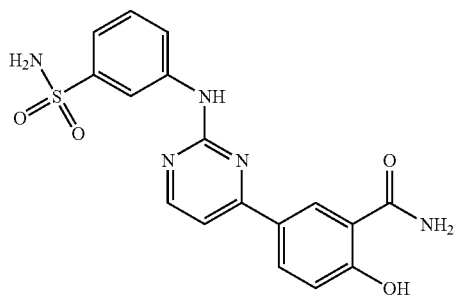
II-31
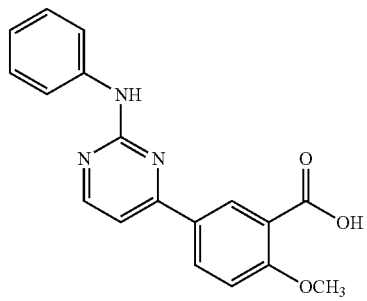
II-32
TABLE 1-continued
Examples of Compounds of Formula II:
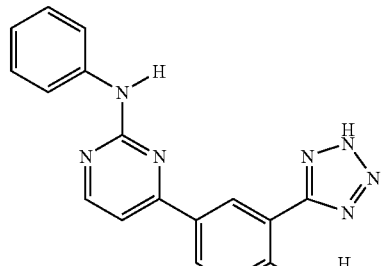
II-33
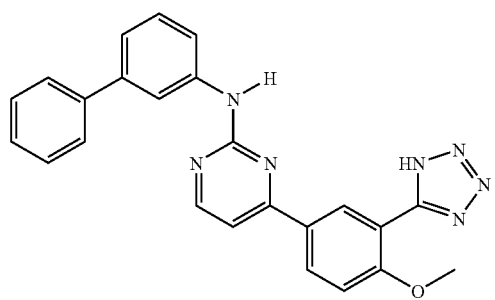
II-34
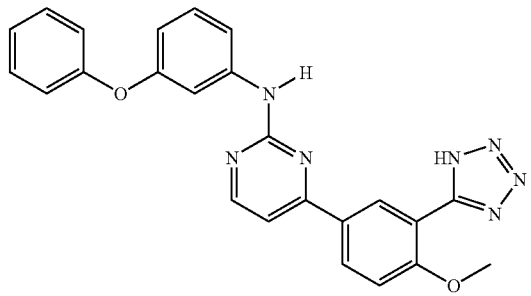
II-35
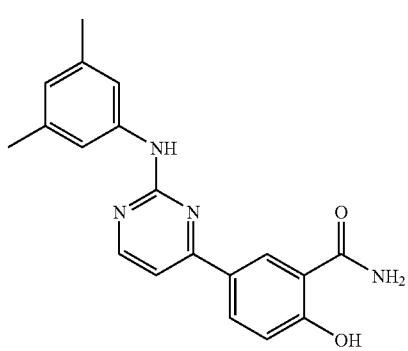
II-36

TABLE 1-continued
Examples of Compounds of Formula II:
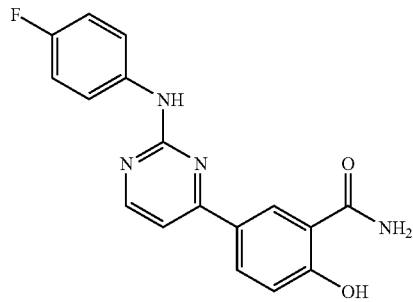
II-37
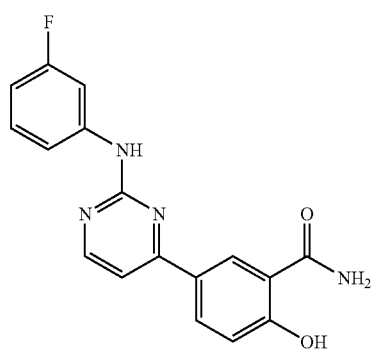
II-38
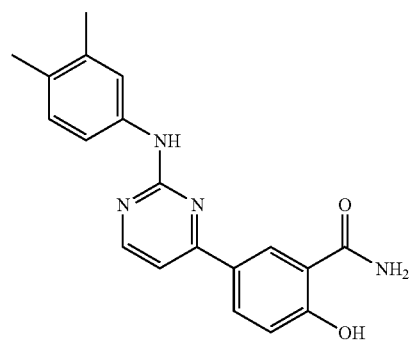
II-39
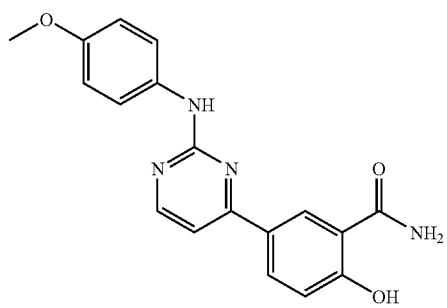
II-40
TABLE 1-continued
Examples of Compounds of Formula II:
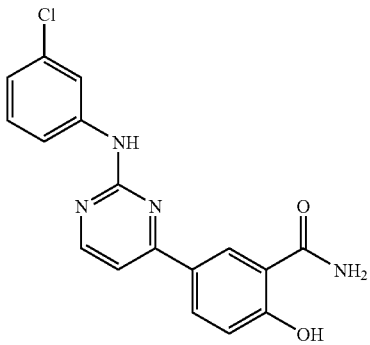
II-41
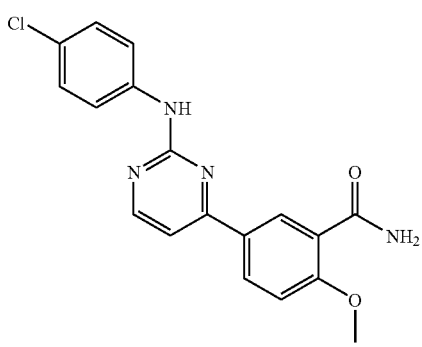
II-42
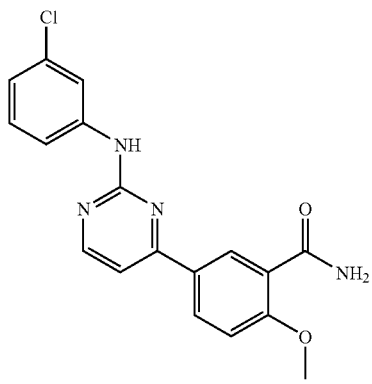
II-43
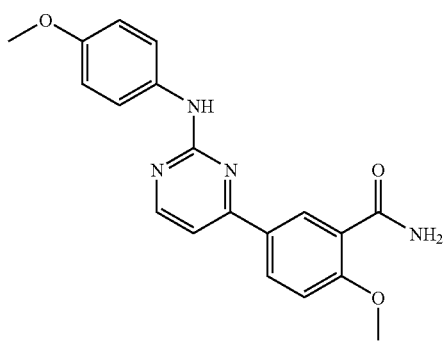
II-44

TABLE 1-continued
Examples of Compounds of Formula II:
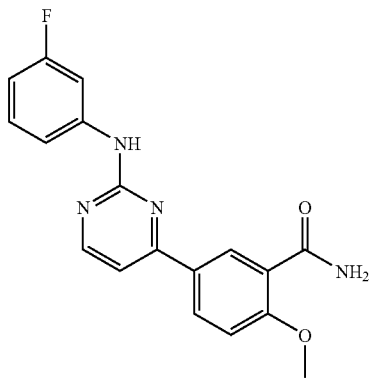
II-45
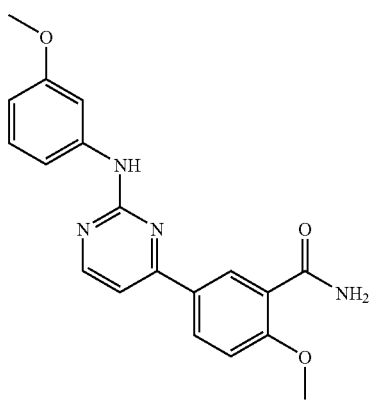
II-46
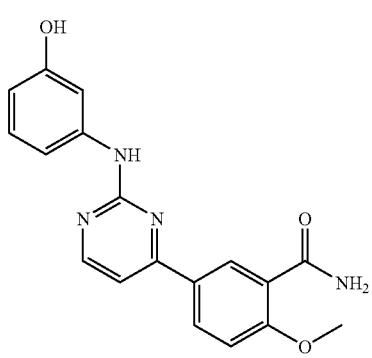
II-47
TABLE 1-continued
Examples of Compounds of Formula II:
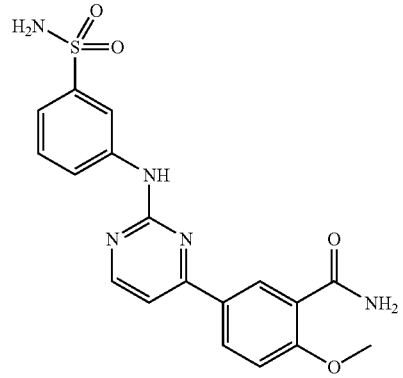
II-48
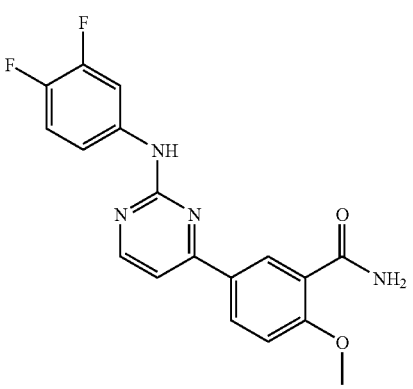
II-49
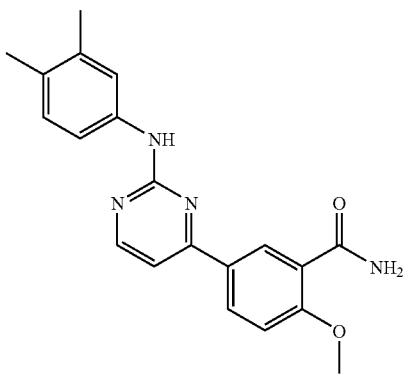
II-50

TABLE 1-continued
Examples of Compounds of Formula II:
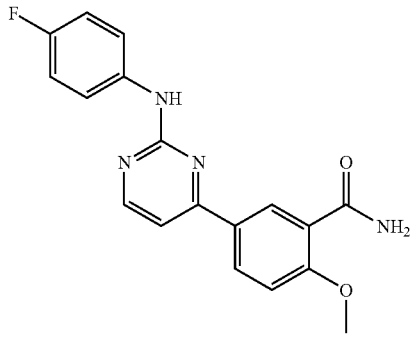
II-51
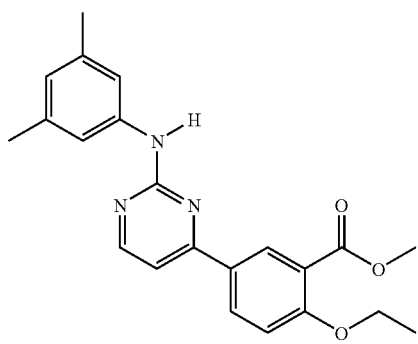
II-52
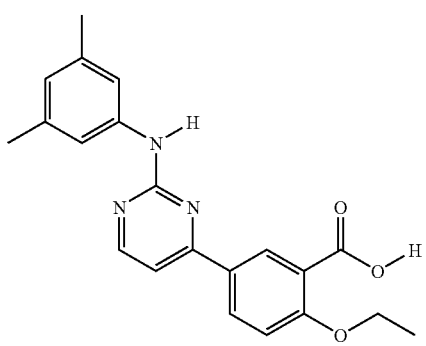
II-53
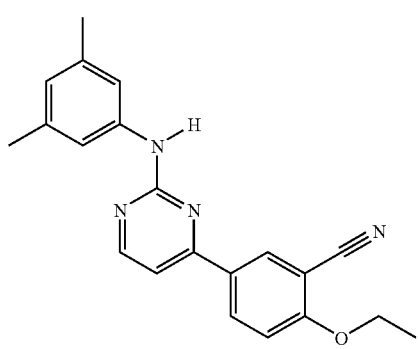
II-54
TABLE 1-continued
Examples of Compounds of Formula II:
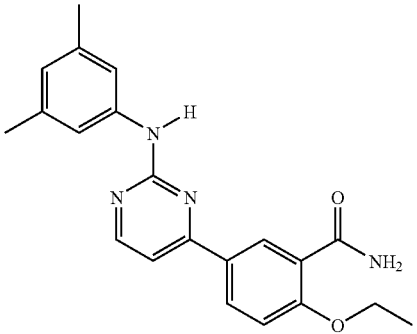
II-55
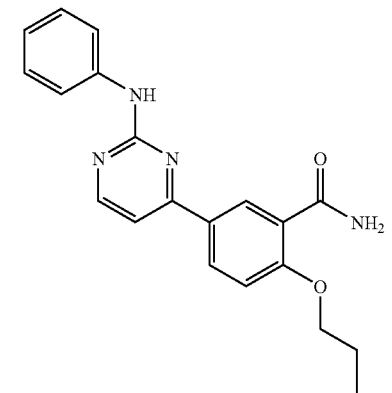
II-56
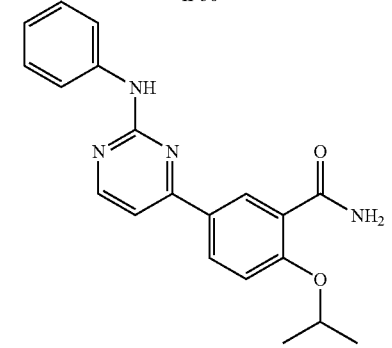
II-57
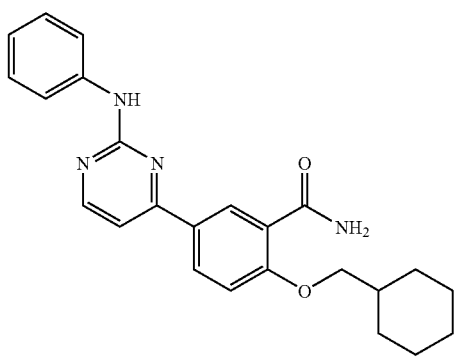
II-58

TABLE 1-continued
Examples of Compounds of Formula II:
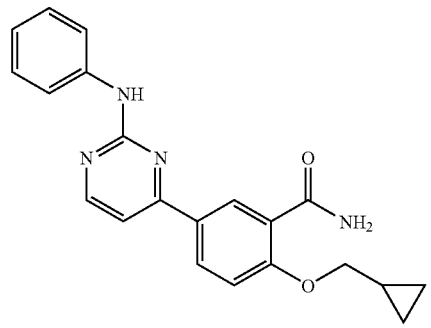
II-59
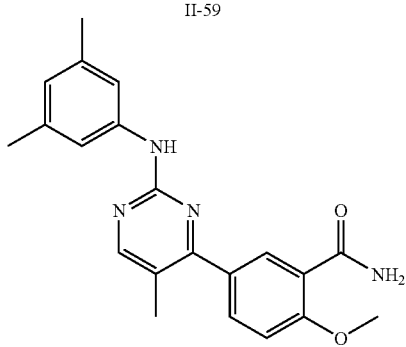
II-60
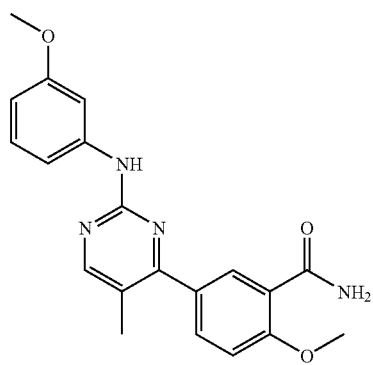
II-61
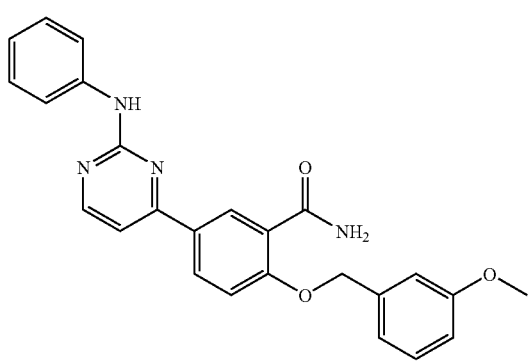
II-62
TABLE 1-continued
Examples of Compounds of Formula II:
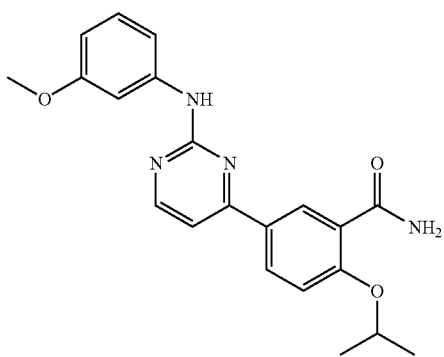
II-63
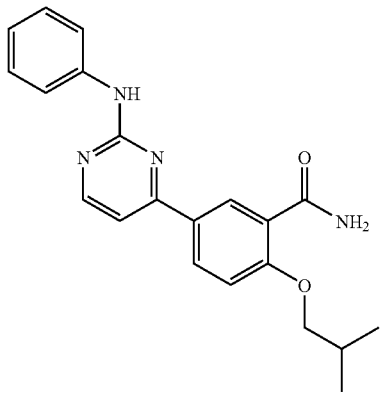
II-64
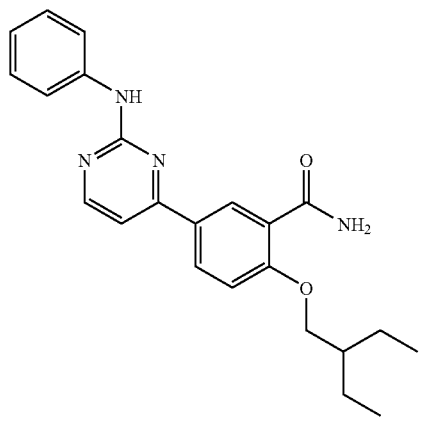
II-65

TABLE 1-continued
Examples of Compounds of Formula II:
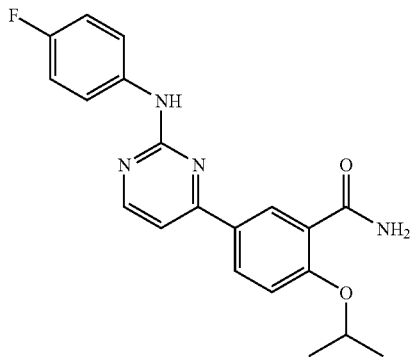
II-66
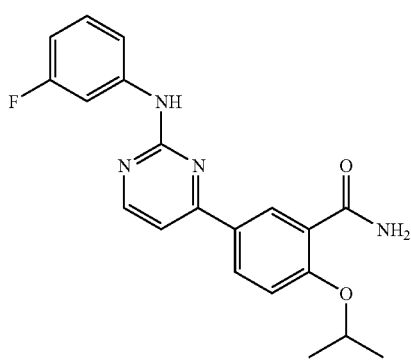
II-67
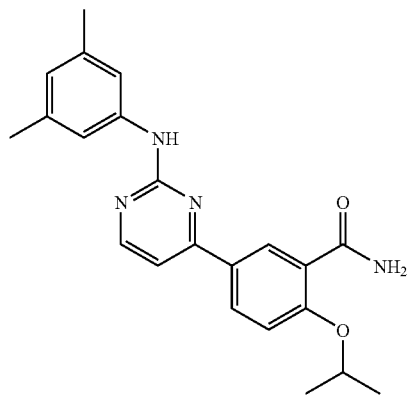
II-68
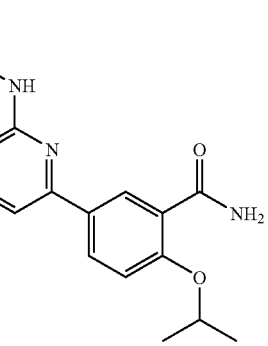
II-69
TABLE 1-continued
Examples of Compounds of Formula II:
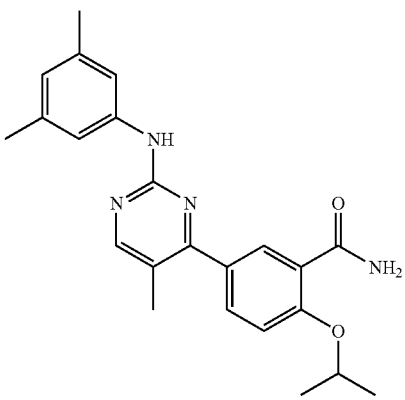
II-70
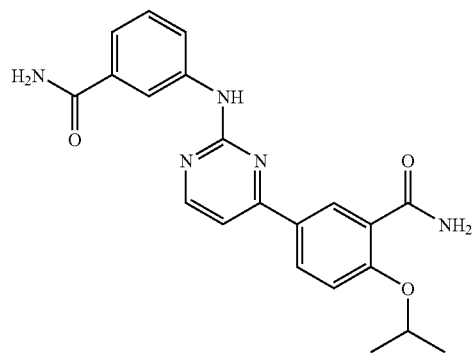
II-71
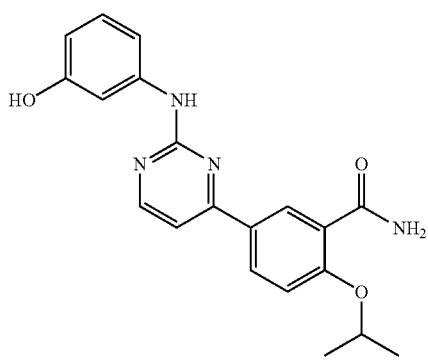
II-72

TABLE 1-continued
Examples of Compounds of Formula II:
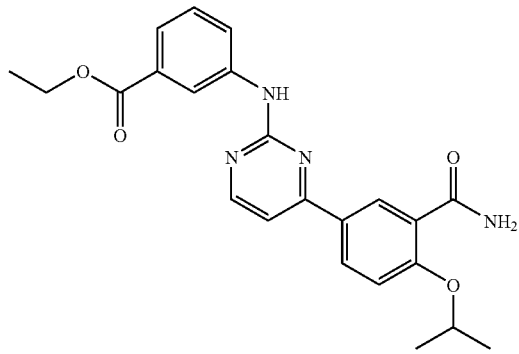
II-73
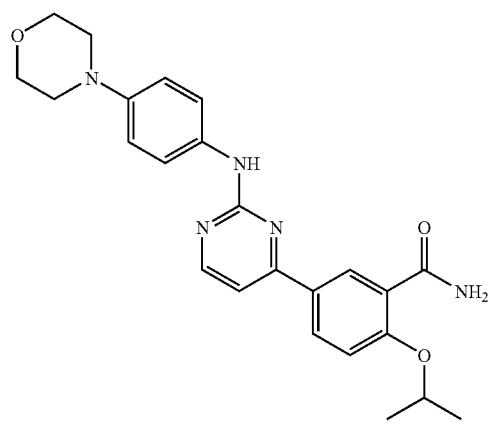
II-74
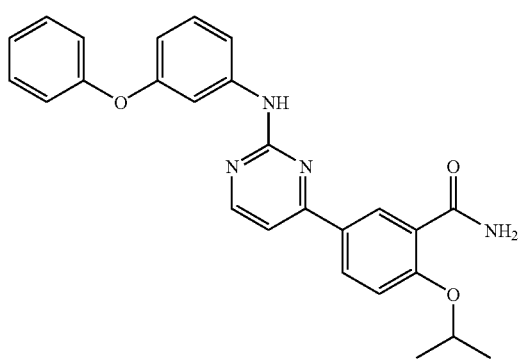
II-75
TABLE 1-continued
Examples of Compounds of Formula II:
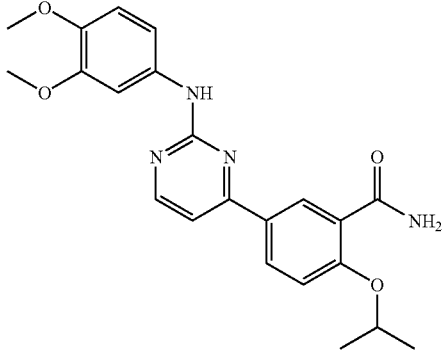
II-76
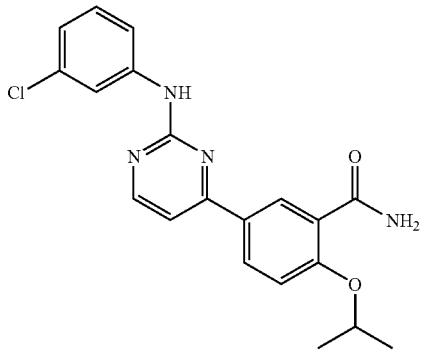
II-77
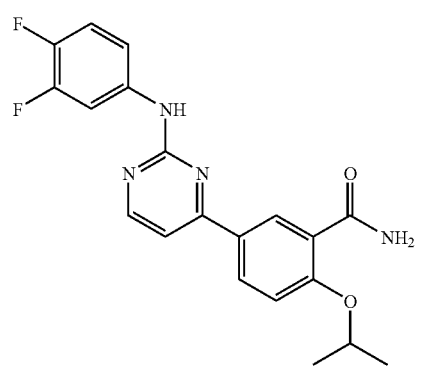
II-78

TABLE 1-continued
Examples of Compounds of Formula II:
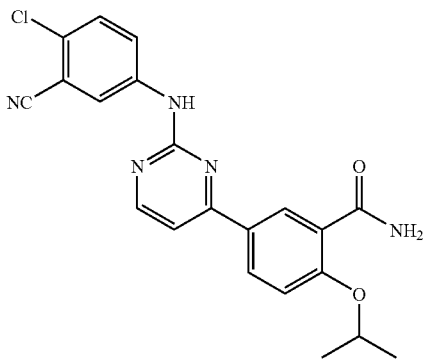
II-79
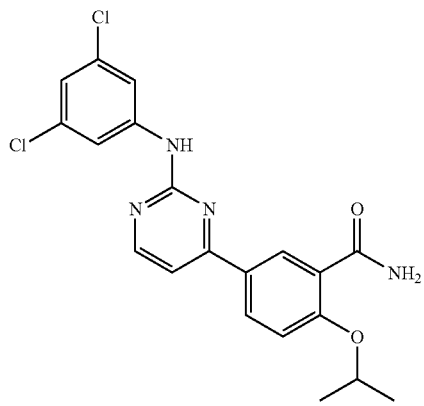
II-80
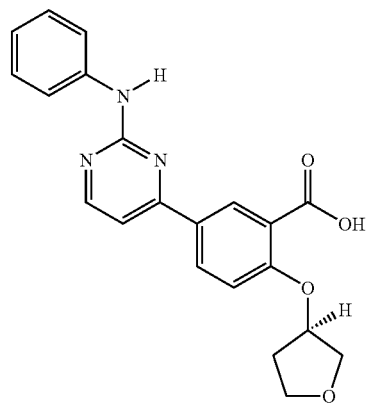
II-81
TABLE 1-continued
Examples of Compounds of Formula II:
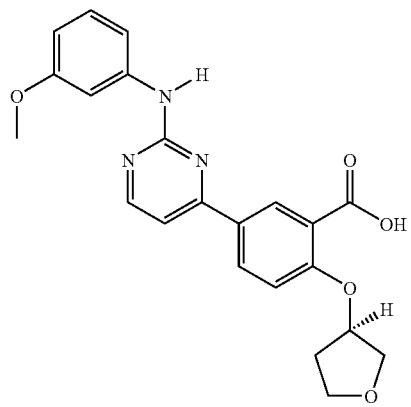
II-82
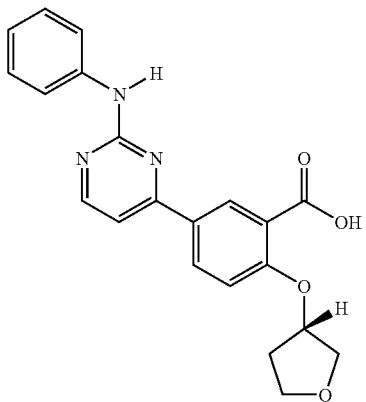
II-83
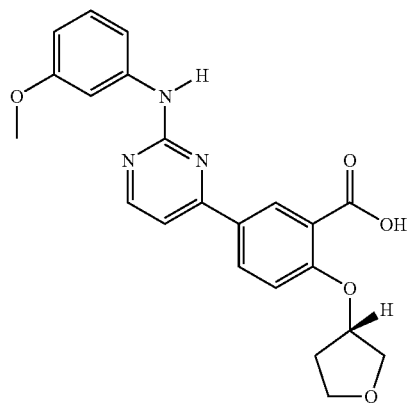
II-84

TABLE 1-continued
Examples of Compounds of Formula II:
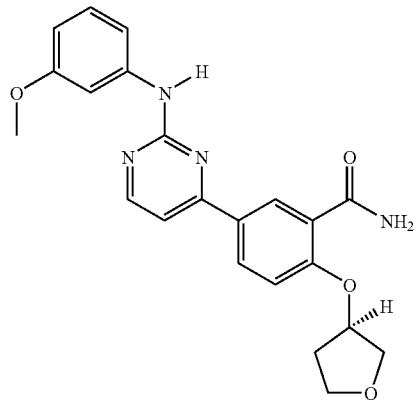
II-85
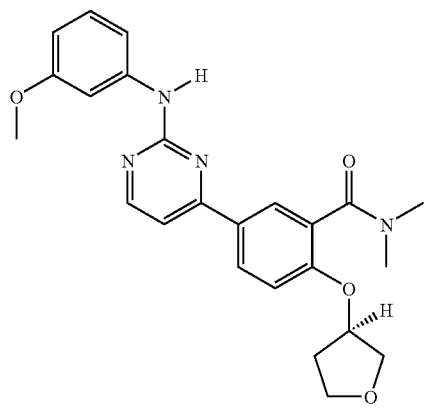
II-86
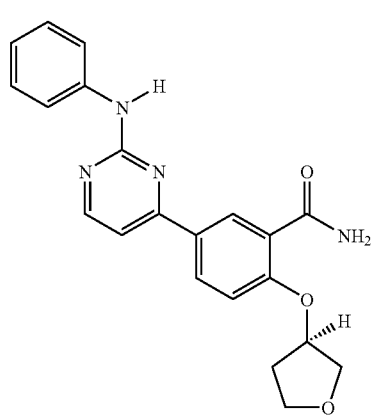
II-87
TABLE 1-continued
Examples of Compounds of Formula II:
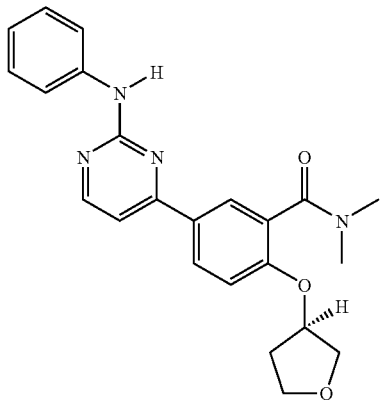
II-88
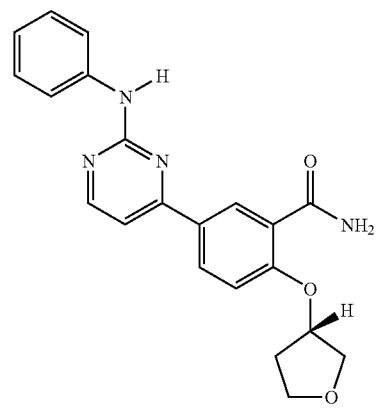
II-89
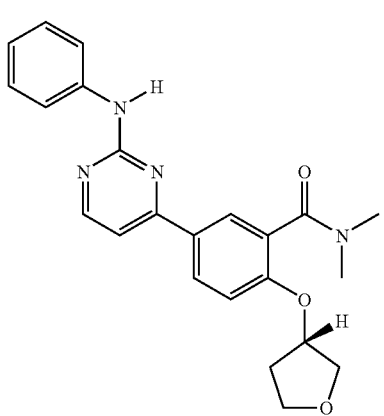
II-90

TABLE 1-continued
Examples of Compounds of Formula II:
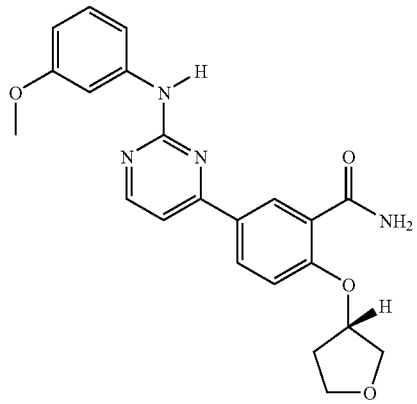
II-91
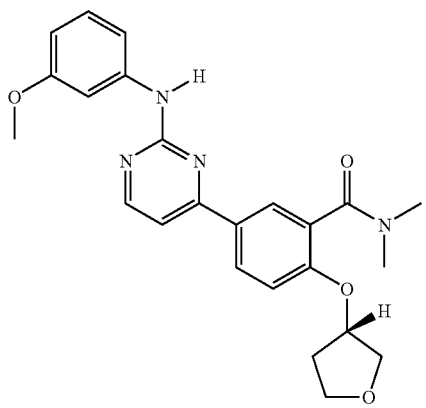
II-92
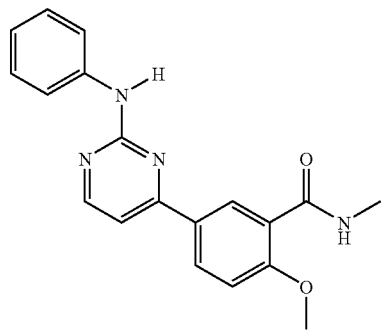
II-93
TABLE 1-continued
Examples of Compounds of Formula II:
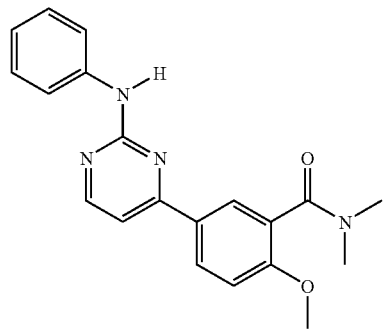
II-94
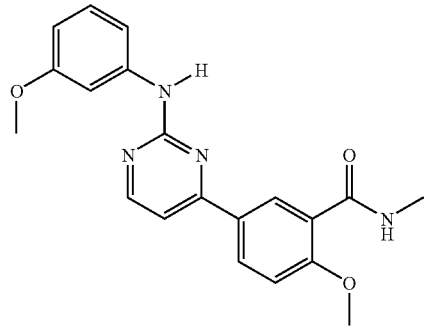
II-95
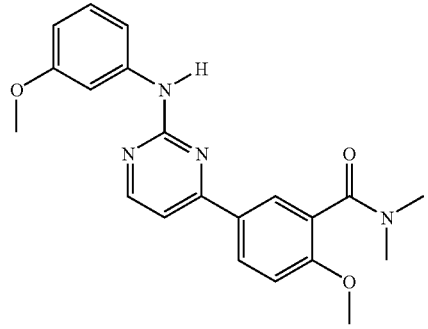
II-96
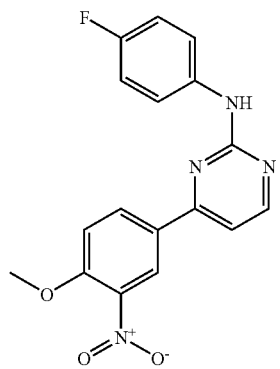
II-97

TABLE 1-continued
Examples of Compounds of Formula II:
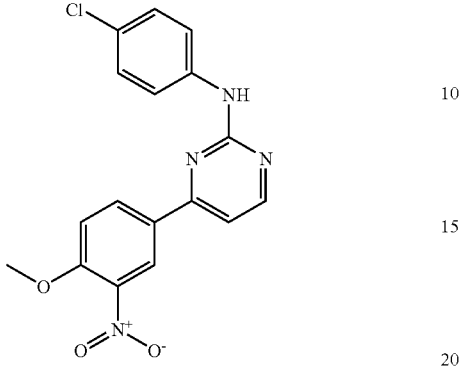
II-98
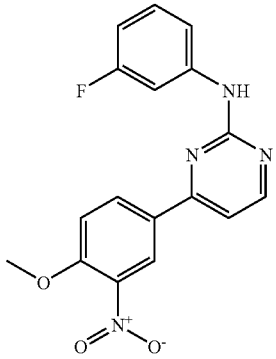
II-99
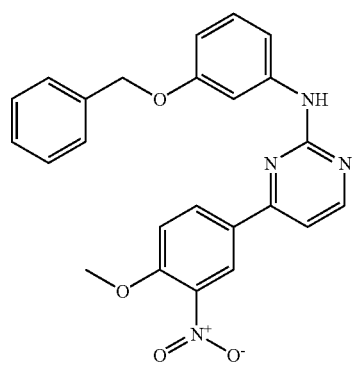
II-100
TABLE 1-continued
Examples of Compounds of Formula II:
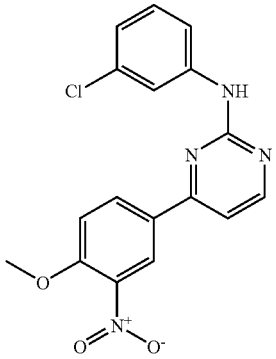
II-101
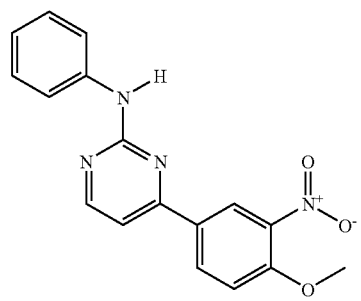
II-102
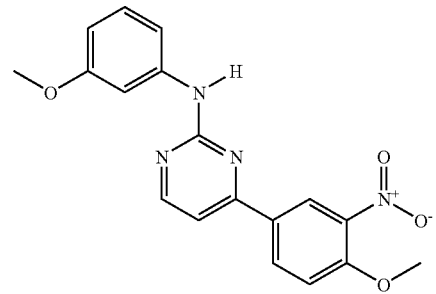
II-103
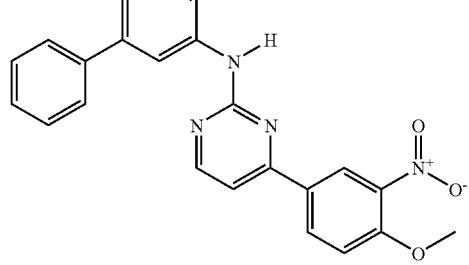
II-104

TABLE 1-continued
Examples of Compounds of Formula II:
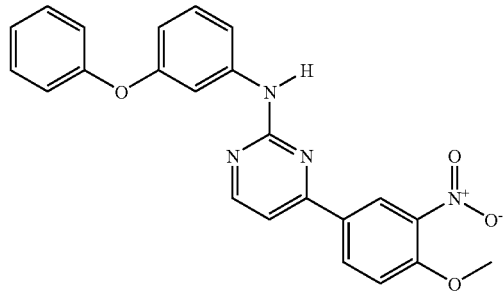
II-105
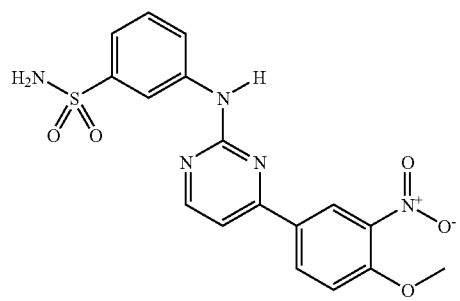
II-106
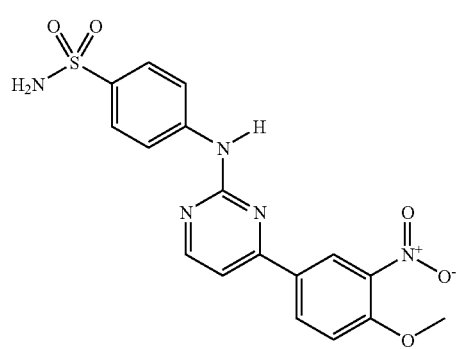
II-107
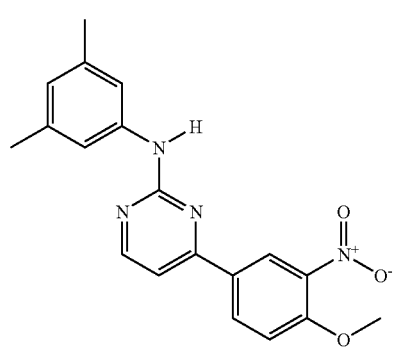
II-108
TABLE 1-continued
Examples of Compounds of Formula II:
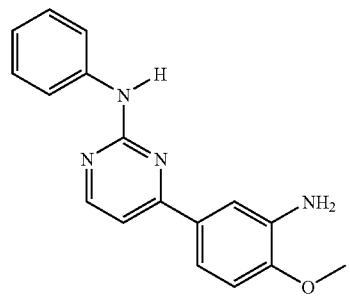
II-109
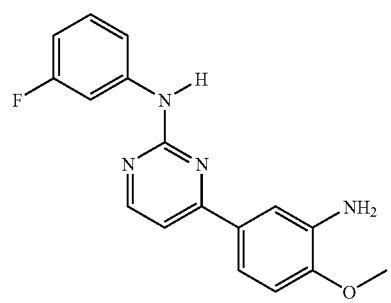
II-110
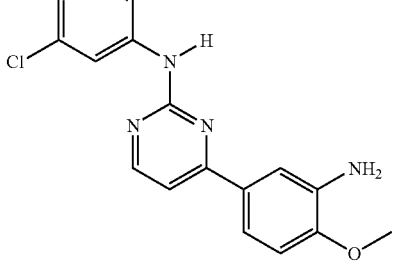
II-111
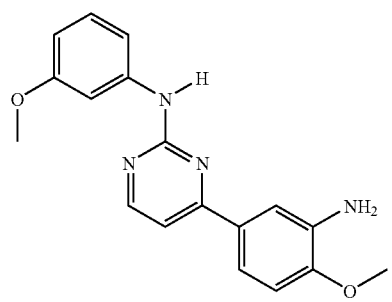
II-112

TABLE 1-continued
Examples of Compounds of Formula II:
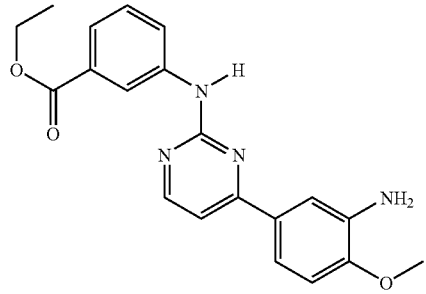
II-113
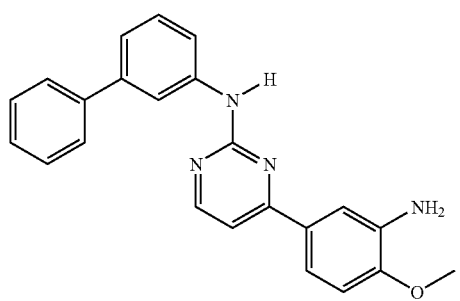
II-114
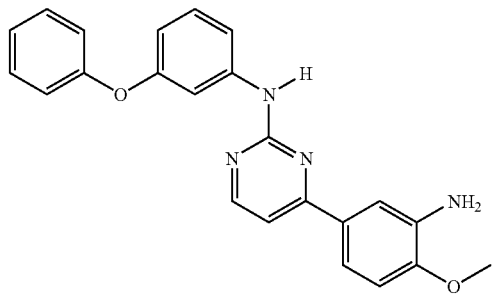
II-115
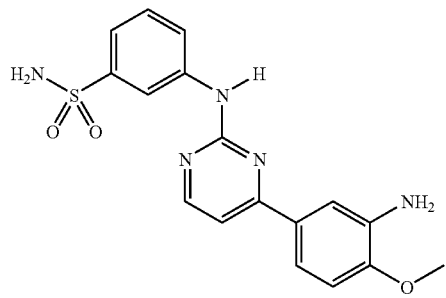
II-116
TABLE 1-continued
Examples of Compounds of Formula II:
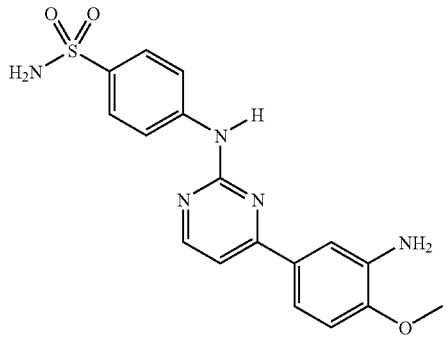
II-117
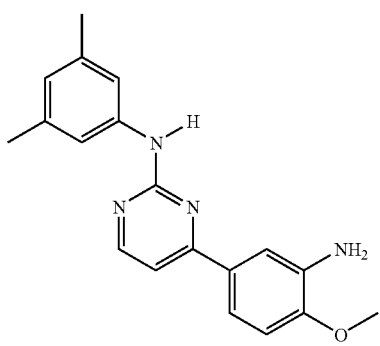
II-118
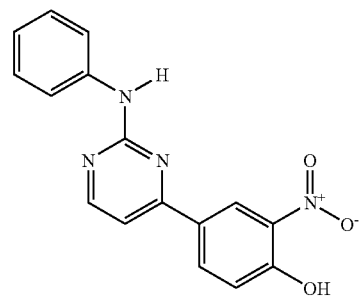
II-119
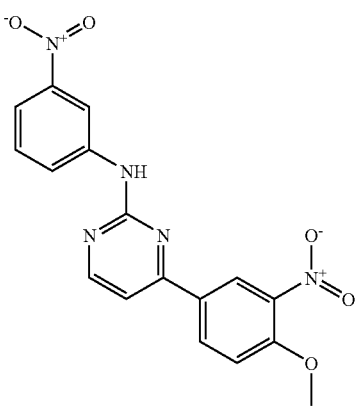
II-120

TABLE 1-continued
Examples of Compounds of Formula II:
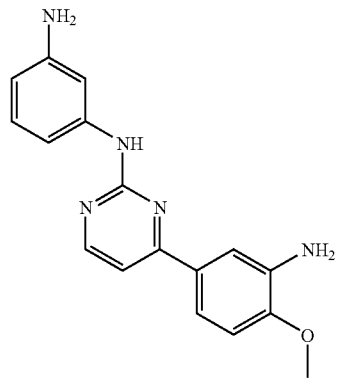
II-121
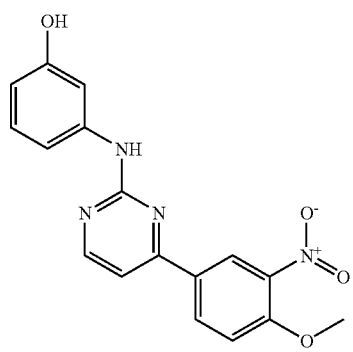
II-122
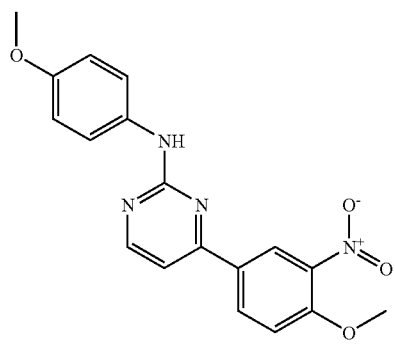
II-123
TABLE 1-continued
Examples of Compounds of Formula II:
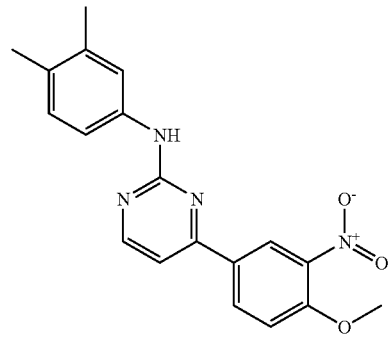
II-124
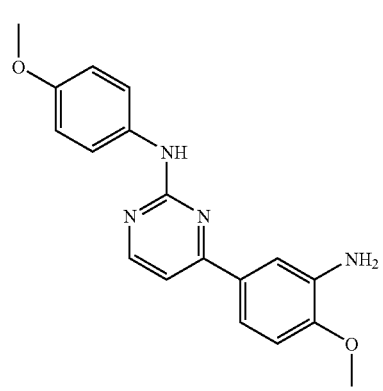
II-125
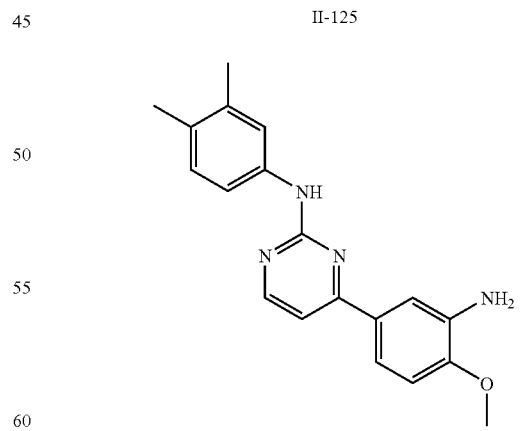
II-126

TABLE 1-continued
Examples of Compounds of Formula II:
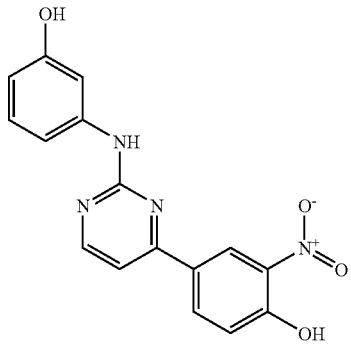
II-127
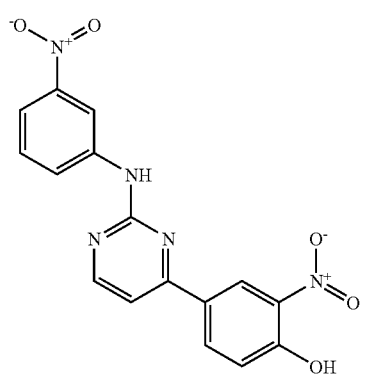
II-128
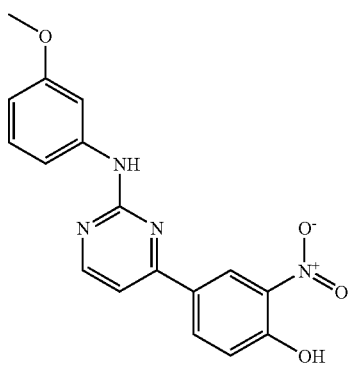
II-129
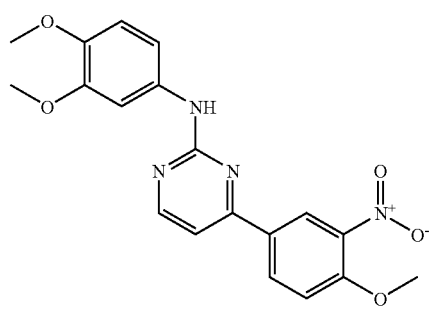
II-130
TABLE 1-continued
Examples of Compounds of Formula II:
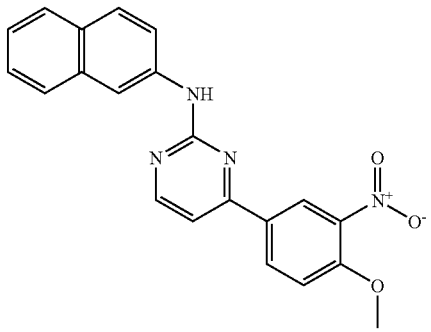
II-131
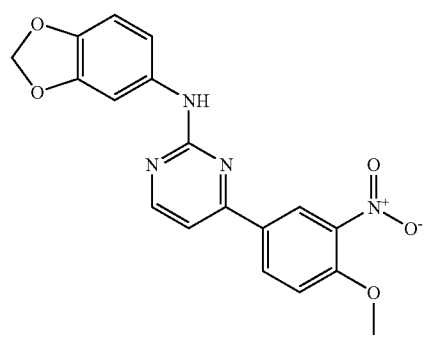
II-132
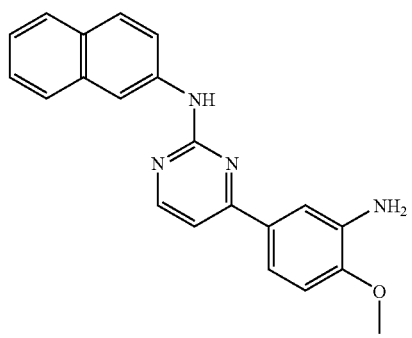
II-133
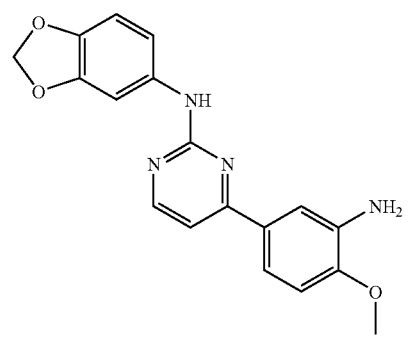
II-134

TABLE 1-continued
Examples of Compounds of Formula II:
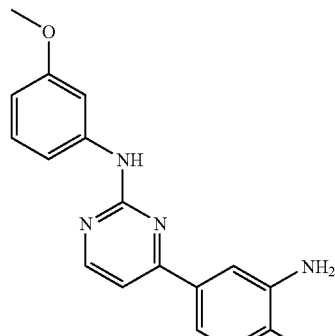
II-135
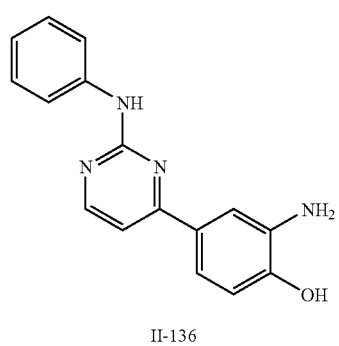
II-136
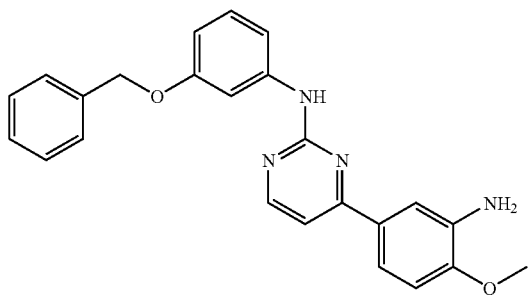
II-137
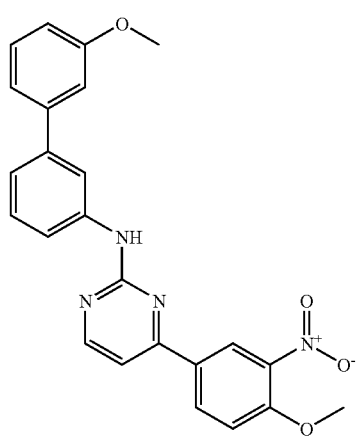
II-138
TABLE 1-continued
Examples of Compounds of Formula II:
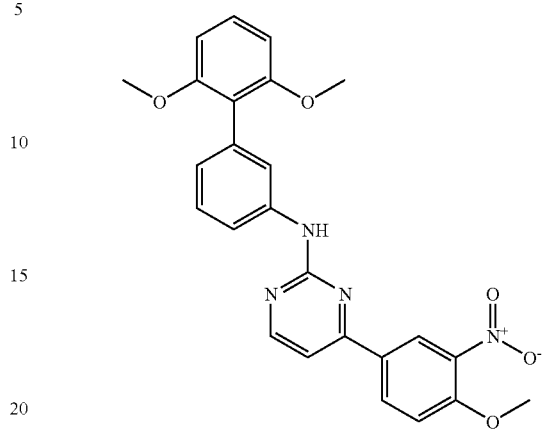
II-139
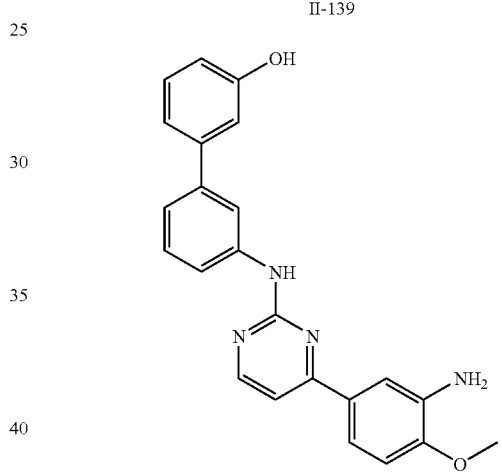
II-140
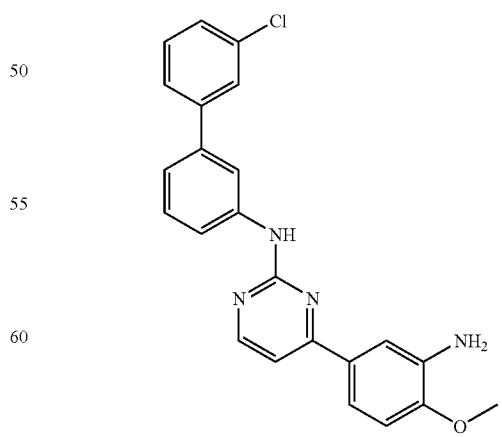
II-141

TABLE 1-continued
Examples of Compounds of Formula II:
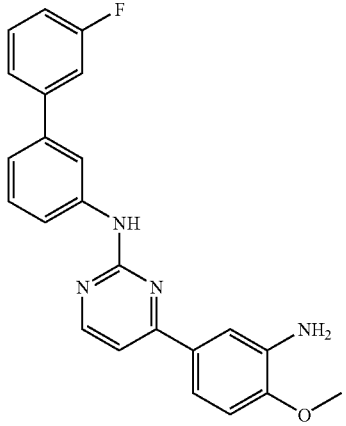
II-142
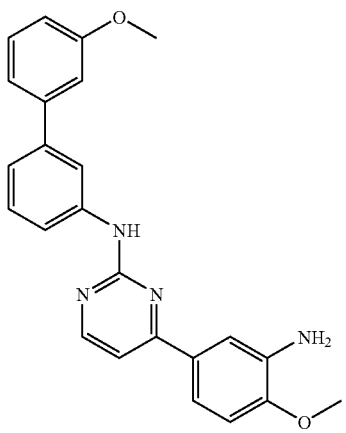
II-143
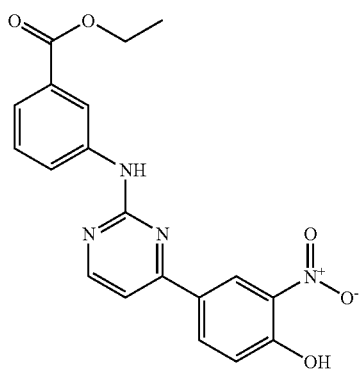
II-144
TABLE 1-continued
Examples of Compounds of Formula II:
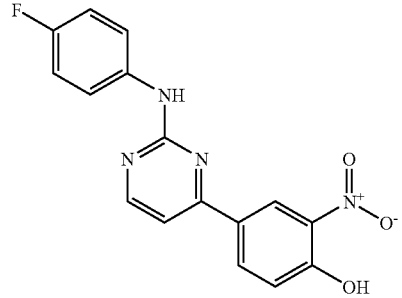
II-145
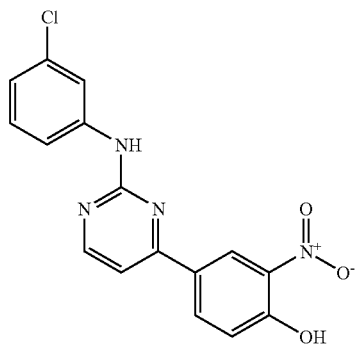
II-146
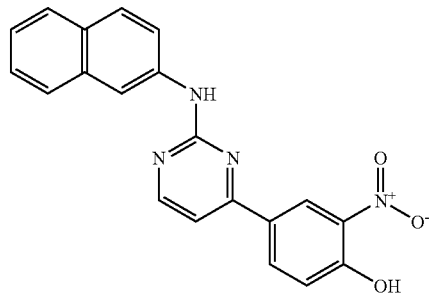
II-147
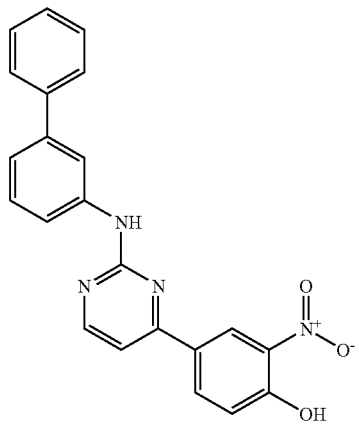
II-148

TABLE 1-continued
Examples of Compounds of Formula II:
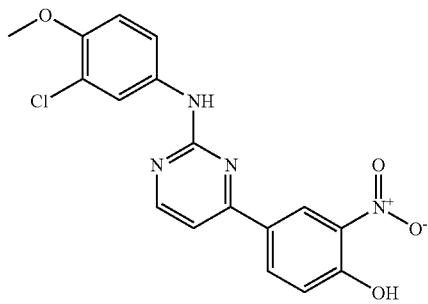
II-149
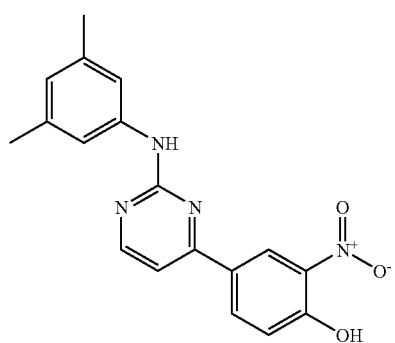
II-150
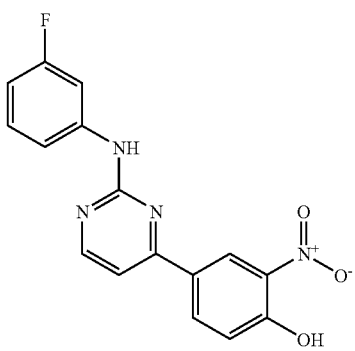
II-151
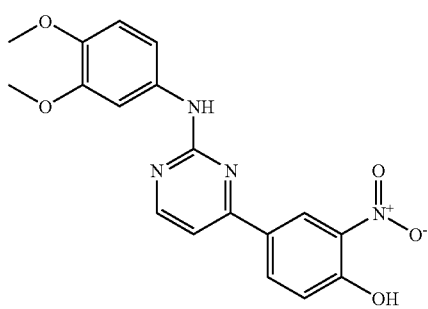
II-152
TABLE 1-continued
Examples of Compounds of Formula II:
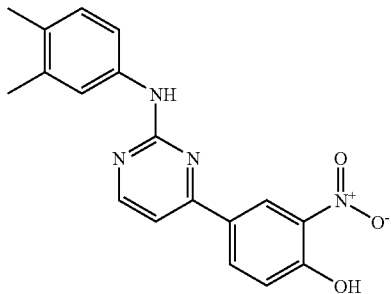
II-153
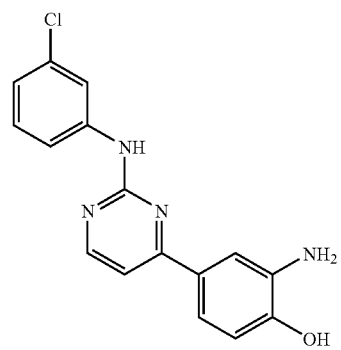
II-154
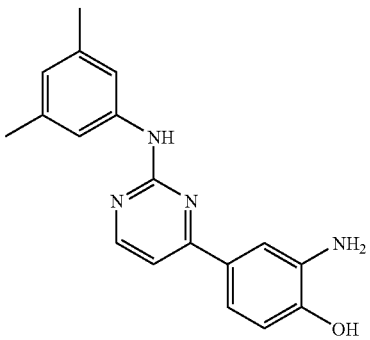
II-155
TABLE 2
Examples of Compounds of Formula III:
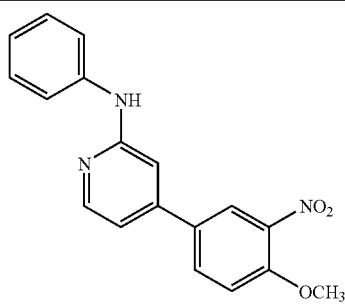
III-1

TABLE 2-continued
Examples of Compounds of Formula III:
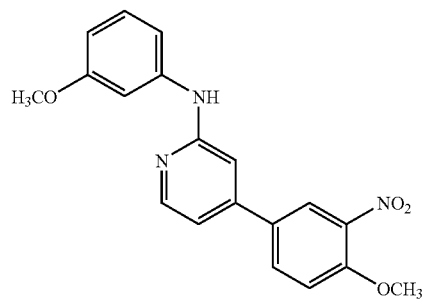
III-2
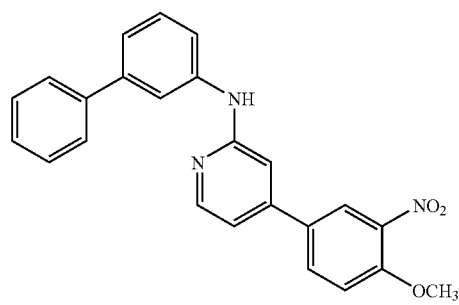
III-3
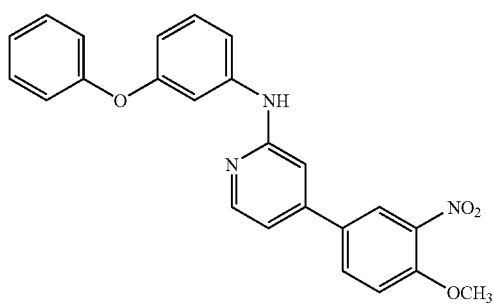
III-4
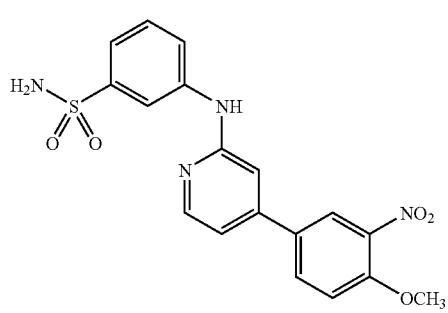
III-5
TABLE 2-continued
Examples of Compounds of Formula III:
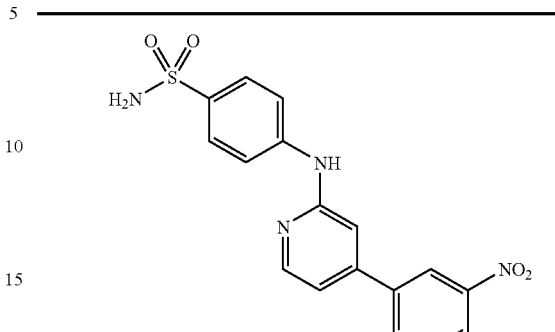
III-6
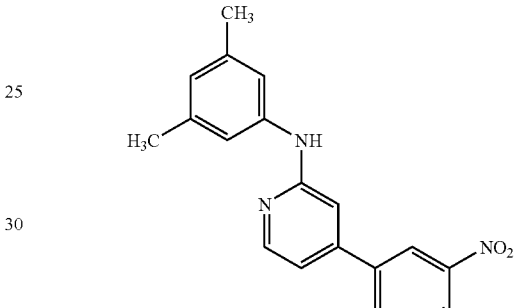
III-7
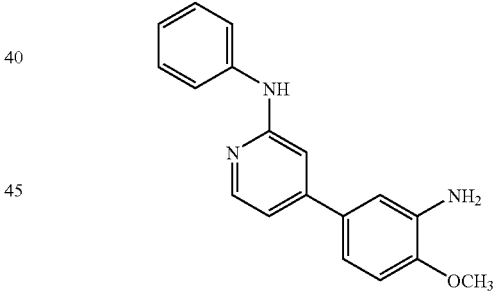
III-8
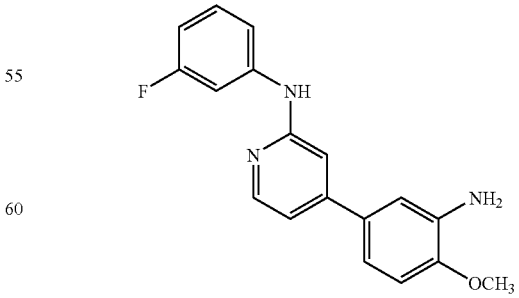
III-9

TABLE 2-continued
Examples of Compounds of Formula III:
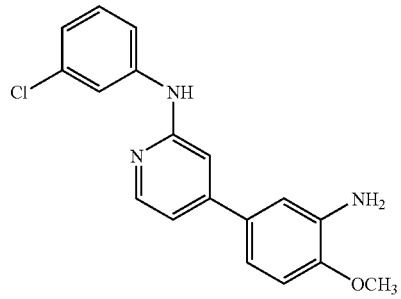
III-10
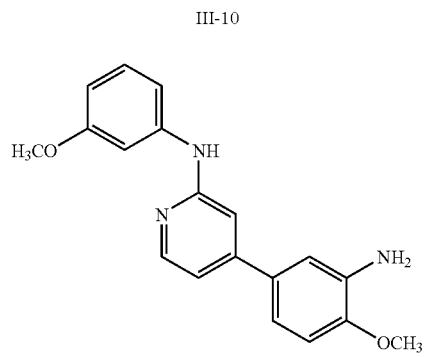
III-11
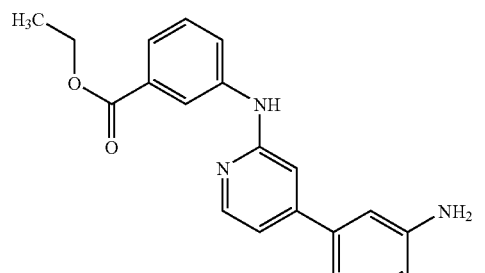
III-12
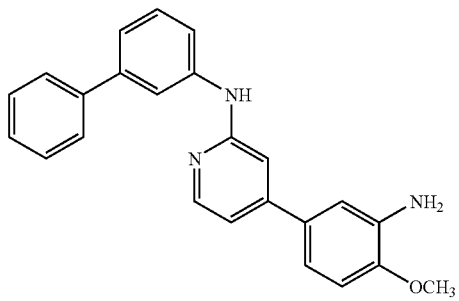
III-13
TABLE 2-continued
Examples of Compounds of Formula III:
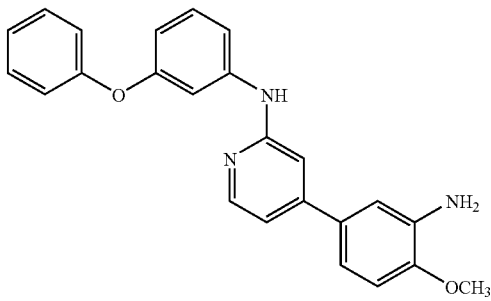
III-14
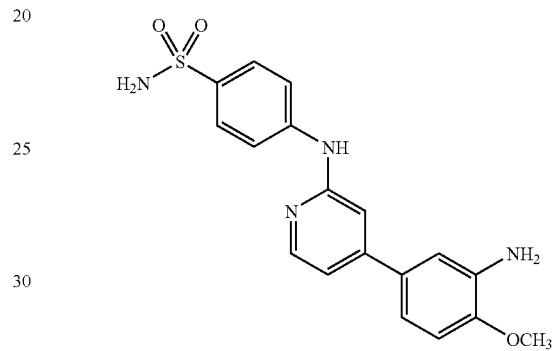
III-15
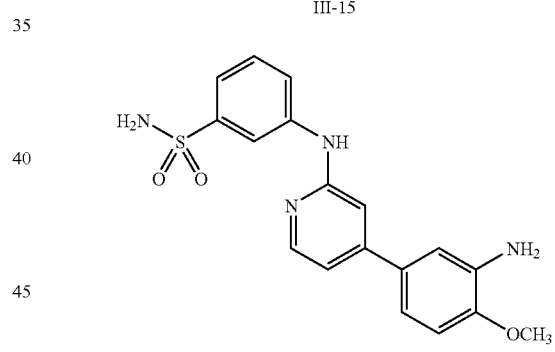
III-16
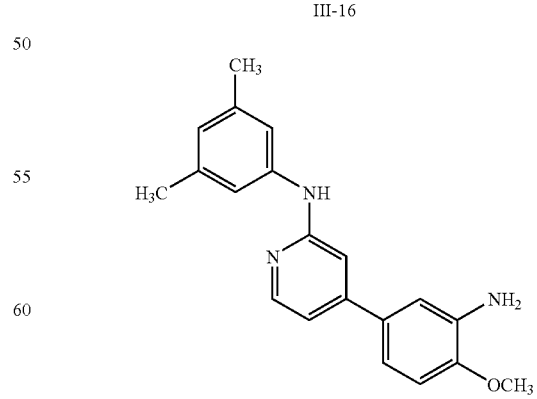
III-17

TABLE 2-continued
Examples of Compounds of Formula III:
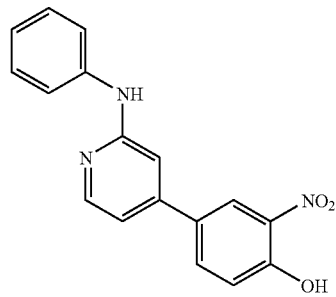
III-18
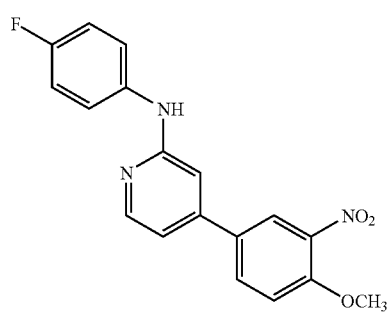
III-19
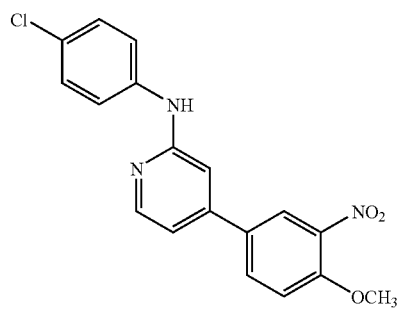
III-20
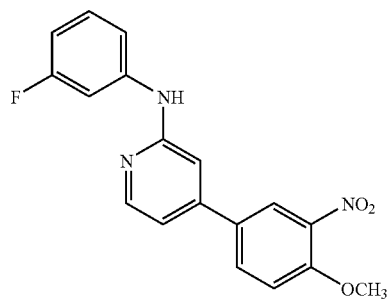
III-21
TABLE 2-continued
Examples of Compounds of Formula III:
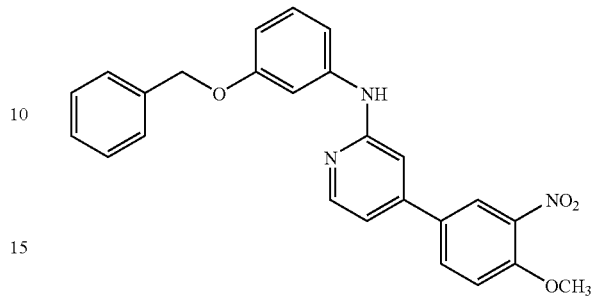
III-22
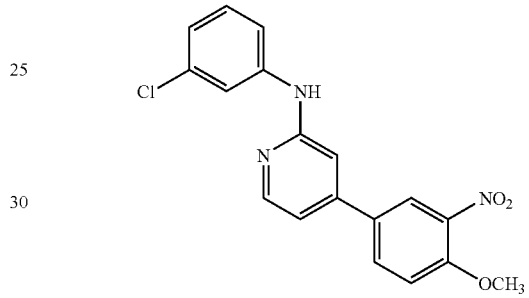
III-23
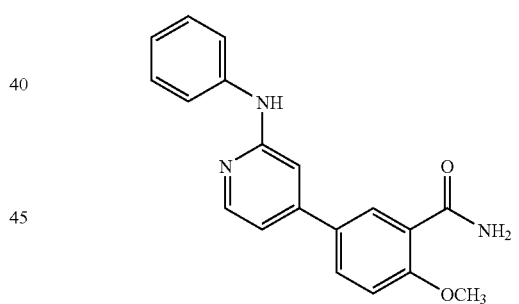
III-24
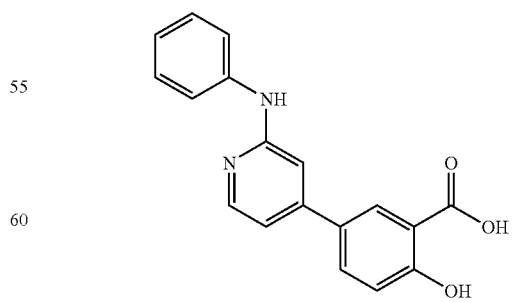
III-25

TABLE 2-continued
Examples of Compounds of Formula III:
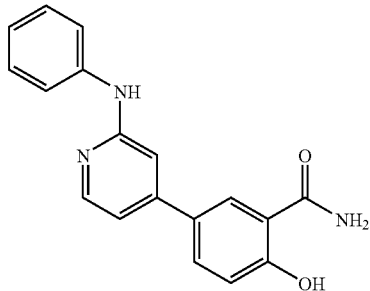
III-26
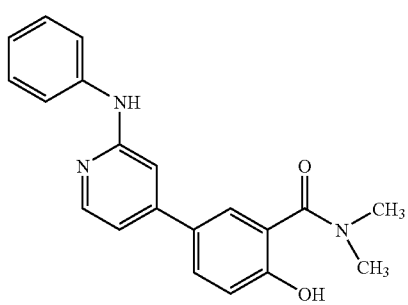
III-27
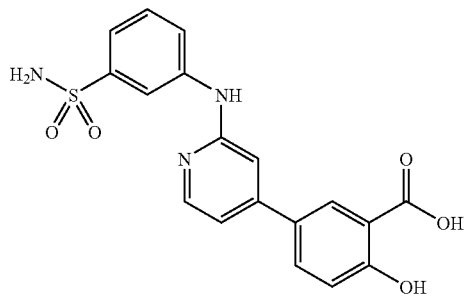
III-28
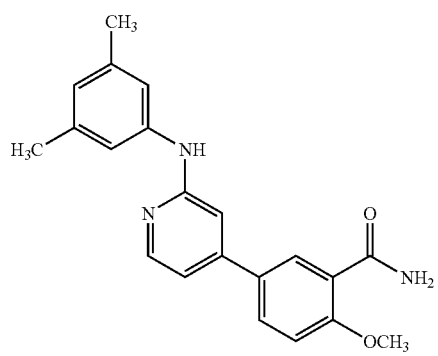
III-29
TABLE 2-continued
Examples of Compounds of Formula III:
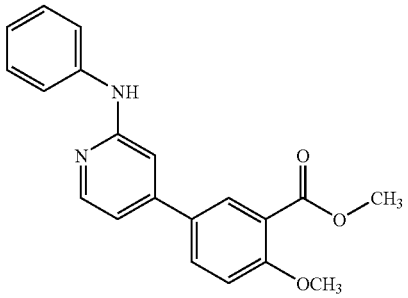
III-30
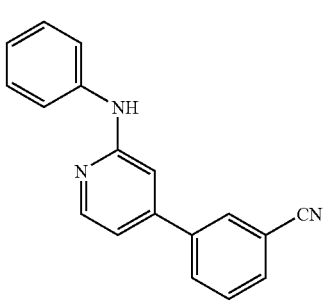
III-31
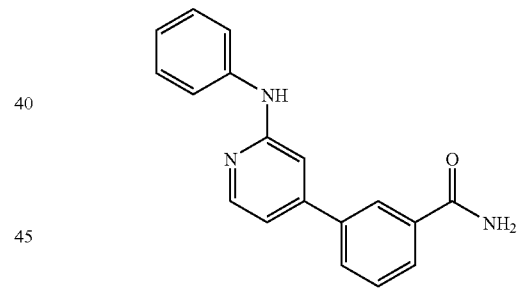
III-32
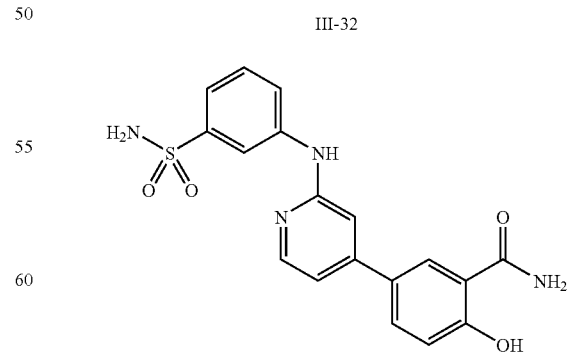
III-33

TABLE 2-continued

Examples of Compounds of Formula III:

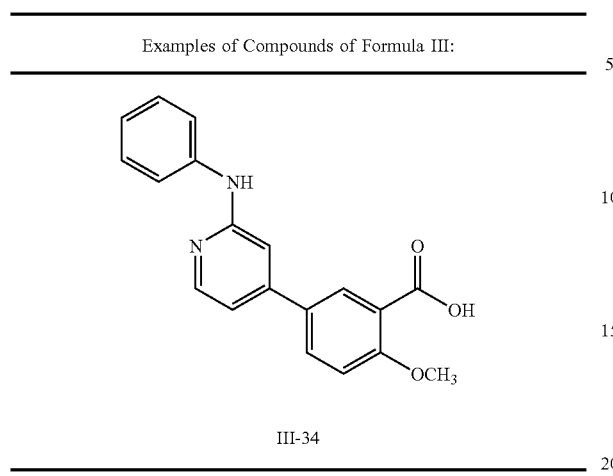

III-34

4. General Synthetic Methodology

The compounds of this invention may be prepared in general by methods known to those skilled in the art for analogous compounds, as illustrated by Schemes 1, 2 and 3 below, and the preparative examples that follow.

Schemes 1, 2 and 3 below depict generally the synthesis of certain exemplary compounds of the invention. Specifically, Scheme 1 depicts the synthesis of compounds where $R^3$ is COOH or $CON(R)_2$ and $R^4$ is OH. Scheme 2 depicts compounds where $R^3$ is $NO_2$ or $N(R)_2$ and $R^4$ is OR'. Scheme 3 depicts compounds where $R^3$ is $CON(R)_2$ and $R^4$ is OR'. It will be appreciated that additional compounds where $R^3$ is defined generally and in subsets herein can be prepared according to the general methods described above and methods known in the art using the appropriate starting materials.

Scheme 1:

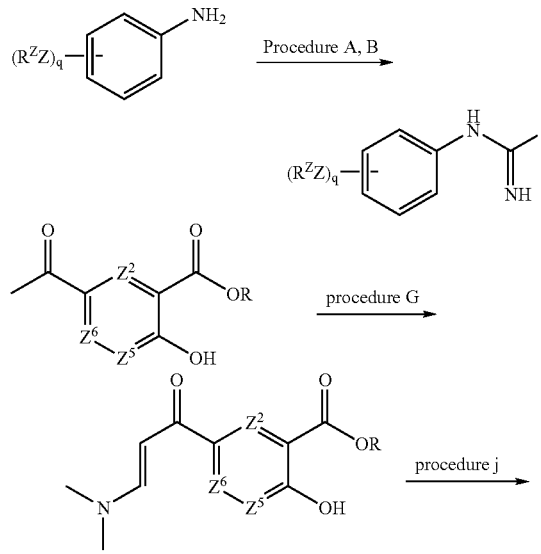

-continued

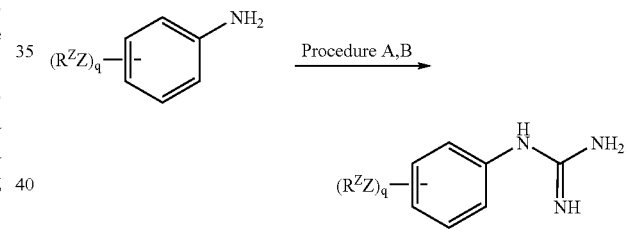

Scheme 2:

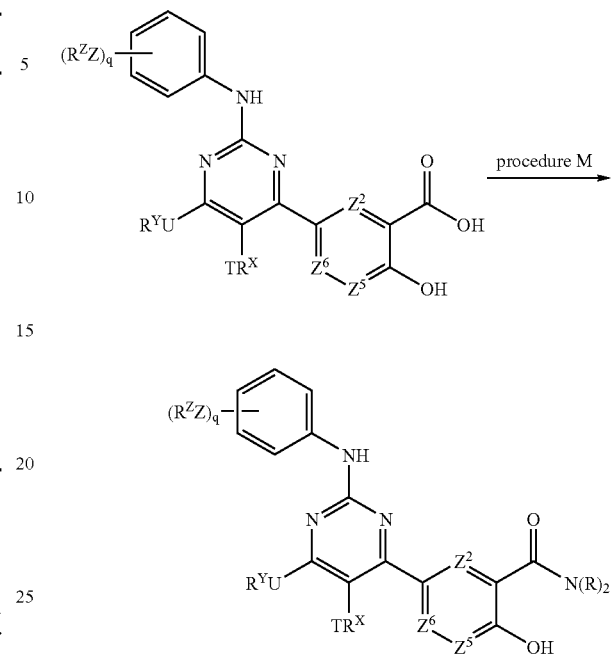

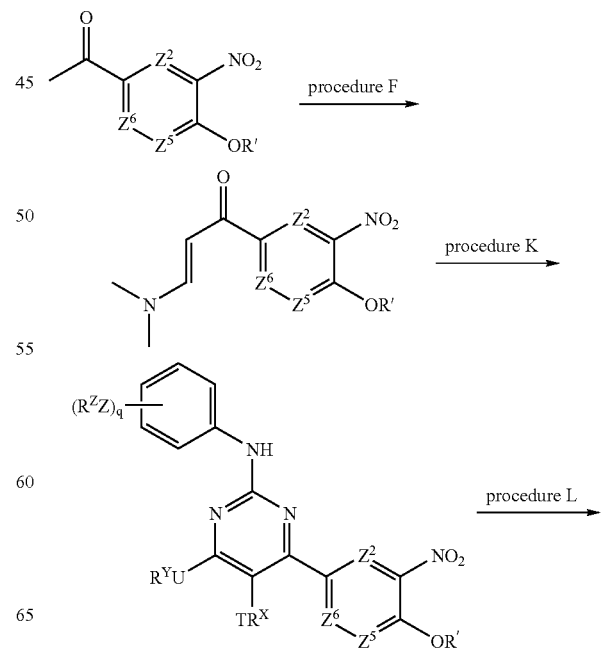

-continued

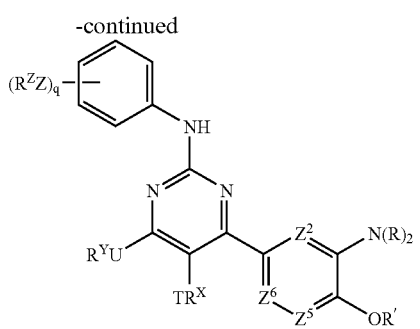

Scheme 3:

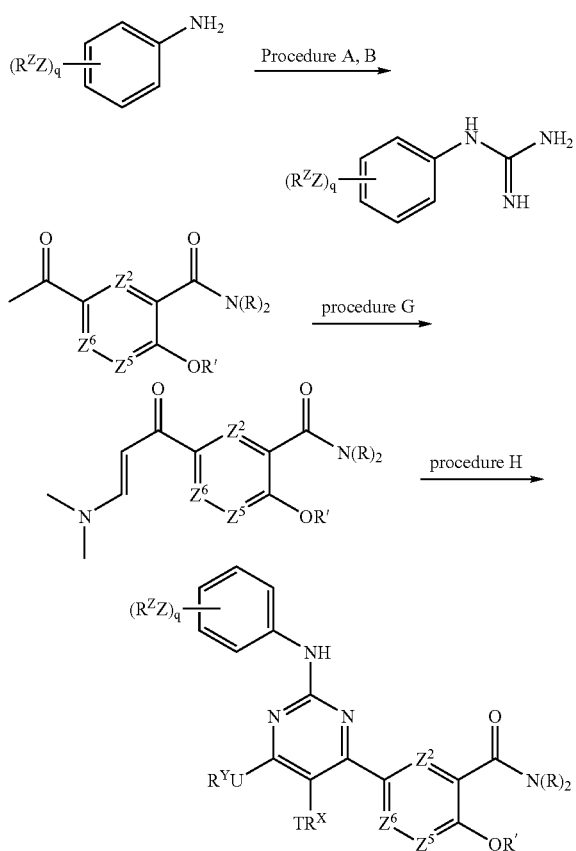

5. Uses, Formulation and Administration

Pharmaceutically Acceptable Compositions

As discussed above, the present invention provides compounds that are inhibitors of protein kinases, and thus the present compounds are useful for the treatment of diseases, disorders, and conditions including, but not limited to a proliferative disorder, a cardiac disorder, a neurodegenerative disorder, psychotic disorders, an autoimmune disorder, a condition associated with organ transplant, an inflammatory disorder, an immunologically mediated disorder, a viral disease, or a bone disorder. In preferred embodiments, the compounds are useful for the treatment of allergy, asthma, diabetes, Alzheimer's disease, Huntington's disease, Parkinson's disease, AIDS-associated dementia, amyotrophic lateral sclerosis (AML, Lou Gehrig's disease), multiple sclerosis (MS), schizophrenia, cardiomyocyte hypertrophy, reperfusion/ischemia (e.g., stroke), baldness, cancer, hepatomegaly, cardiovascular disease including cardiomegaly, cystic fibrosis, viral disease, autoimmune diseases, atherosclerosis, restenosis, psoriasis, inflammation, hypertension, angina pectoris, cerebrovascular contraction, peripheral circulation disorder, premature birth, arteriosclerosis, vasospasm (cerebral vasospasm, coronary vasospasm), retinopathy, erectile dysfunction (ED), AIDS, osteoporosis, Crohn's Disease and colitis, neurite outgrowth, and Raynaud's Disease. In preferred embodiments, the disease, condition, or disorder is atherosclerosis, hypertension, erectile dysfunction (ED), reperfusion/ischemia (e.g., stroke), or vasospasm (cerebral vasospasm and coronary vasospasm).

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a JAK-3, JNK-3, CDK-2, SYK, or GSK-3 kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+$ $(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder. The compounds and compositions, according to the method of the present invention, may be administered using any amount and any route of administration effective for treating or lessening the severity of a proliferative disorder, a cardiac disorder, a neurodegenerative disorder, an autoimmune disorder, a condition associated with organ transplant, an inflammatory disorder, an immunologically mediated disorder, a viral disease, or a bone disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs.

In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of JAK-3, JNK-3, CDK-2, SYK, or GSK-3, and thus, without wishing to be bound by any particular theory, the compounds and compositions are particularly useful for treating or lessening the severity of a disease, condition, or disorder where activation of one or more of JAK-3, JNK-3, CDK-2, SYK, or GSK-3 is implicated in the disease, condition, or disorder. When activation of JAK-3, JNK-3, CDK-2, SYK, or GSK-3 is implicated in a particular disease, condition, or disorder, the disease, condition, or disorder may also be referred to as "JAK-3, JNK-3, CDK-2, SYK, or GSK-3-mediated disease" or disease symptom. Accordingly, in another aspect, the present invention provides a method for treating or lessening the severity of a disease, condition, or disorder where activation or one or more of JAK-3, JNK-3, CDK-2, SYK, or GSK-3 is implicated in the disease state.

The activity of a compound utilized in this invention as an inhibitor of JAK-3, JNK-3, CDK-2, SYK, or GSK-3, may be assayed in vitro, in vivo or in a cell line. In vitro assays include assays that determine inhibition of either the phosphorylation activity or ATPase activity of activated JAK-3, JNK-3, CDK-2, SYK, or GSK-3. Alternate in vitro assays quantitate the ability of the inhibitor to bind to JAK-3, JNK-3, CDK-2, SYK, or GSK-3. Inhibitor binding may be measured by radiolabelling the inhibitor prior to binding, isolating the inhibitor/JAK-3, inhibitor/JNK-3, inhibitor/CDK-2, inhibitor/GSK-3, or inhibitor/SYK complex and determining the amount of radiolabel bound. Alternatively, inhibitor binding may be determined by running a competition experiment where new inhibitors are incubated with JAK-3, JNK-3, CDK-2, SYK, or GSK-3 bound to known radioligands.

The term "measurably inhibit", as used herein means a measurable change in JAK-3, JNK-3, CDK-2, SYK, or GSK-3 activity between a sample comprising said composition and a JAK-3, JNK-3, CDK-2, SYK, or GSK-3 kinase and an equivalent sample comprising JAK-3, JNK-3, CDK-2, SYK, or GSK-3 kinase in the absence of said composition.

The term "JAK-mediated disease", as used herein means any disease or other deleterious condition in which a JAK family kinase is known to play a role. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas.

According to another embodiment, the invention provides a method for treating or lessening the severity of a CDK2-mediated disease or condition in a patient comprising the step of administering to said patient a composition according to the present invention.

The term "CDK2-mediated disease", as used herein means any disease or other deleterious condition in which CDK2 is known to play a role. Accordingly, these compounds are useful for treating diseases or conditions that are known to be affected by the activity of CDK2 kinase. Such diseases or conditions include cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis, viral infections, neurodegenerative disorders, disorders associated with thymocyte apoptosis, or proliferative disorders resulting from the deregulation of the cell cycle, especially of the progression from $G_1$ to S phase.

According to another embodiment, the invention provides a method for treating or lessening the severity of a CDK2-mediated disease or condition in a patient comprising the step of administering to said patient a composition according to the present invention.

The term "JNK-mediated condition", as used herein means any disease or other deleterious condition in which INK is known to play a role. Such conditions include, without limitation, inflammatory diseases, autoimmune diseases, destructive bone disorders, proliferative disorders, cancer, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2.

"JNK-mediated conditions" also include ischemia/reperfusion in stroke, heart attacks, myocardial ischemia, organ hypoxia, vascular hyperplasia, cardiac hypertrophy, hepatic ischemia, liver disease, congestive heart failure, pathologic immune responses such as that caused by T cell activation and thrombin-induced platelet aggregation.

In addition, JNK inhibitors of the instant invention may be capable of inhibiting the expression of inducible pro-inflammatory proteins. Therefore, other "JNK-mediated conditions" which may be treated by the compounds of this invention include edema, analgesia, fever and pain, such as neuromuscular pain, headache, cancer pain, dental pain and arthritis pain.

According to another embodiment, the invention provides a method for treating or lessening the severity of a GSK3-mediated disease or condition in a patient comprising the step of administering to said patient a composition according to the present invention.

The term "GSK3-mediated disease" or "GSK3-mediated condition", as used herein, means any disease or other deleterious condition in which GSK3 protein kinase is known to play a role. Such conditions include, without limitation, diabetes, neurodegenerative disorders, Alzheimer's disease, Huntington's, Parkinson's, AIDS associated dementia, amyotrophic lateral sclerosis (AML), multiple sclerosis (MS), schizophrenia, stroke, cardiomycete hypertrophy, and baldness.

According to another embodiment, the invention provides a method for treating or lessening the severity of a Syk-mediated disease or condition in a patient comprising the step of administering to said patient a composition according to the present invention.

The term "Syk-mediated disease" or "Syk-mediated condition", as used herein, means any disease or other deleterious condition in which Syk protein kinase is known to play a role. Such conditions include, without limitation, allergic disorders, especially asthma.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http:/Hwww.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting JAK-3, JNK-3, CDK-2, SYK, or GSK-3 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of JAK-3, JNK-3, CDK-2, SYK, or GSK-3 kinase activity in a biological sample is useful for a variety of purposes that are known to one of skill in the art. Examples of such purposes include, but are not limited to, blood transfusion, organ-transplantation, biological specimen storage, and biological assays.

In order that the invention described herein may be more fully understood, the following examples are set forth. It should be understood that these examples are for illustrative purposes only and are not to be construed as limiting this invention in any manner.

EXAMPLES

Scheme I above depicts the synthesis of several exemplary compounds. The examples below describe general procedures for the preparation of compounds herein (as shown in Schemes 1, 2 and 3 above) and Table 3 depicts characterization for exemplary compounds of the invention.

Preparation of Guanidines.

Procedure A: General Procedure for the Synthesis of Guanidines

The substituted aniline (20 mmol, 2 eq.) and cyanamide (10 mmol, 1 eq.) were taken up in Toluene (5 ml), and Triflic acid (1 ml). The reaction was sealed and heated to 85 C, overnight, with magnetic stirring. The reaction was quenched with water (10 ml). The phases were separated and the aqueous was made basic with 2N sodium hydroxide (10 ml). The basic aqueous phase was washed with toluene and then extracted with methylene chloride (3×) to give desired guanidine upon concentration.

Procedure B: General Procedure for the Synthesis of Guanidines

In a tube was placed cyanamide (10 mmol, 1 eq.) and substituted aniline (11 mmol, 1.1 eq). To this was added 10 ml of dioxane (alternatively ethylene glycol dimethyl ether, DME, can be used), and the mixture was warmed to achieve dissolution. To the homogeneous solution was added 4N hydrochloric acid in dioxane (3 ml, 12 mmol, 1.2 eq.). The tube was sealed and heated to 60 C overnight with magnetic stirring. The reaction was concentrated to dryness, basified with 2N NaOH, and extracted with methylene chloride (2×). The organics were concentraded to give desired guanidine.

Procedure B (Modified): General Procedure for the Synthesis of Guanidines

The substituted aniline (20 mmol) and cyanamide (20 mmol) were dissolved in dioxane (25 ml) with warming. To this was added 4N hydrochloric acid in dioxane (5 ml, 20 mmol) dropwise via syringe. The reaction was heated to reflux for three days, concentrated to dryness and dissolved in ethanol. To this was added 2N sodium hydroxide (10 ml, 20 mmol) resulting in a voluminous precipitate. The solid was filtered and washed with ether/ethanol, and then dried in-vacuo to give the desired guanidine with 1 equivalent of sodium chloride.

Procedure D: Procedure for the Synthesis of N-methylated Benzoxazin Eneaminones

The compound 6-acetyl-2H-1,4-benzoxazin-3(4H)-one (10 mmol) was taken up in excess N,N-dimethylformamide dimethyl acetal and heated to 80 C, overnight. The reaction was concentrated to dryness and used without purification.

Procedure E: General Procedure for the Synthesis of N-alkylated Benzoxazin Acetophenones The compound 6-acetyl-2H-1,4-benzoxazin-3(4H)-one (10 mmol) and alkylating agent (5.4 mmol, 1.1 eq.) were taken up in dimethylformamide (10 ml) with powdered potassium carbonate (36 mmol, xs). The reaction was heated to approximately 110 C for 1.5 to 24 hours. The reaction is quenched with water and extracted with ether (2×). The organics were washed with brine, dried over sodium sulfate, filtered, and concentrated to give crude. The crude was purified via flash chromatography on silica gel, and eluted with ether or ethyl acetate).

Procedure F: General Procedure for the Synthesis of Eneaminones

The appropriate acetophenone was taken up in N,N-Dimethylformamide dimethyl acetal neat (alternatively toluene may be used as co-solvent), and heated to 95 C for 1 to 3 days. Alternatively, toluene may be added to aid dissolution. The reaction was then concentrated to an oil. The product occasionally crystallized from ethyl acetate, or from ethyl acetate/hexane. Otherwise, it was purified via column chromatography on silica gel, eluted with ethyl acetate/hexane to pure ethyl acetate.

Procedure G: General Procedure for the Synthesis of Eneaminones

The appropriate acetophenone (20 mmol) was dissolved in 100 ml of toluene (alternatively N,N-dimethylformamide or tetrahydrofuran may be used as solvent) and treated with tert-Butoxybis (dimethylamino) methane (Bredereck's reagent, 35 mmol, 1.75 eq.). The reaction was heated to reflux overnight. Upon concentration a precipitate forms, which was filtered, and used directly. Alternatively, the crude may be purified via flash chromatography on silica gel, eluted with ethyl acetate/hexane or acetone/hexane.

Procedure H: General Procedure for the Synthesis of Phenylaminopyrimidines

The eneaminone (200 umol) and guanidine (300 umol to 500 umol, 1.5 to 2.5 eq.) were dissolved in acetonitrile (200 uL to 500 uL).The reaction was sealed and heated to approximately 80 C, overnight. The reaction was extracted with ethyl acetate and water. The organics were washed with brine, dried over sodium sulfate, filtered, and concentrated to crude. The crude was either recrystallized from ethyl acetate, ethyl acetate/hexane, ether, or ether/hexane. Otherwise, the crude was purified via flash chromatography on silica gel, eluted with ethyl acetate/hexane or ethyl acetate.

Procedure J: General Procedure for the Synthesis of Phenylaminopyrimidines

The eneaminone (200 umol) and guanidine (300 umol to 500 umol, 1.5 to 2.5 eq.) was dissolved in approximately 1 ml of dimethylformamide (alternatively, DMSO). The reaction was sealed and heated to approximately 120 C, overnight. The product can either be precipitated via addition of ethyl acetate and 1N hydrochloric acid, or purified via reverse phase HPLC using a C18 column and eluted with an acetonitrile/water (with 0.1% trifluoroacetic acid v/v) gradient.

Procedure J (Modified): General Procedure for the Synthesis of Phenylaminopyrimidines As per general procedure J except for the addition of powdered potassium carbonate (1 equivalent) or excess.

Procedure K: General Procedure for the Preparation of Phenylaminopyrimidines

The eneaminone (400 umol) and guanidine (400 umol, 1 eq.) were dissolved in absolute ethanol (2 ml). The reaction was sealed and heated for up to 7 days. The resultant product can either be filtered or purified via silica gel chromatography and eluted with ethyl acetate/hexanes, ethyl acetate, or acetone. Otherwise, reverse phase HPLC on C18 utilizing a gradient of acetonitrile/water with 0.1% TFA may be employed.

Procedure L: General Procedure for the Reduction of Nitrobenzenes to Anilines

The nitrobenzene (100 to 200 umol) was dissolved in DMF(3 ml), in a tube. To this was added methanol (1 ml), iron powder (200 mg to 300 mg, excess), and saturated aqueous sodium bicarbonate (0.25 to 0.5 ml). The tube was sealed and heated to 96 C, overnight. The reactions were cooled, filtered, and concentrated to give crude product. The products were purified on silica gel eluted with ethyl acetate/hexanes with 1% triethylamine, or via reverse phase HPLC on C18 eluted with acetonitrile/water with 0.1% TFA.

Procedure M: General Procedure for Amide Couplings from Carboxylic Acids

The carboxylic acid (100 to 200 umol) was placed in a tube with EDC (110 to 400 umol, 1.1 to 2 equivalents), HOBT (40 to 200 umol, 0.4 to 1 equivalent), DMF (1 to 3 ml), and N-methylmorpholine (250 to 500 ul). To this mixture was added desired amine or aminehydrochloride salt (300 to 600 umol, 3 to 6 equivalents). The reaction was sealed and heated to 122 C, overnight. The reaction was then concentrated to dryness and extracted with ethyl acetate/water. The organic layer was dried over sodium sulfate, filtered and concentrated to give crude product. The product was purified via silica gel chromatography eluted with ethyl acetate/hexanes, ethyl acetate or acetone.

Procedure N: General Procedure for Hydrolysis of Esters

The ester (100 to 200 umol) was dissolved in DMF (1 to 3 ml). To this was added 1N sodium hydroxide (2 to 5 equivalents). The reaction was warmed to 50 C several hours until complete. The reaction was quenched with 1N hydrochloric acid (2 to 5 equivalents). The resulting product was filtered and dried in vacuo with warming.

| Compound | Procedures | M + 1 | M − 1 | MW |
|---|---|---|---|---|
| II-18 | BFJ | 309 | | 308 |
| II-1 | BFK | 323 | | 322 |
| II-21 | AFK | 341 | | 340 |
| II-19 | BFK | 357 | | 356 |
| II-2 | BFK | 353 | | 352 |
| II-3 | BFK | 399 | | 398 |
| II-4 | BFK | 415 | | 414 |
| II-5 | BFK | 402 | 400 | 401 |
| II-6 | BFK | 402 | 400 | 401 |
| II-7 | BFK | 351 | | 350 |
| II-8 | BFKL | 293 | | 292 |
| II-9 | AFKL | 311 | 309 | 310 |
| II-10 | BFKL | 327 | 325 | 326 |
| II-11 | BFKL | 323 | | 322 |
| II-12 | XFKL | 365 | | 364 |
| II-13 | BFKL | 369 | | 368 |
| II-14 | BFKL | 385 | | 384 |
| II-16 | BFKL | 372 | | 371 |
| II-15 | BFKL | 372 | 370 | 371 |
| II-17 | BFKL | 321 | | 320 |
| II-24 | BGH | 321 | | 320 |
| II-25 | BGj | 308 | 306 | 307 |
| II-31 | BFJ | 273 | | 272 |
| II-26 | BGjM | 307 | 305 | 306 |
| II-27 | BGjM | 335 | | 334 |
| II-28 | BGjM | 387 | 385 | 386 |
| II-29 | BGHM | 349 | | 348 |
| II-33 | bGJM | 386 | 384 | 385 |
| II-32 | BFj | 291 | | 290 |
| II-30 | BFJ | 336 | | 335 |
| II-34 | BFJN | 322 | 320 | 321 |

"X" indicates the absence of a procedure and lower case letters indicate the use of the modified procedures.

Example 2

JAK3 Inhibition Assay

Compound inhibition of JAK was assayed by the method described by G. R. Brown, et al, *Bioorg. Med. Chem. Lett.* 2000, vol. 10, pp 575-579 in the following manner. Into Maxisorb plates, previously coated at 4° C. with Poly (Glu, Ala, Tyr) 6:3:1 then washed with phosphate buffered saline 0.05% and Tween (PBST), was added 2 µM ATP, 5 mM $MgCl_2$, and a solution of compound in DMSO. The reaction was started with JAK enzyme and the plates incubated for 60 minutes at 30° C. The plates were then washed with PBST, 100 µL HRP-Conjugated 4G10 antibody was added, and the plate incubated for 90 minutes at 30° C. The plate was again washed with PBST, 100 µL TMB solution is added, and the plates were incubated for another 30 minutes at 30° C. Sulfuric acid (100 µL of 1M) was added to stop the reaction and the plate is read at 450 nm to obtain the optical densities for analysis to determine $K_i$ values.

The compound numbers correspond to the compound numbers in Table 1 and compounds were tested and found to inhibit JAK-3. Certain compounds described herein were shown to have $K_i$s less than 0.1 micromolar (µM).

Example 3

CDK2 Inhibition Assay

Compounds were screened for their ability to inhibit CDK-2/Cyclin A using a standard coupled enzyme assay (Fox et al (1998) *Protein Sci* 7, 2249). Reactions were carried out in 100 mM HEPES pH 7.5, 10 mM MgCl2, 25 mM NaCl, 1 mM DTT and 1.5% DMSO. Final substrate concentrations in the assay were 100 µM ATP (Sigma chemicals) and 100 µM peptide (American Peptide, Sunnyvale, Calif.). Assays were carried out at 30° C. and 25 nM CDK-2/Cyclin A. Final concentrations of the components of the coupled enzyme system were 2.5 mM phosphoenolpyruvate, 350 µM NADH, 30 µg/ml pyruvate kinase and 10 µg/ml lactate dehydrogenase.

An assay stock buffer solution was prepared containing all of the reagents listed above, with the exception of CDK-2/Cyclin A, DTT and the test compound of interest. 56 µl of the test reaction was placed in a 384 well plate followed by addition of 1 µl of 2 mM DMSO stock containing the test compound (final compound concentration 30 µM). The plate was preincubated for ~10 minutes at 30° C. and the reaction initiated by addition of 10 µl of enzyme (final concentration 25 nM). Rates of reaction were obtained using a BioRad Ultramark plate reader (Hercules, Calif.) over a 5 minute read time at 30° C. and $K_i$s were determined using standard methods.

The compound numbers correspond to the compound numbers in Table 1 and compounds were tested and found to inhibit CDK-2 Certain compounds described herein were shown to have $K_i$s less than 0.1 micromolar (µM).

Example 4

JNK3 Inhibition Assays

Compounds were assayed for the inhibition of JNK3 by a spectrophotometric coupled-enzyme assay. In this assay, a fixed concentration of activated JNK3 (10 nM) was incubated with various concentrations of a potential inhibitor dissolved in DMSO for 10 minutes at 30° C. in a buffer containing 0.1 M HEPES buffer, pH 7.5, containing 10 mM $MgCl_2$, 2.5 mM phosphoenolpyruvate, 200 µM NADH, 150 µg/mL pyruvate kinase, 50 µg/mL lactate dehydrogenase, and 200 µM EGF receptor peptide. The reaction was initiated by the addition of 10 µM ATP and the assay plate is inserted into the spectrophotometer's assay plate compartment that was maintained at 30° C. The decrease of absorbance at 340 nm was monitored as a function of time. The rate data as a function of inhibitor concentration was fitted to competitive inhibition kinetic model to determine the $K_i$.

The compound numbers correspond to the compound numbers in Table 1 and compounds were tested and found to inhibit JNK-3. Certain compounds described herein were shown to have $K_i$s less than 0.1 micromolar (μM).

Example 6

Syk Inhibition Assay

Compounds were screened for their ability to inhibit Syk using a standard coupled enzyme assay (Fox et al (1998) *Protein Sci* 7, 2249). Reactions were carried out in 100 mM HEPES pH 7.5, 10 mM $MgCl_2$, 25 mM NaCl, 1 mM DTT and 1.5% DMSO. Final substrate concentrations in the assay were 200 μM ATP (Sigma chemical Co.) and 4 μM poly Gly-Tyr peptide (Sigma Chemical Co.). Assays were carried out at 30° C. and 200 nM Syk. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above, with the exception of Syk, DTT and the test compound of interest. 56 μl of the test reaction was placed in a 96 well plate followed by the addition of 1 μl of 2 mM DMSO stock containing the test compound (final compound concentration 30 μM). The plate was preincubated for ~10 minutes at 30° C. and the reaction initiated by the addition of 10 μL of enzyme (final concentration 25 nM). Rates of reaction were obtained using a BioRad Ultramark plate reader (Hercules, Calif.) over a 5 minute read time at 30° C., and $K_i$s were determined using standard methods.

The compound numbers correspond to the compound numbers in Table 1 and were found to inhibit Syk. Certain compounds described herein were shown to have $K_i$s less than 0.1 micromolar (μM).

Example 6

GSK-3 Inhibition Assay

Compounds were screened for their ability to inhibit GSK3-β (AA 1-420) activity using a standard coupled enzyme system (Fox et al. (1998) *Protein Sci.* 7, 2249). Reactions were carried out in a solution containing 100 mM HEPES (pH 7.5), 10 mM $MgCl_2$, 25 mM NaCl, 300 μM NADH, 1 mM DTT and 1.5% DMSO. Final substrate concentrations in the assay were 10 μM ATP (Sigma Chemicals, St Louis, Mo.) and 300 μM peptide (American Peptide, Sunnyvale, Calif.). Reactions were carried out at 30° C. and 60 nM GSK-3β. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of interest. 59 μl of the test reaction was placed in a 96 well ½-diameter plate (Corning, Corning, N.Y.) then treated with 1 μl of a 2 mM DMSO stock containing the test compound (final compound concentration 30 μM). The plate was incubated for ~10 minutes at 30° C. then the reaction initiated by addition of 7 μl of ATP (final concentration 10 μM). Rates of reaction were obtained using a Molecular Devices Spectramax plate reader (Sunnyvale, Calif.) over a 5 minute read time at 30° C., and $K_i$ values were determined using standard methods.

The compound numbers correspond to the compound numbers in Table 1 and were found to inhibit GSK-3. Certain compounds described herein were shown to have $K_i$s less than 0.1 micromolar (μM).

What is claimed is:
1. A compound of formula I:

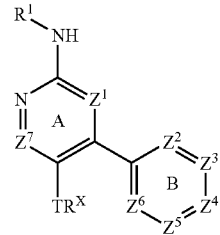

or a pharmaceutically acceptable salt thereof,
wherein:
$R^1$ is a phenyl, cyclohexyl, cyclopentyl, pyridyl, naphthyl, morpholino, piperazinyl, or piperidinyl ring, wherein $R^1$ is optionally substituted with q independent occurrences of $Z-R^Z$; wherein q is 0-5, Z is a bond or is a $C_1$-$C_6$ alkylidene chain wherein up to two methylene units of Z are optionally and independently replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^Z$ is independently selected from R', halogen, $NO_2$, CN, OR', SR', N(R')$_2$, NR'COR', NR'CON(R')$_2$, $NR'CO_2R'$, COR', $CO_2R'$, OCOR', CON(R')$_2$, OCON(R')$_2$, SOR', $SO_2R'$, $SO_2N(R')_2$, $NR'SO_2R'$, $NR'SO_2N(R')_2$, COCOR', or $COCH_2COR'$;
each occurrence of R is independently hydrogen or an optionally substituted $C_{1-6}$ aliphatic group; and each occurrence of R' is independently hydrogen or an optionally substituted $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;
$Z^1$ is N;
$Z^7$ is C—$UR^Y$;
T and U are each independently a bond or a saturated or unsaturated $C_{1-6}$ alkylidene chain, wherein up to two methylene units of the chain are optionally and independently replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR;
$R^X$ and $R^Y$ are each independently halogen, CN, $NO_2$, or R';
$Z^2$, $Z^5$ and $Z^6$ are each independently N or CH, provided that no more than two of $Z^2$, $Z^5$, and $Z^6$ are N;
$Z^3$ is $CR^3$;
$Z^4$ is $CR^4$;
wherein one of $R^3$ or $R^4$ is $R^U$, and the other of $R^3$ or $R^4$ is $R^{V1}$, wherein: $R^U$ is $(CH_2)_tCN$, $(CH_2)_tNO_2$, $(CH_2)_tN(R)_2$, $(CH_2)_tNRC(O)R$, $(CH_2)_tCON(R)_2$, $(CH_2)_tCOOR$, $(CH2)_t$ SO$_2$N(R)$_2$, (CH$_2$)$_t$NRSO$_2$R, (CH$_2$)$_t$NRCON(R)$_2$, (CH$_2$)$_t$NRSO$_2$N(R)$_2$, (CH$_2$)$_t$COCOR, (CH$_2$)$_t$Ar$^2$, wherein t is 0, 1, or 2, and Ar$^2$ is an optionally substituted 5-7 membered saturated, partially unsaturated, or fully unsaturated monocyclic ring having 0-3 heteroatoms independently selected from nitrogen, oxygen, or sulfur; and R$^{V1}$ is OR'.

2. The compound according to claim 1, wherein R$^1$ is an optionally substituted group selected from phenyl, cyclohexyl, or pyridyl.

3. The compound according to claim 1, wherein R$^1$ is optionally substituted phenyl.

4. The compound according to claim 1, wherein each independent occurrence of ZR$^Z$ is halogen, R', CN, NO$_2$, —N(R)(R'), —OR', —SR', —S(O)$_2$N(R)(R'), CO(C$_{1-4}$alkyl), —NRSO$_2$R', COO(C$_{1-4}$alkyl).

5. The compound according to claim 1, wherein q is 1 or 2 and each independent occurrence of ZR$^Z$ is F, Cl, Br, COO(C$_{1-4}$alkyl), C$_{1-4}$alkyl, CN, NO$_2$, —NH$_2$, —OH, C$_{1-4}$alkoxy, —S(O)$_2$NH$_2$, or an optionally substituted benzyloxy, phenyloxy, or phenyl group.

6. The compound according to claim 1, wherein TR$^X$ and UR$^Y$ are each independently selected from hydrogen, halogen, NO$_2$, CN, OR, SR or N(R)$_2$, or C$_{1-4}$aliphatic optionally substituted with oxo, OR, SR, N(R)$_2$, halogen, NO$_2$ or CN.

7. The compound according to claim 1, wherein TR$^X$ and UR$^Y$ groups are each independently hydrogen, Me, OH, OMe or N(R)$_2$.

8. The compound according to claim 1, wherein (T)$_m$R$^X$ and (U)$_n$R$^Y$ are each hydrogen.

9. The compound according to claim 1, wherein ring B is selected from one of the i-viii:

i
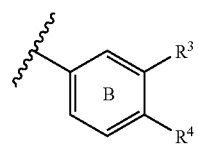

ii
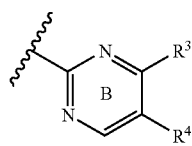

iii
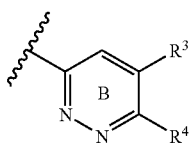

iv
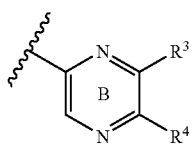

v
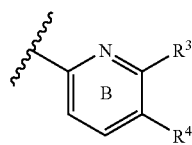

vi
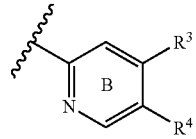

vii
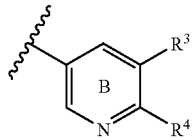

viii
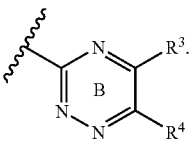

10. The compound according to claim 1, having one of the structures:

II-A
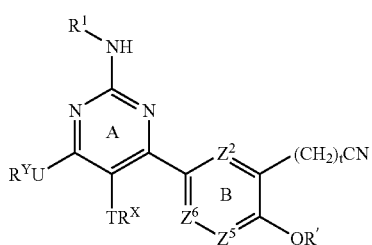

II-B
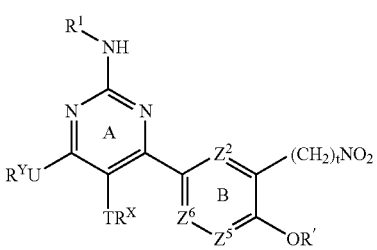

II-C
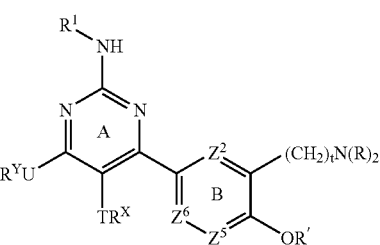

II-D
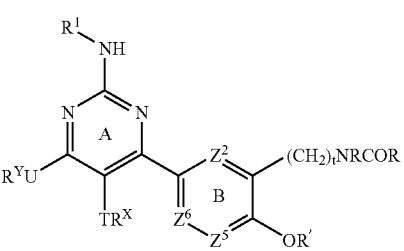

II-E
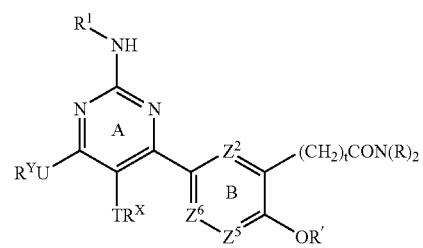
II-F
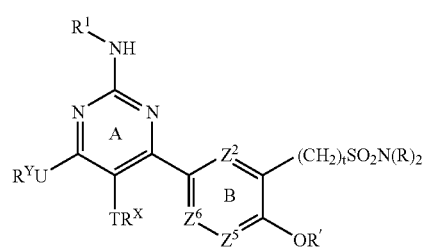
II-G
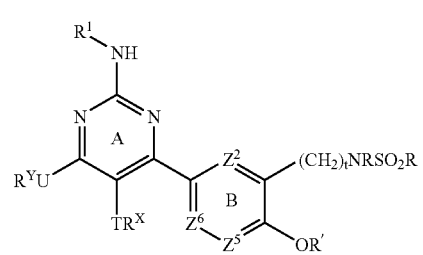
II-H
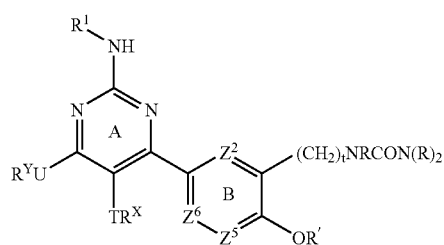
II-I
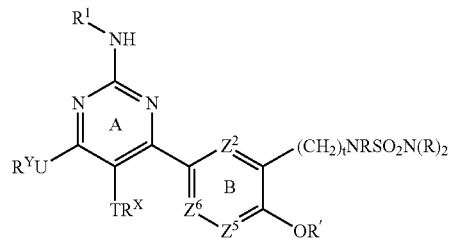
II-J
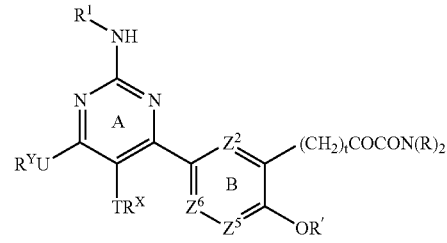
II-K
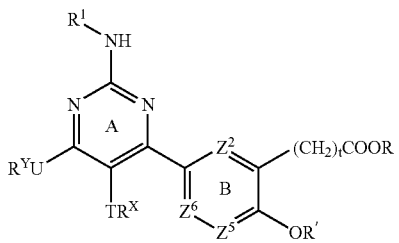
II-L
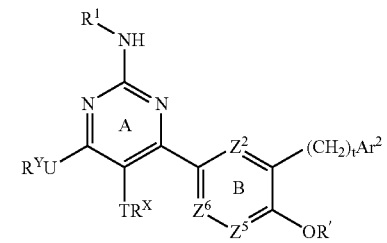
II-M
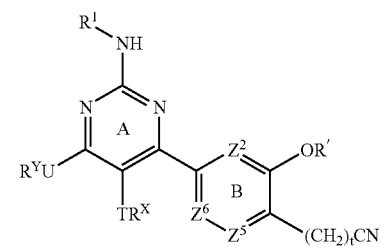
II-N
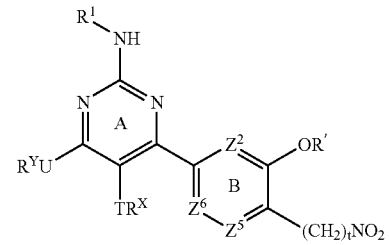
II-O
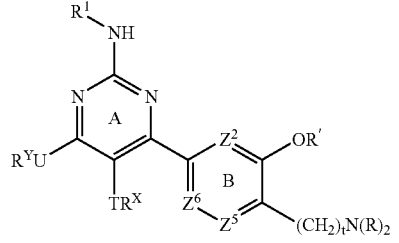
II-P
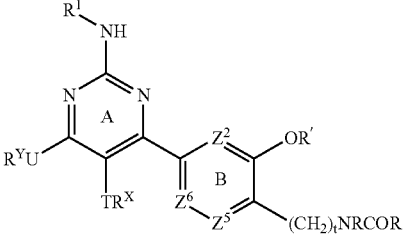

-continued

II-Q
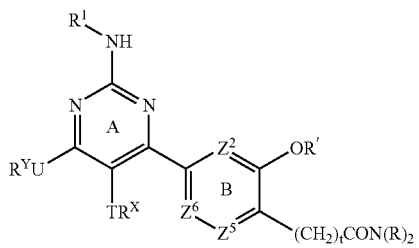

II-R
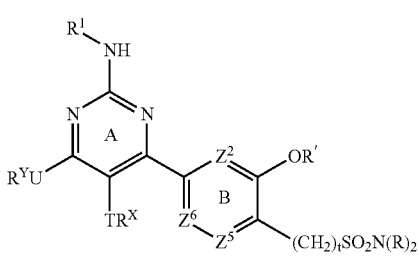

II-S
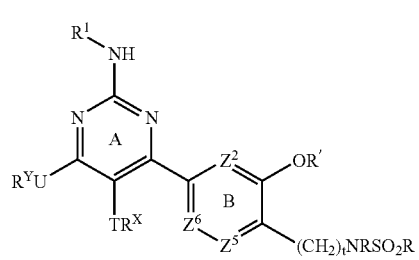

II-T
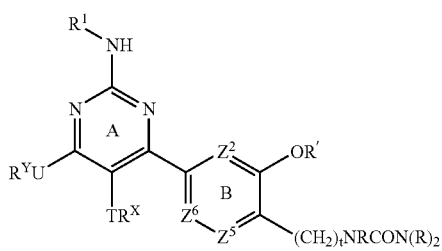

II-U
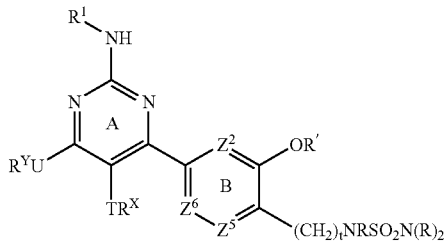

II-V
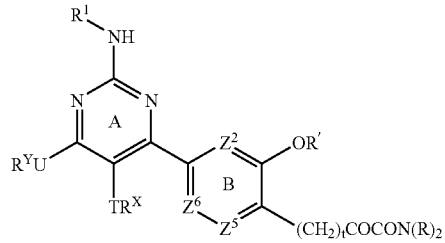

-continued

II-W
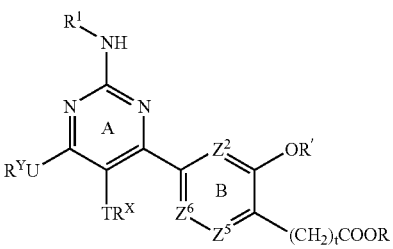

II-X
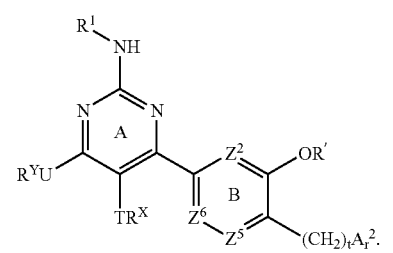

11. The compound according to claim 10, wherein compound variables are selected from one or more, or all of the following groups:

i) $R^1$ is selected from an optionally substituted group selected from phenyl, cyclohexyl, cyclopentyl, pyridyl, morpholino, piperazinyl, or piperidinyl;

ii) $R^1$ is an optionally substituted group selected from phenyl, cyclohexyl, or pyridyl;

iii) $R^1$ is optionally substituted phenyl;

iv) $Ar^1$ is substituted with up to five occurrences of $ZR^Z$, and $ZR^Z$ groups are selected from halogen, R', CN, $NO_2$, —N(R)(R'), —OR', —SR', —S(O)$_2$N(R)(R'), CO(C$_{1-4}$alkyl), —NRSO$_2$R', COO(C$_{1-4}$alkyl);

v) q is 1 and $ZR^Z$ is F, Cl, Br, COO(C$_{1-4}$alkyl), C$_{1-4}$alkyl, CN, $NO_2$, —$NH_2$, —OH, C$_{1-4}$alkoxy, —S(O)$_2$NH$_2$, or an optionally substituted benzyloxy, phenyloxy, or phenyl group;

vi) q is 1, and $ZR^Z$ is in the meta or para position and $ZR^Z$ is F, Cl, Br, benzyloxy, phenyl, phenyloxy, COO(C$_{1-4}$ alkyl), —$NH_2$, —OH, C$_{1-4}$alkoxy, or —S(O)$_2$NH$_2$;

vii) $TR^X$ and $UR^Y$ are selected from hydrogen, halogen, $NO_2$, CN, OR, SR or N(R)$_2$, or C$_{1-4}$aliphatic optionally substituted with oxo, OR, SR, N(R)$_2$, halogen, $NO_2$ or CN;

viii) $TR^X$ and $UR^Y$ groups are selected from hydrogen, Me, OH, OMe or N(R)$_2$;

ix) $TR^X$ and $UR^Y$ are each hydrogen;

x) $Z^2$ and $Z^6$ are each CH;

xi) t is 0;

xii) t is 1; or xiii) $Ar^2$ is an optionally substituted tetrazole, triazole, oxazole, thiazole, thiadiazole, oxadiazole or pyridyl group.

12. The compound according to claim 1, wherein compounds have one of the structures:
II-A-(i)
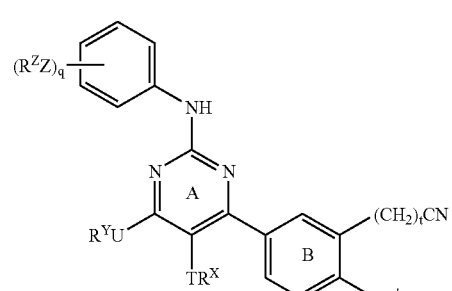
II-B-(i)
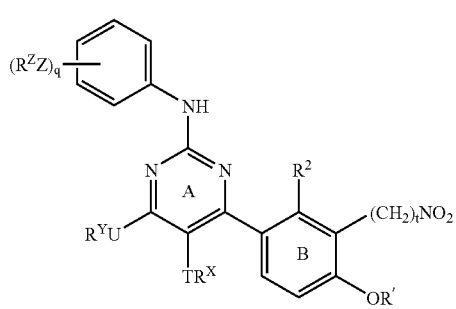
II-C-(i)
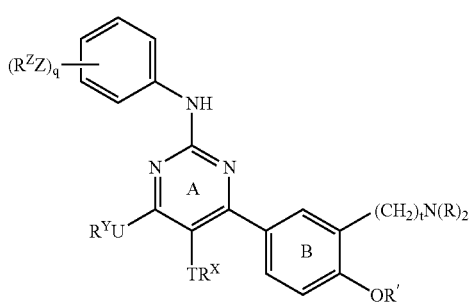
II-D-(i)
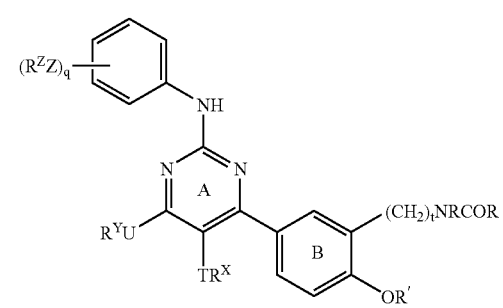
II-E-(i)
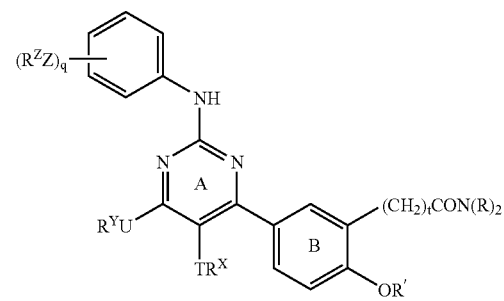
-continued
II-F-(i)
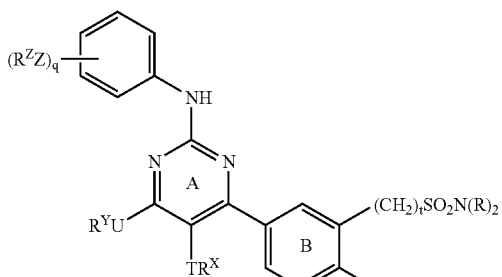
II-G-(i)
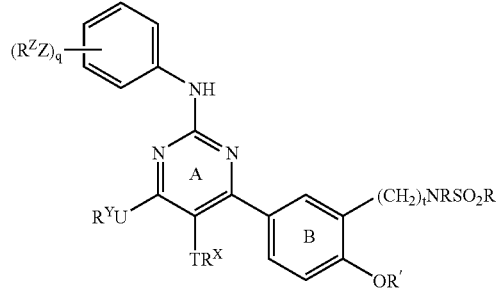
II-H-(i)
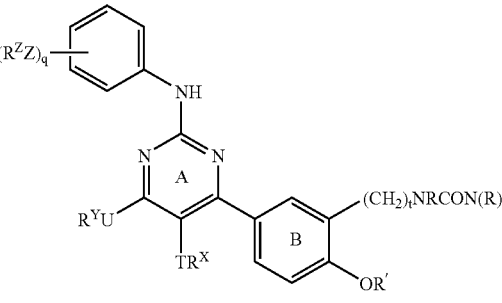
II-I-(i)
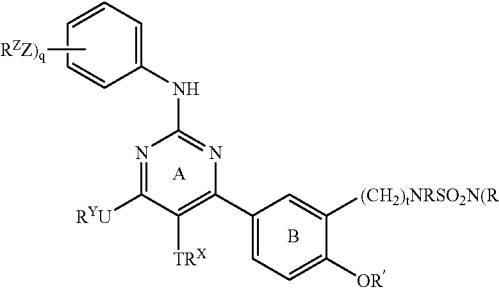
II-J-(i)
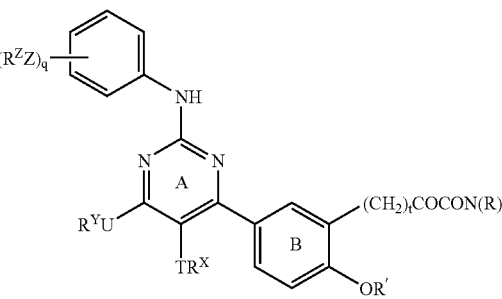

-continued
II-K-(i)
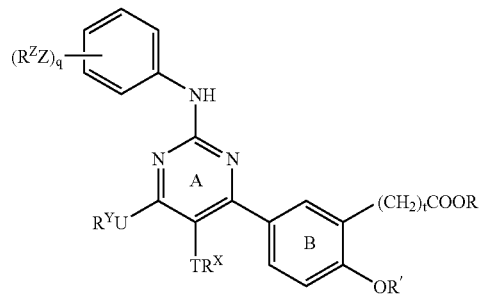
II-L-(i)
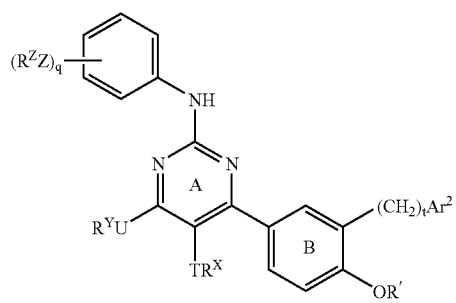
II-M-(i)
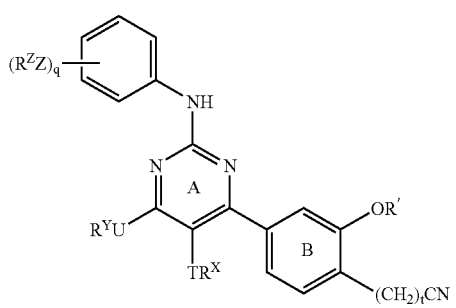
II-N-(i)
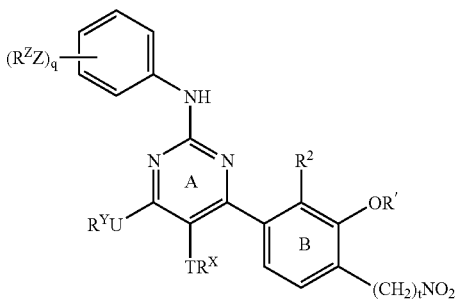
II-O-(i)
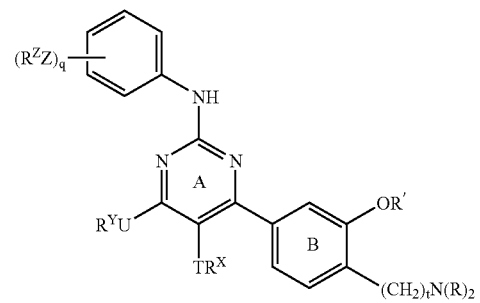
-continued
II-P-(i)
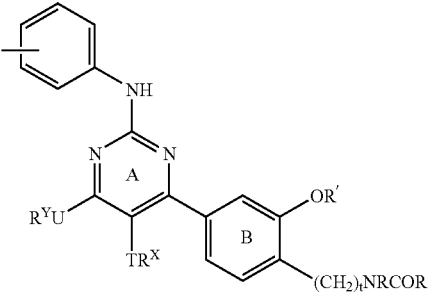
II-Q-(i)
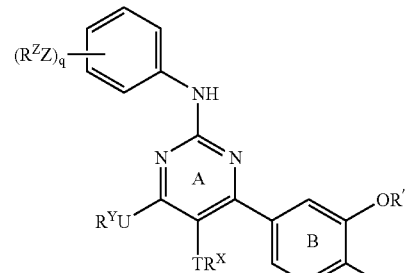
II-R-(i)
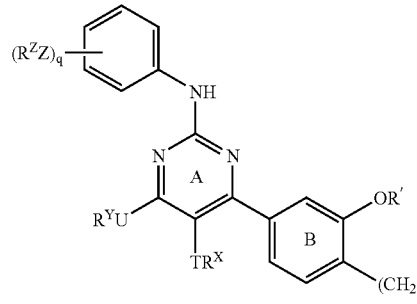
II-S-(i)
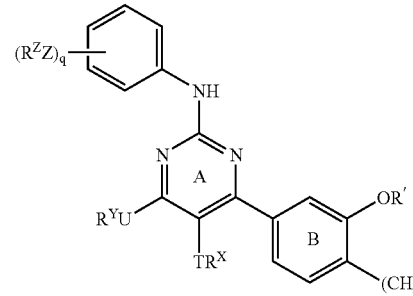
II-T-(i)

-continued
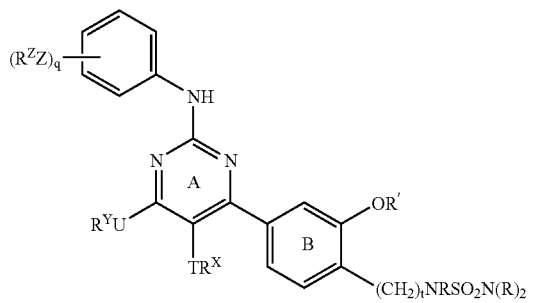
II-U-(i)
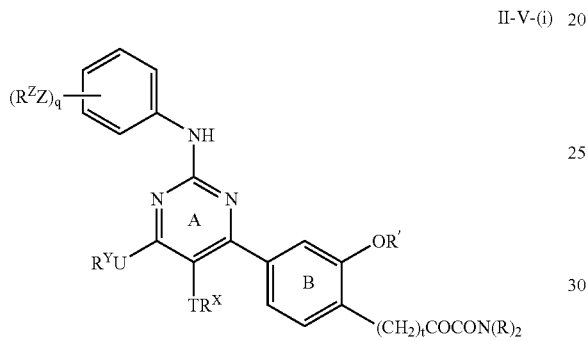
II-V-(i)
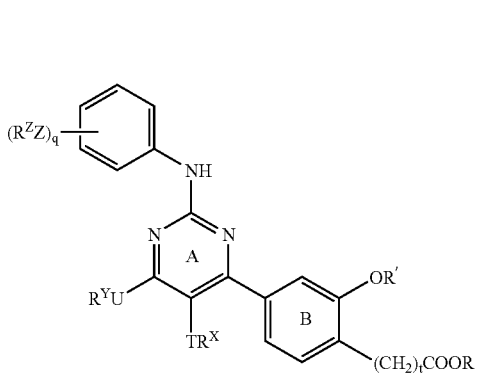
II-W-(i)
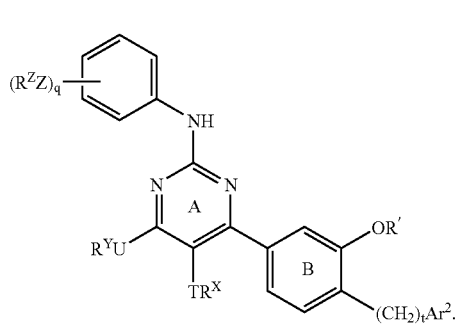
II-X-(i)
13. The compound according to claim 1, where $UR^Y$ and $TR^X$ are each hydrogen, and the compounds have the general structures:
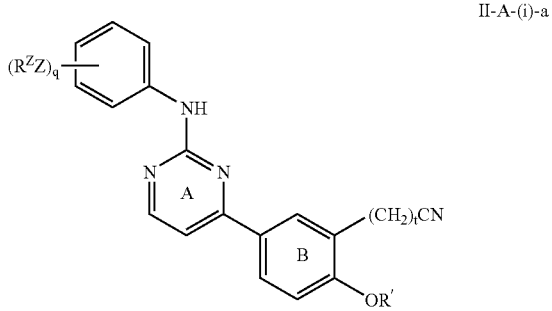
II-A-(i)-a
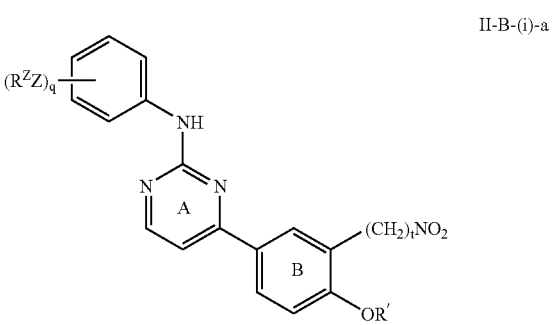
II-B-(i)-a
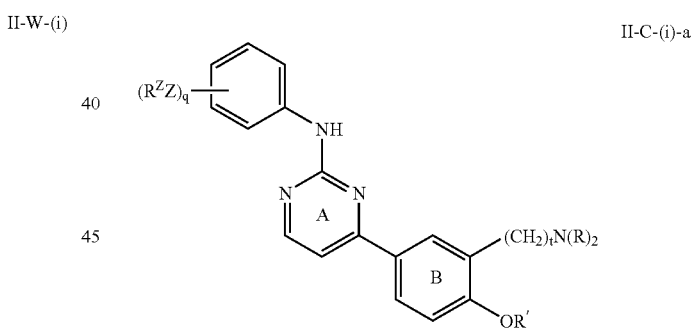
II-C-(i)-a
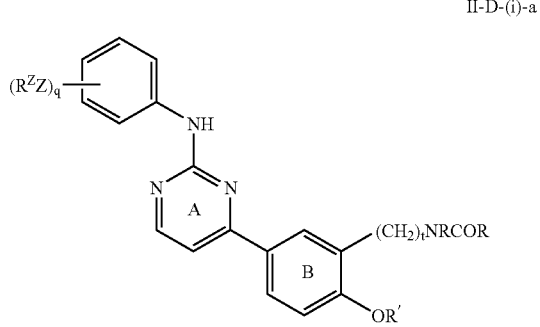
II-D-(i)-a II-E-(i)-a
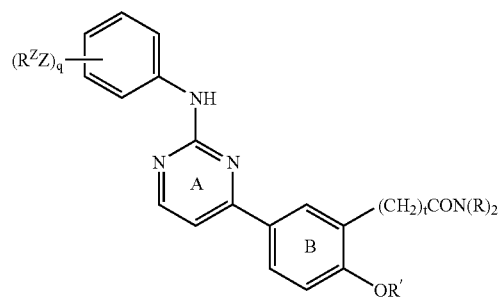
II-F-(i)-a
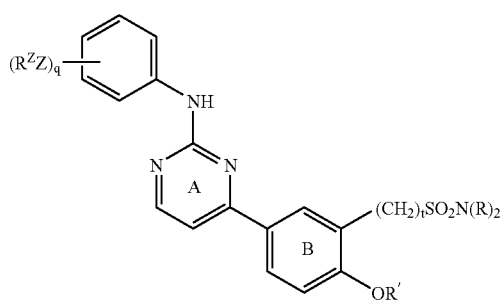
II-G-(i)-a
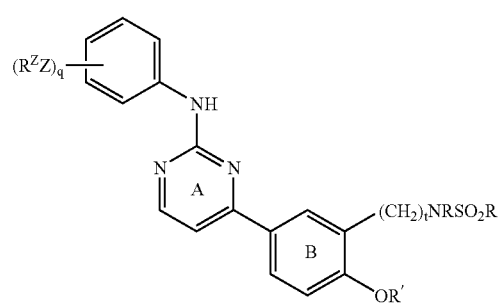
II-H-(i)-a
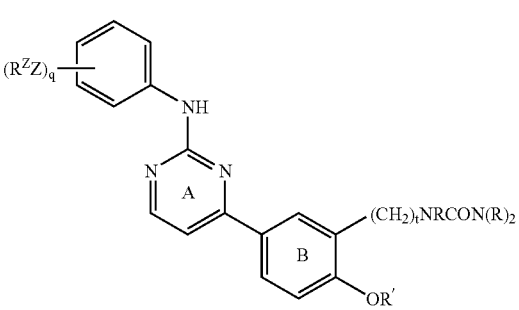
II-I-(i)-a
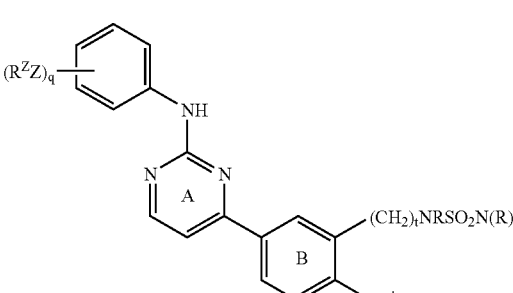
II-J-(i)-a
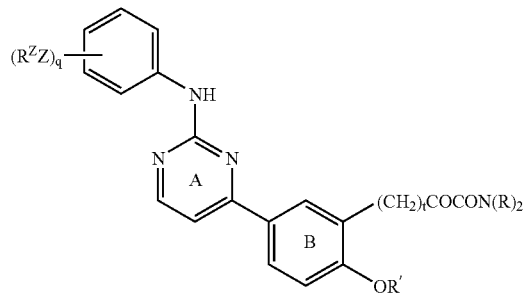
II-K-(i)-a
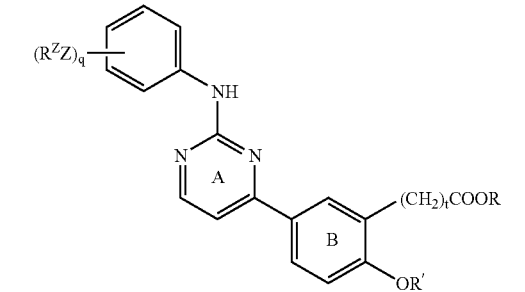
II-L-(i)-a
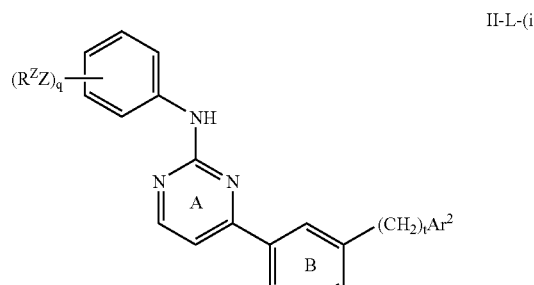
II-M-(i)-a
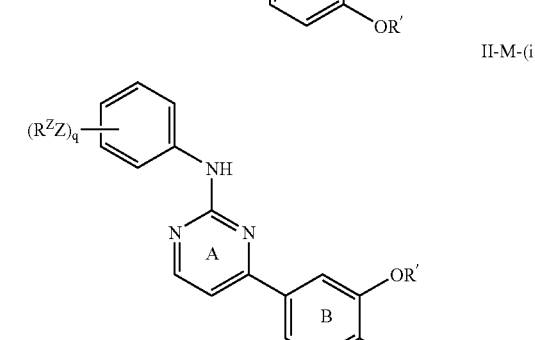
II-N-(i)-a
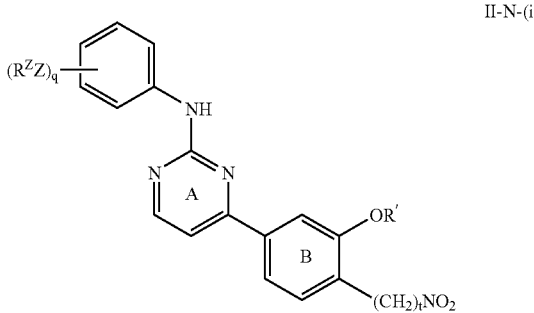

II-O-(i)-a
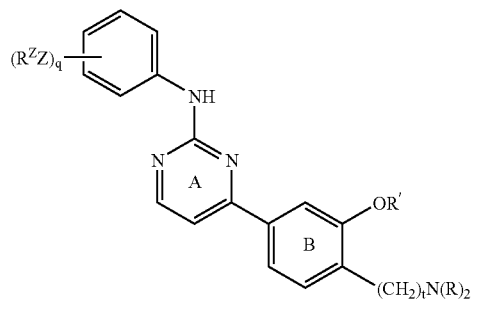
II-P-(i)-a
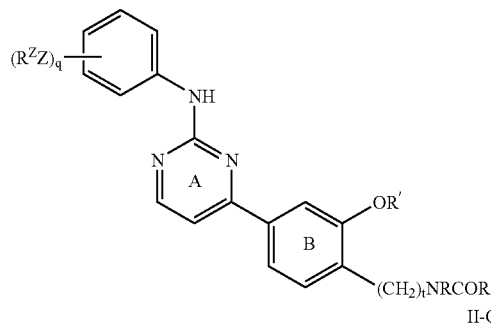
II-Q-(i)-a
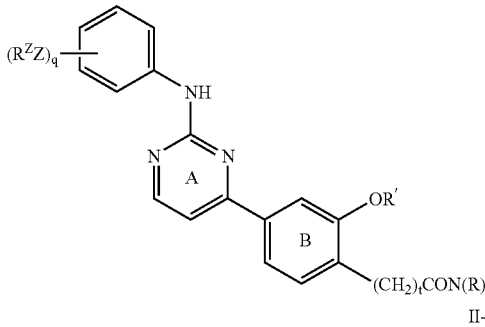
II-R-(i)-a
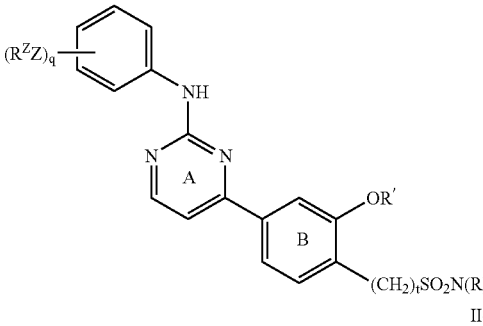
II-S-(i)-a
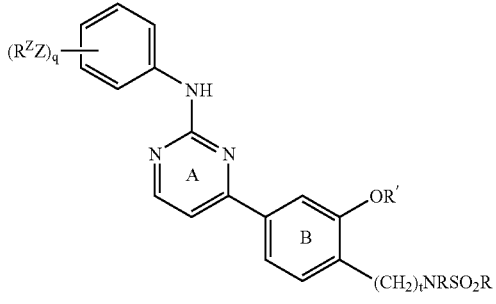
II-T-(i)-a
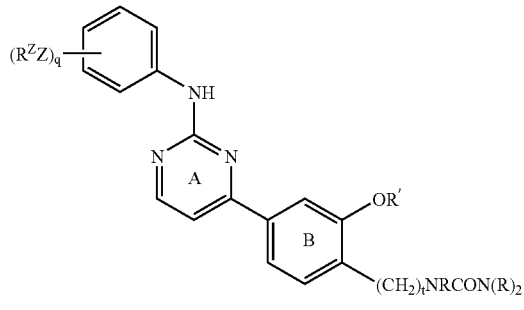
II-U-(i)-a
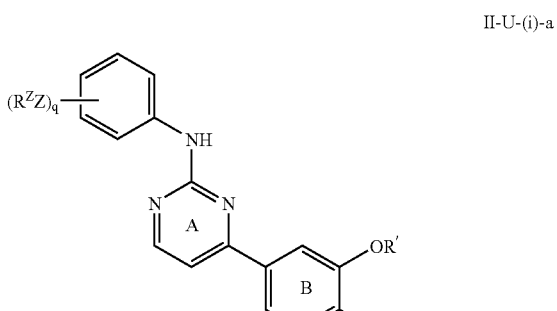
II-V-(i)-a
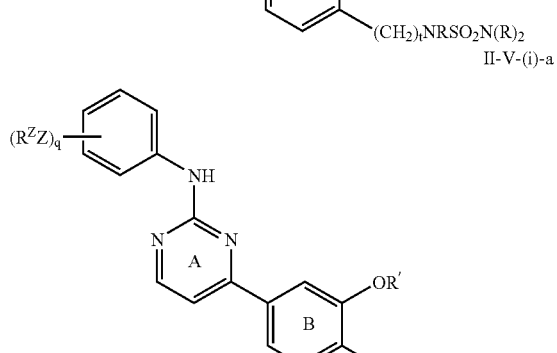
II-W-(i)-a
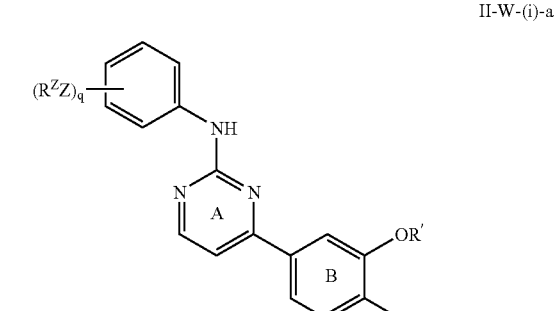
II-X-(i)-a
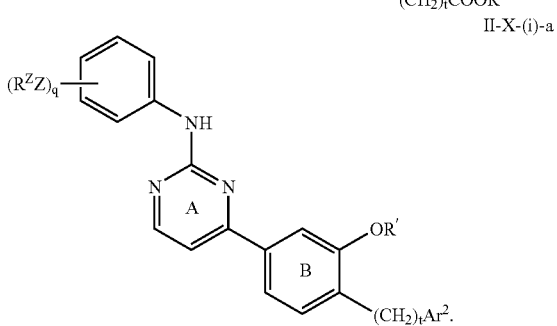

14. The compound according to claim 13, wherein:
(a) q is 0, 1, or 2, and $ZR^Z$ is halogen, R', CN, $NO_2$, —N(R)(R'), —OR', —SR', —S(O)$_2$N(R)(R'), CO(C$_{1-4}$alkyl), —NRSO$_2$R', COO(C$_{1-4}$alkyl);
(b) t is 0;
(c) R is optionally substituted C$_{1-6}$alkyl or hydrogen; and
(d) R' is optionally substituted C$_{1-6}$alkyl or hydrogen.
15. The compound according to claim 1, selected from one of the structures:
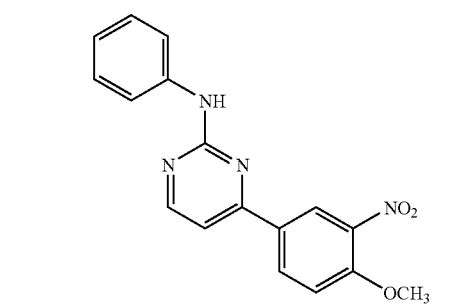
II-1
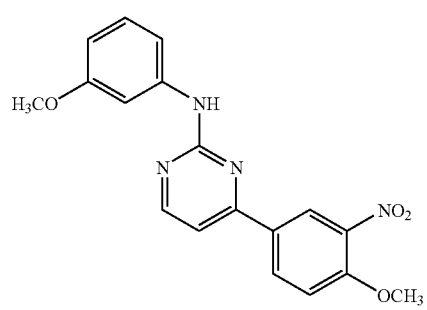
II-2
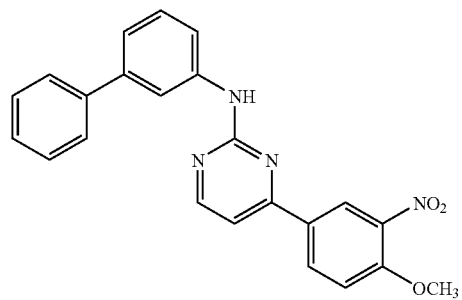
II-3
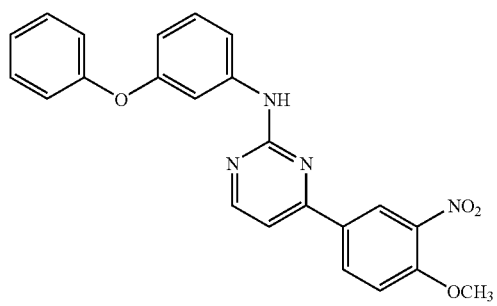
II-4
-continued
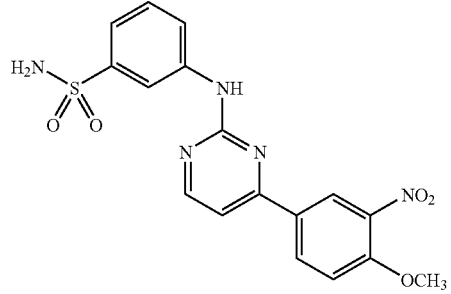
II-5
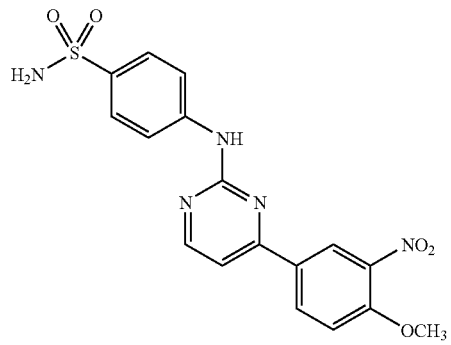
II-6
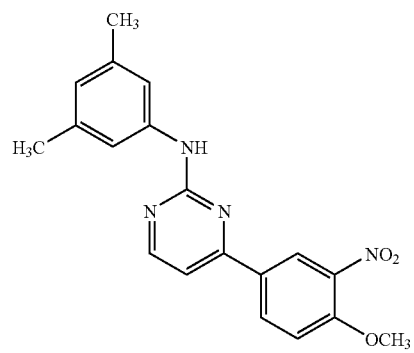
II-7
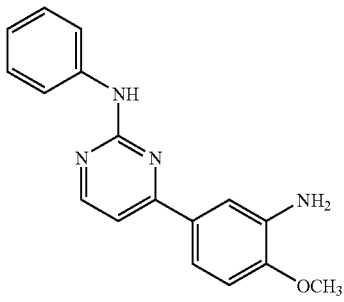
II-8
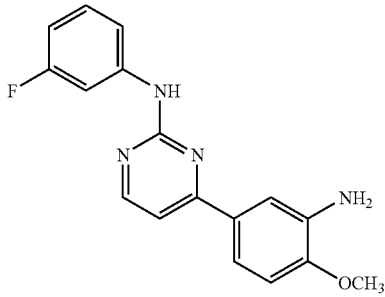
II-9

II-10
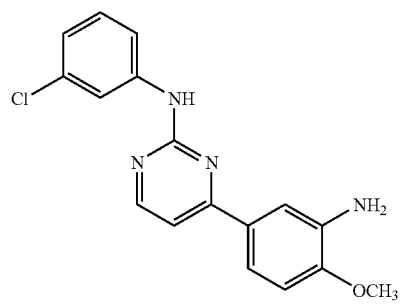
II-11
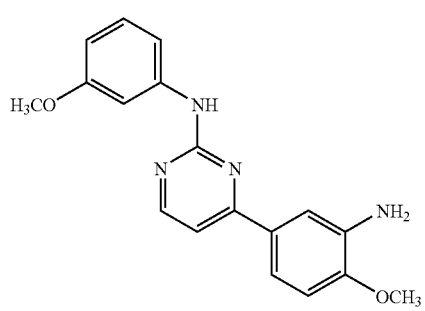
II-12
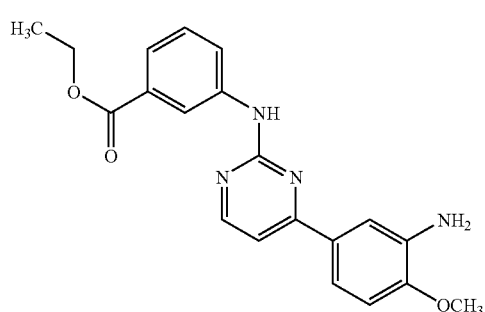
II-13
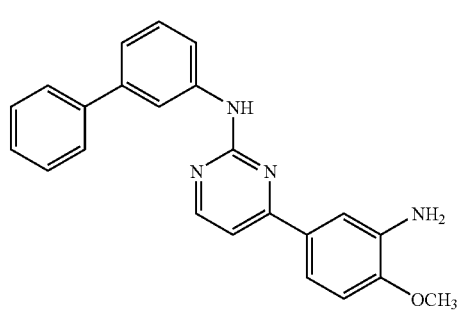
II-14
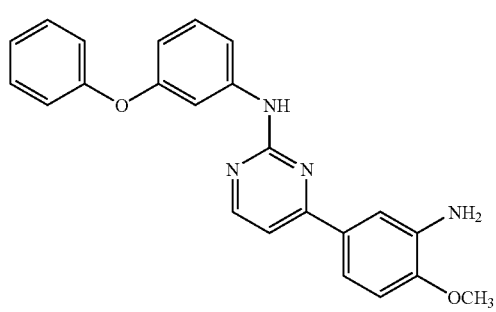
II-15
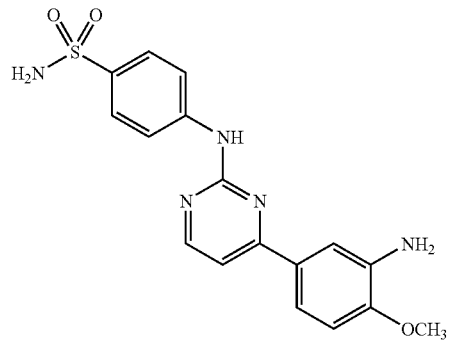
II-16
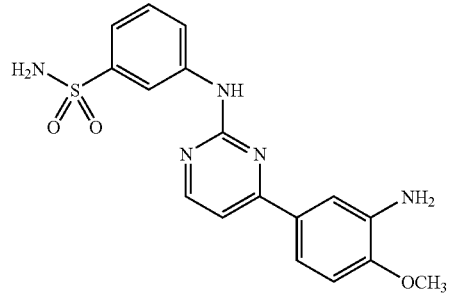
II-17
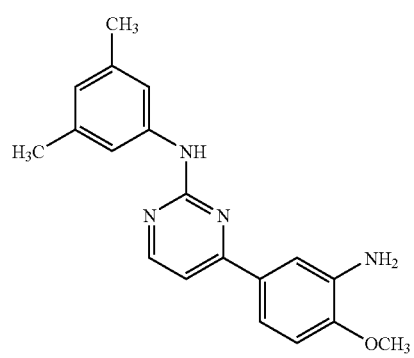
II-18
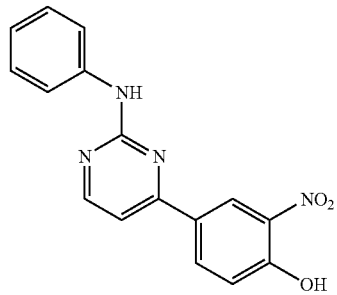
II-19
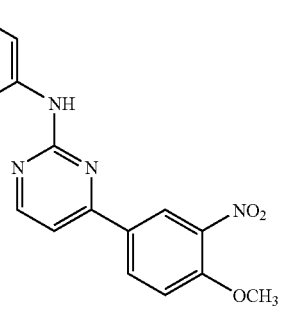

-continued
II-20
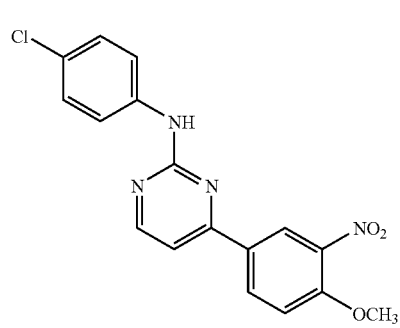
II-21
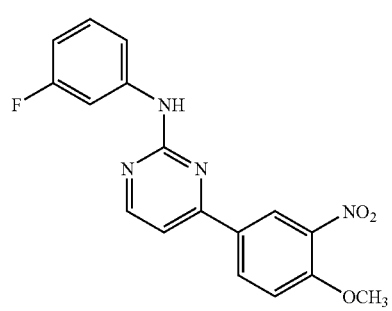
II-22
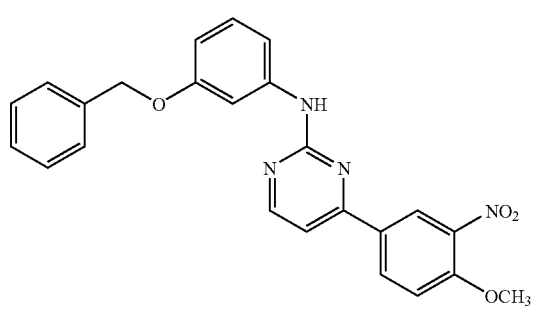
II-23
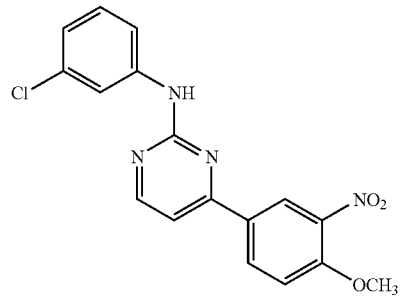
II-24
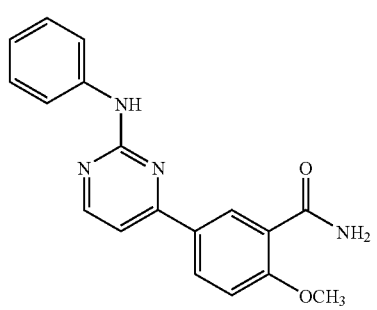
-continued
II-25
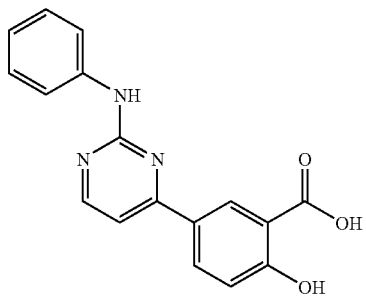
II-26
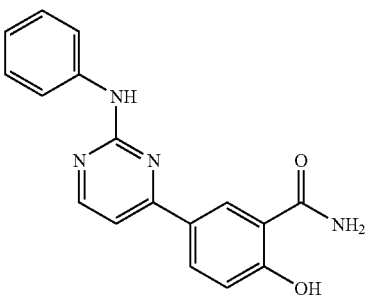
II-27
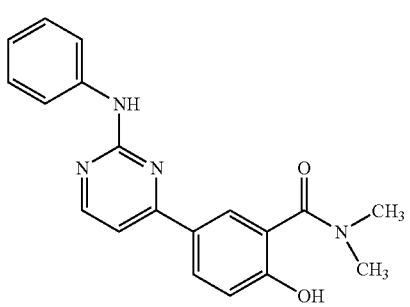
II-28
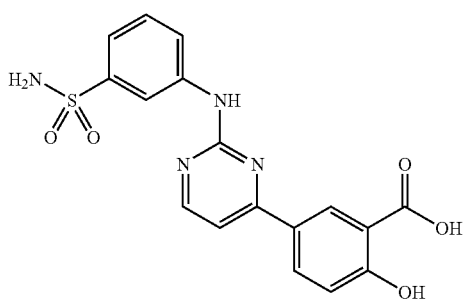
II-29
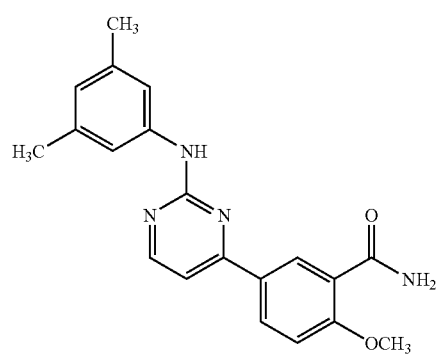

-continued
II-30
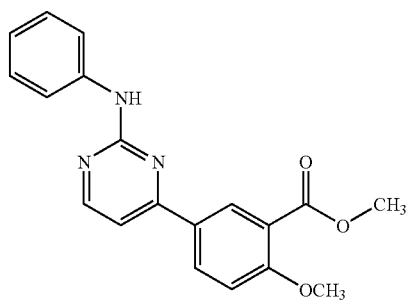
II-31
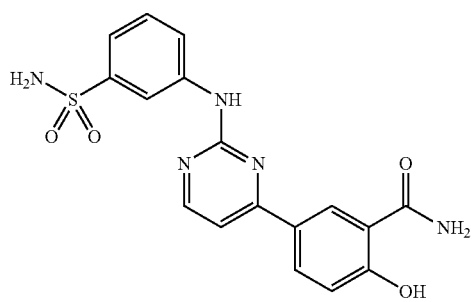
II-32
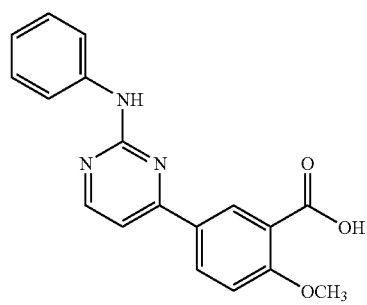
II-33
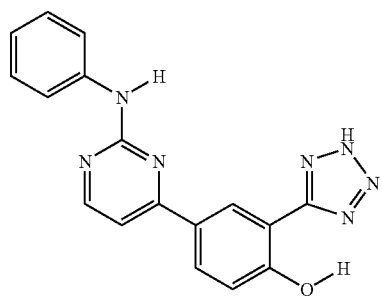
-continued
II-34
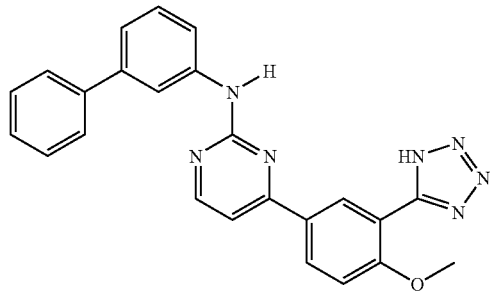
II-35
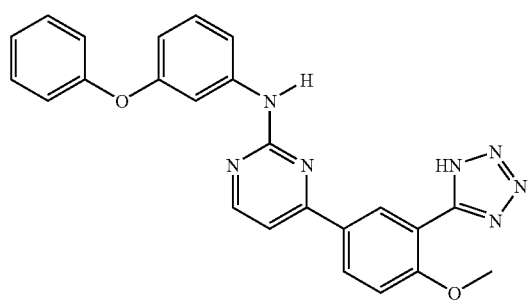
II-36
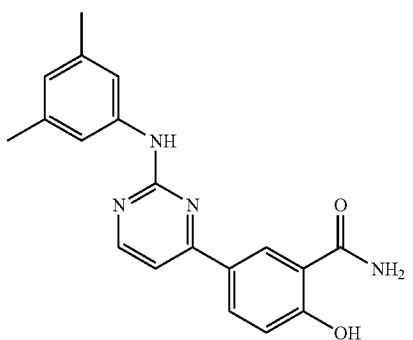
II-37
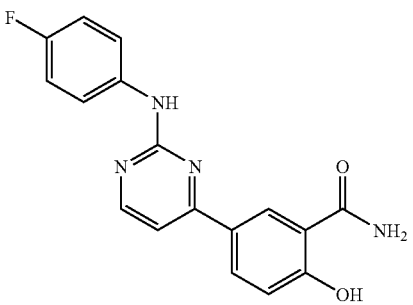
II-38
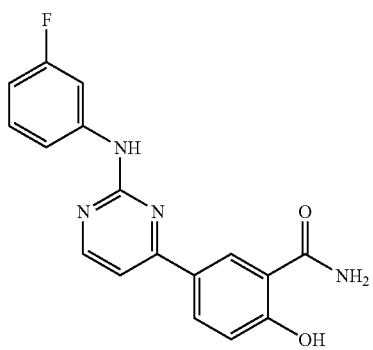

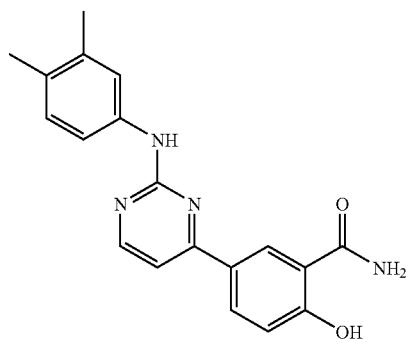
II-39
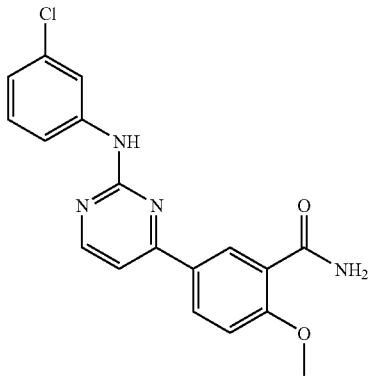
II-43
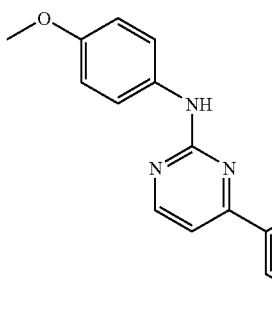
II-40
II-44
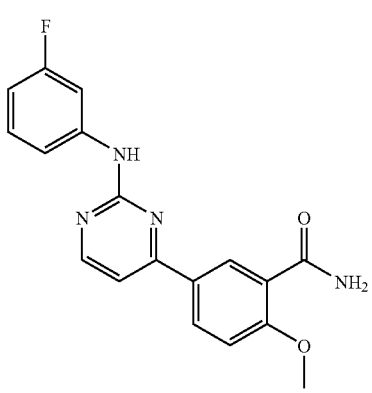
II-41
II-45
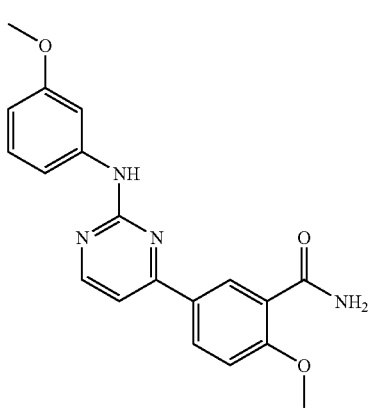
II-42
II-46

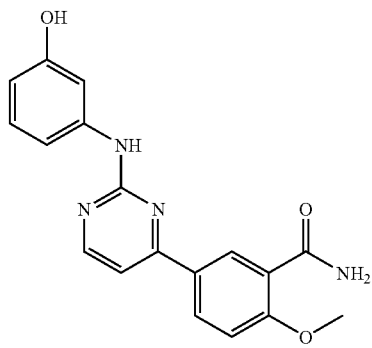
II-47
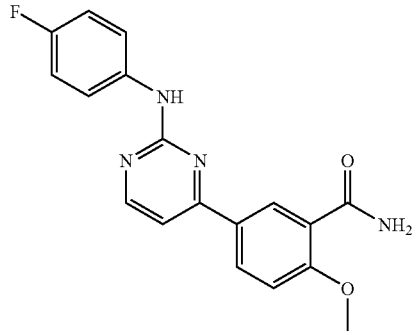
II-51
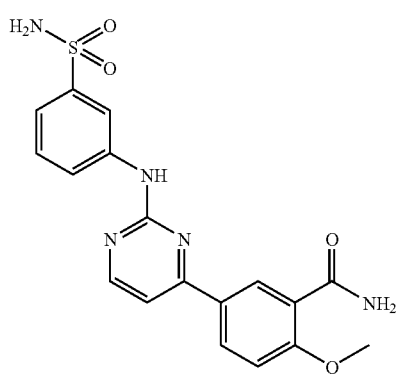
II-48
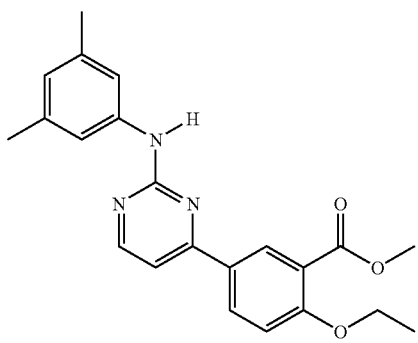
II-52
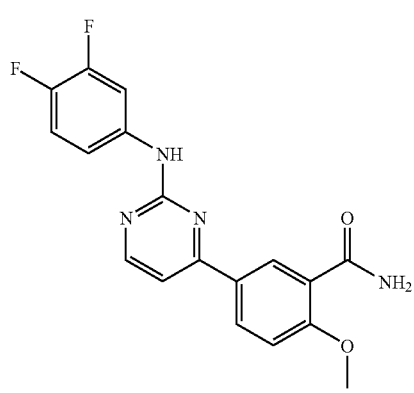
II-49
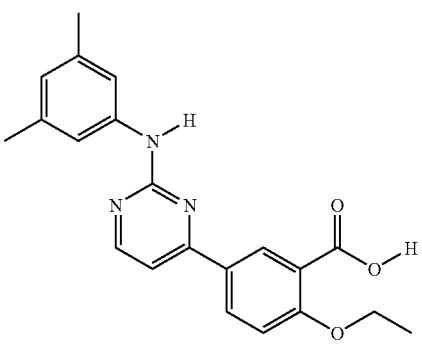
II-53
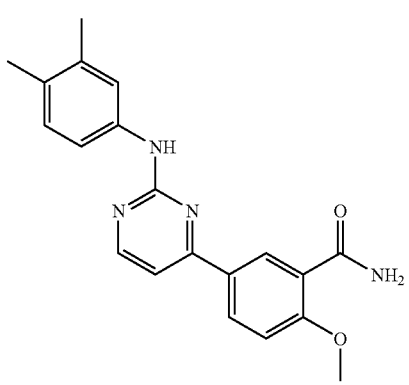
II-50
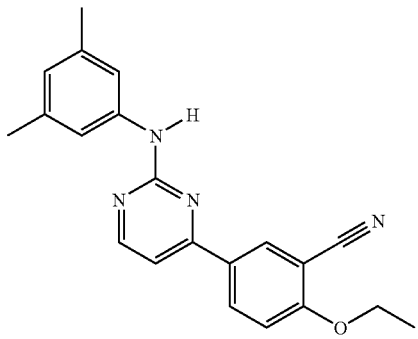
II-54

-continued
II-55
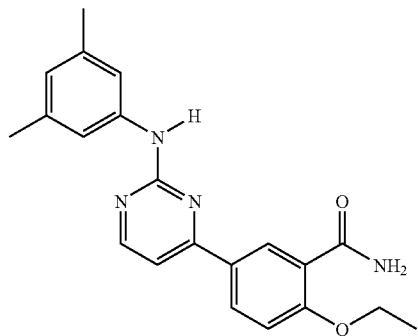
II-56
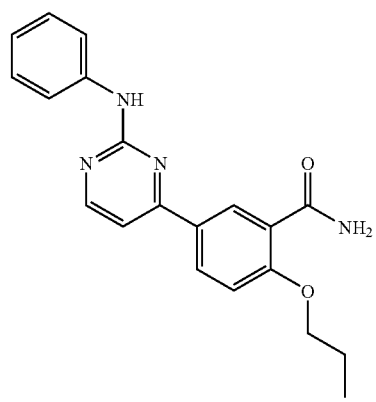
II-57
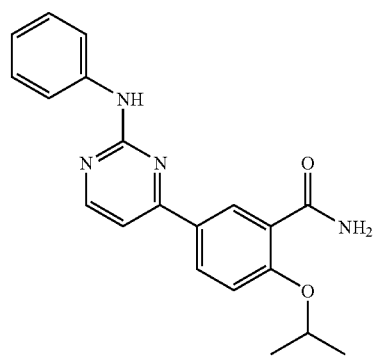
II-58
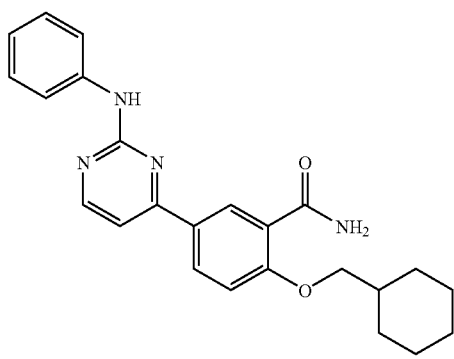
-continued
II-59
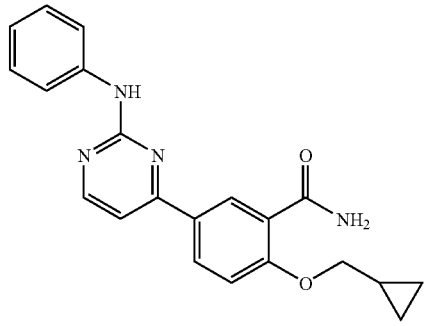
II-60
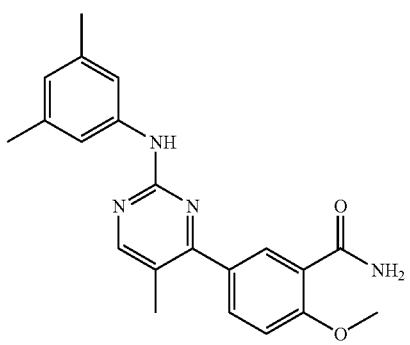
II-61
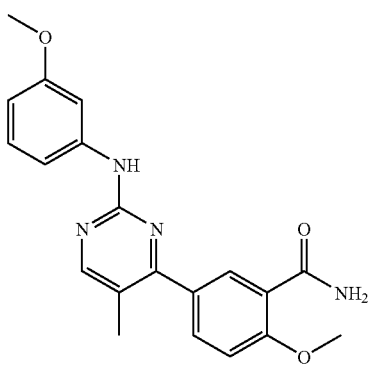
II-62
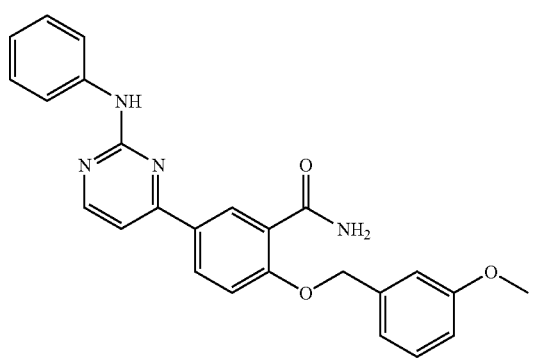

-continued
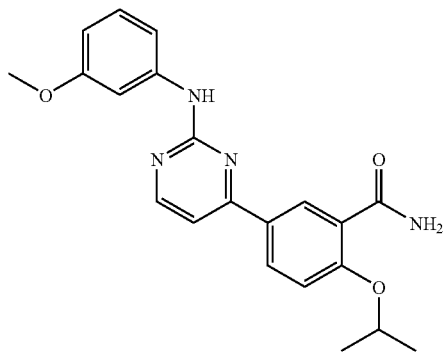
II-63
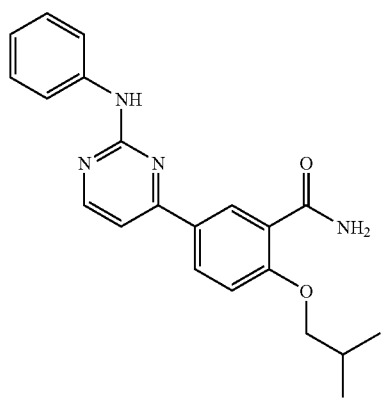
II-64
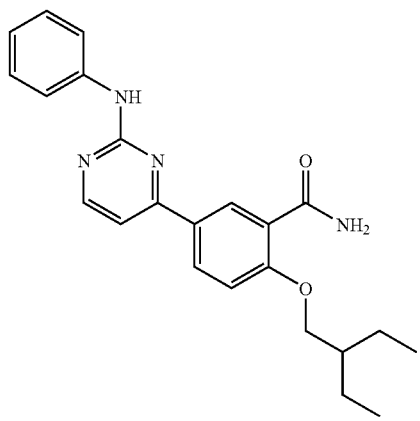
II-65
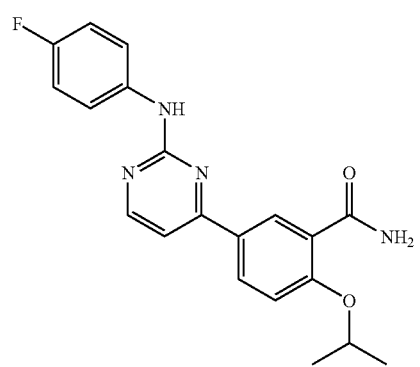
II-66
-continued
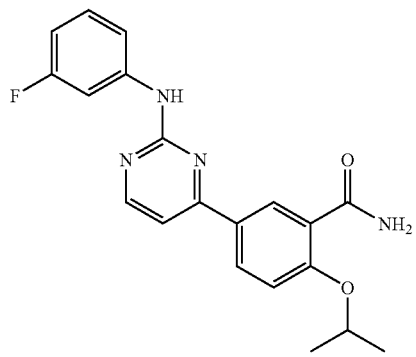
II-67
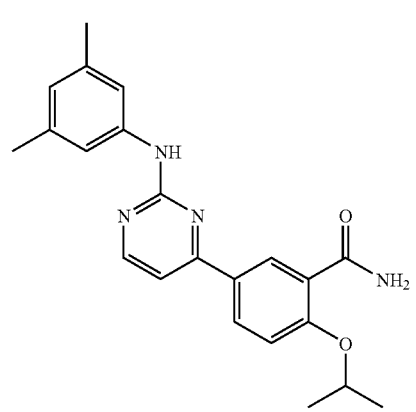
II-68
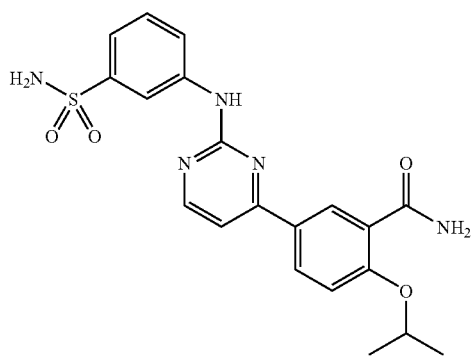
II-69
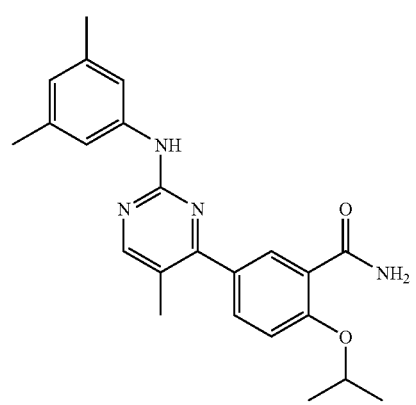
II-70

-continued
II-71
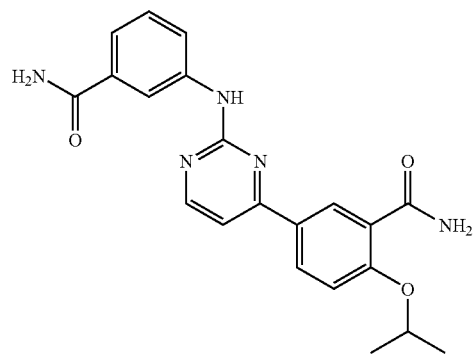
II-72
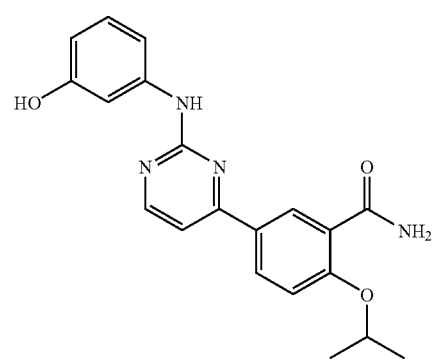
II-73
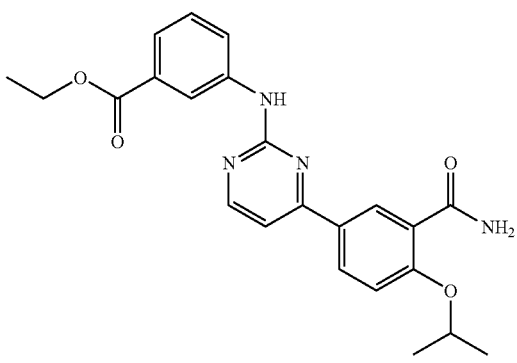
II-74
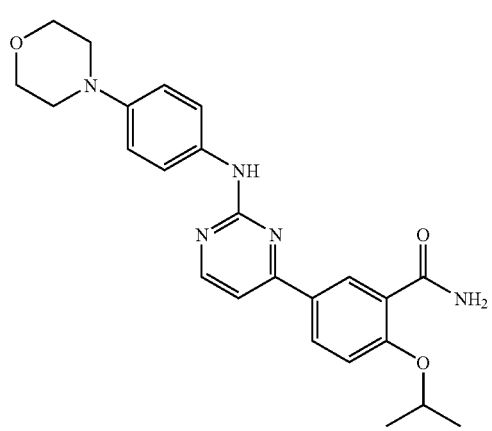
-continued
II-75
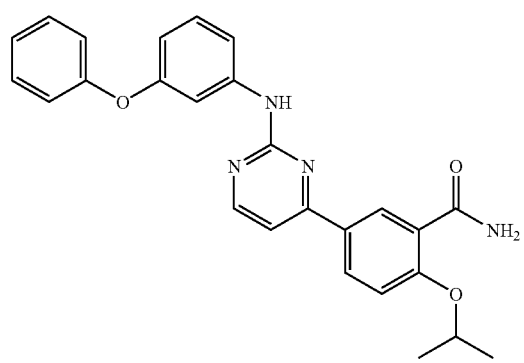
II-76
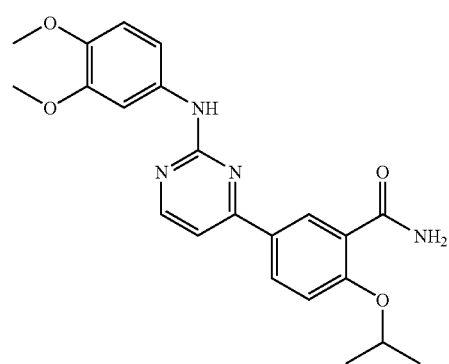
II-77
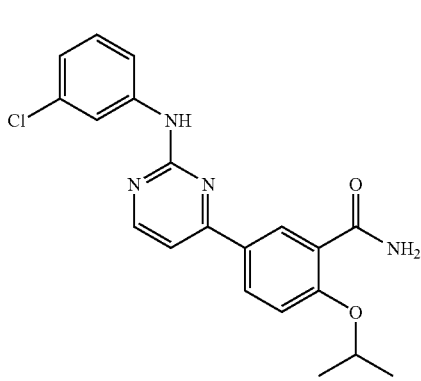
II-78
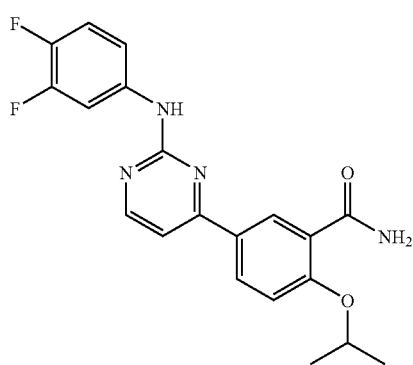

II-79
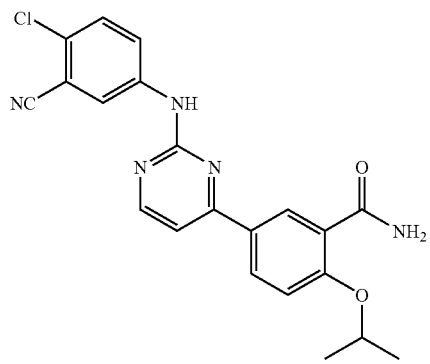
II-80
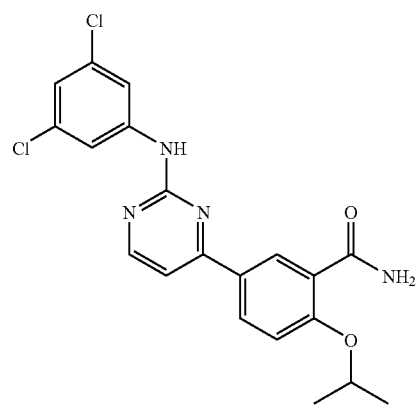
II-81
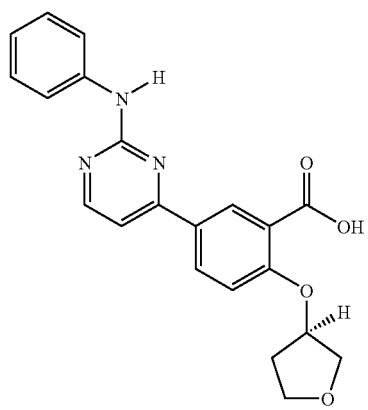
II-82
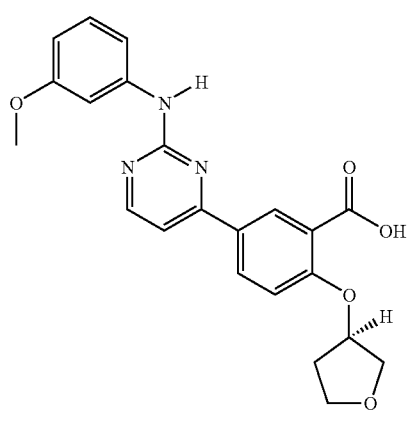
II-83
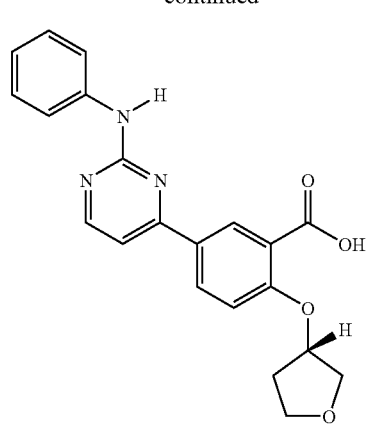
II-84
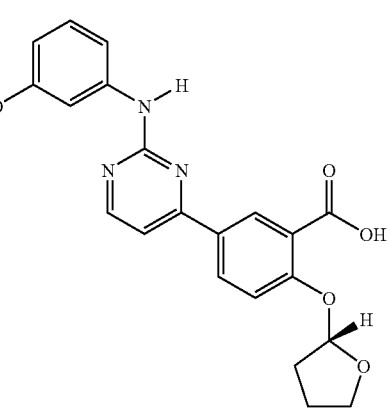
II-85
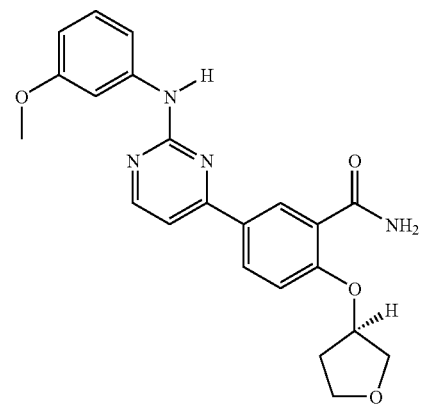
II-86
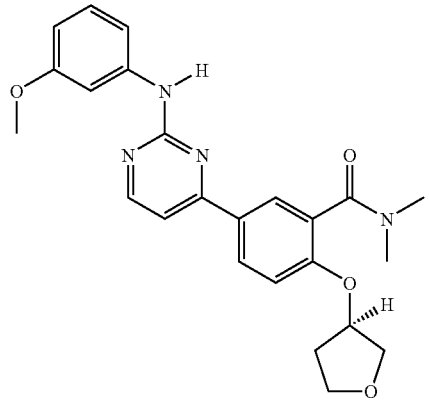

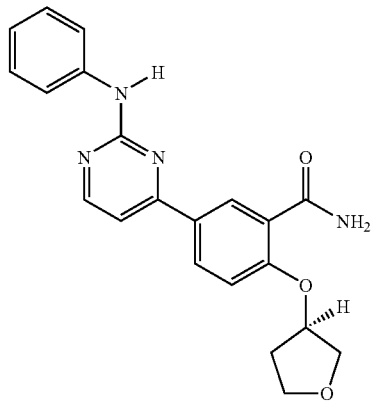 II-87
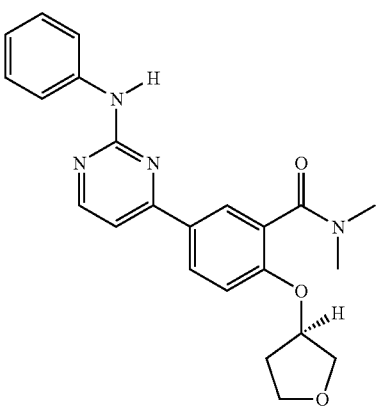 II-88
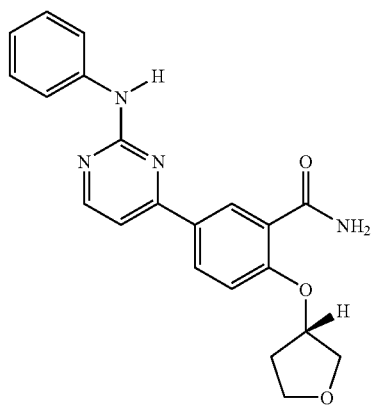 II-89
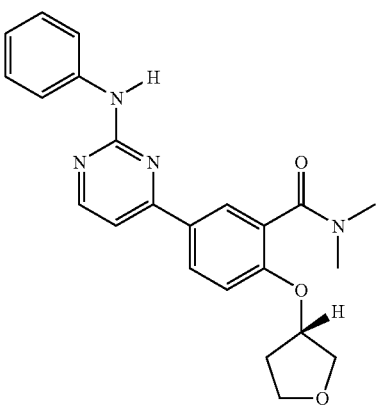 II-90
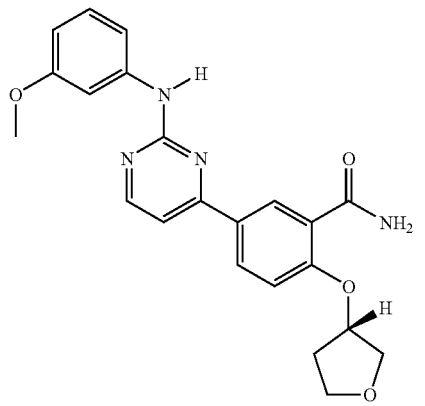 II-91
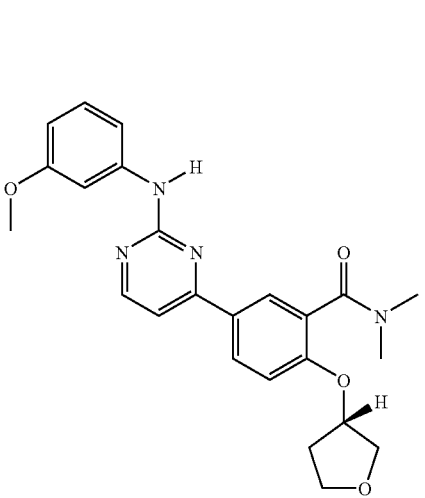 II-92
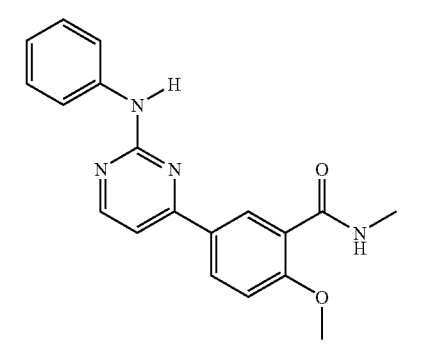 II-93
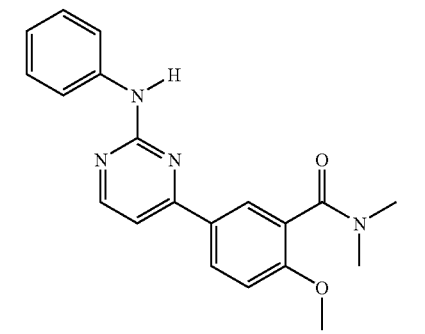 II-94

-continued
II-95
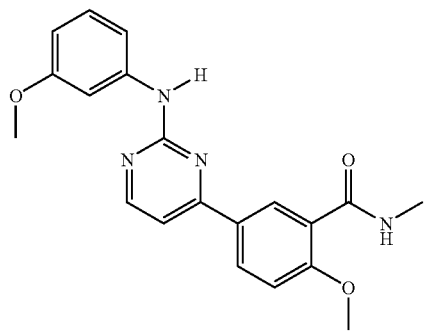
II-96
II-97
II-98
-continued
II-99
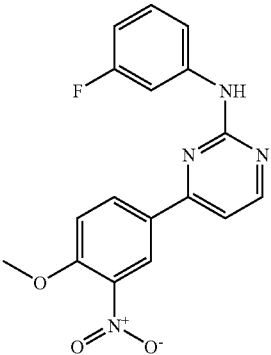
II-100
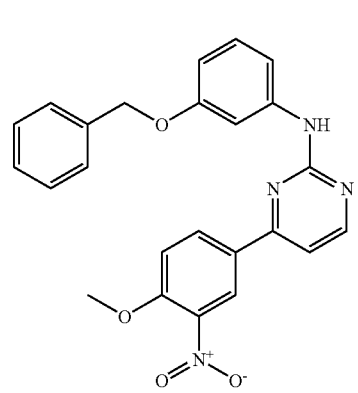
II-101
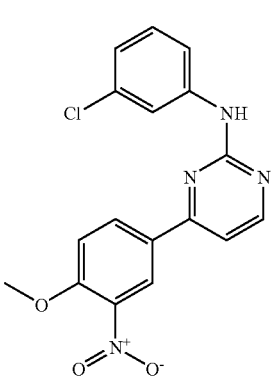
II-102
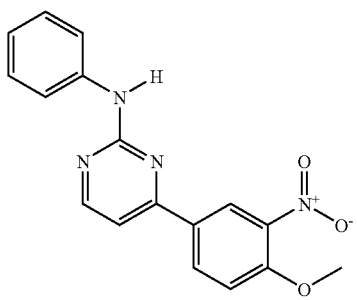

-continued
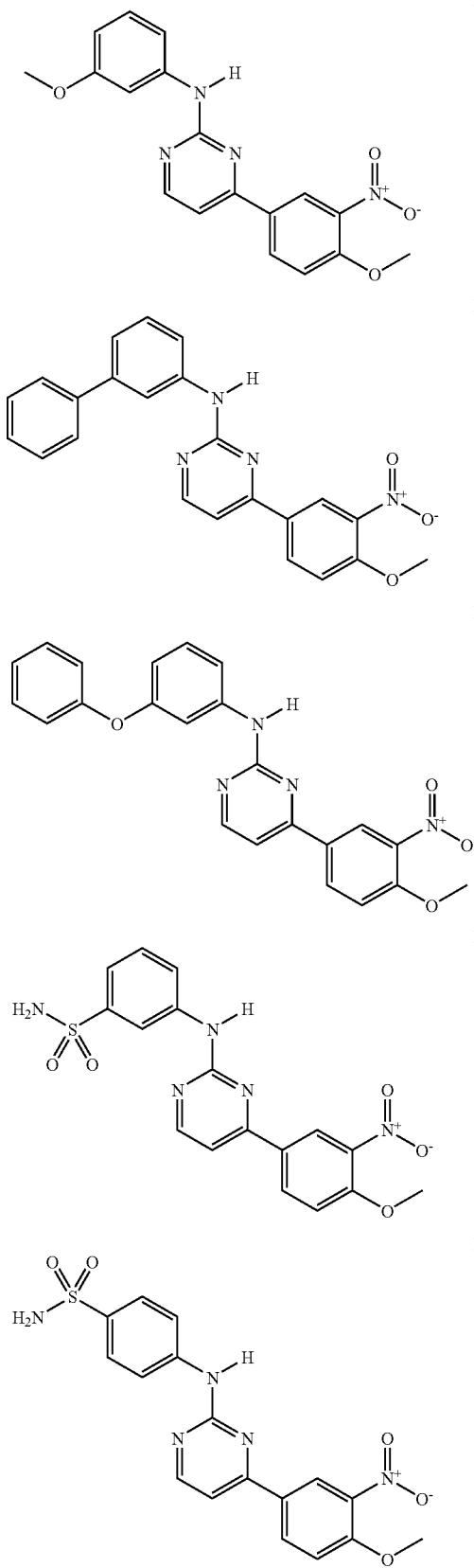
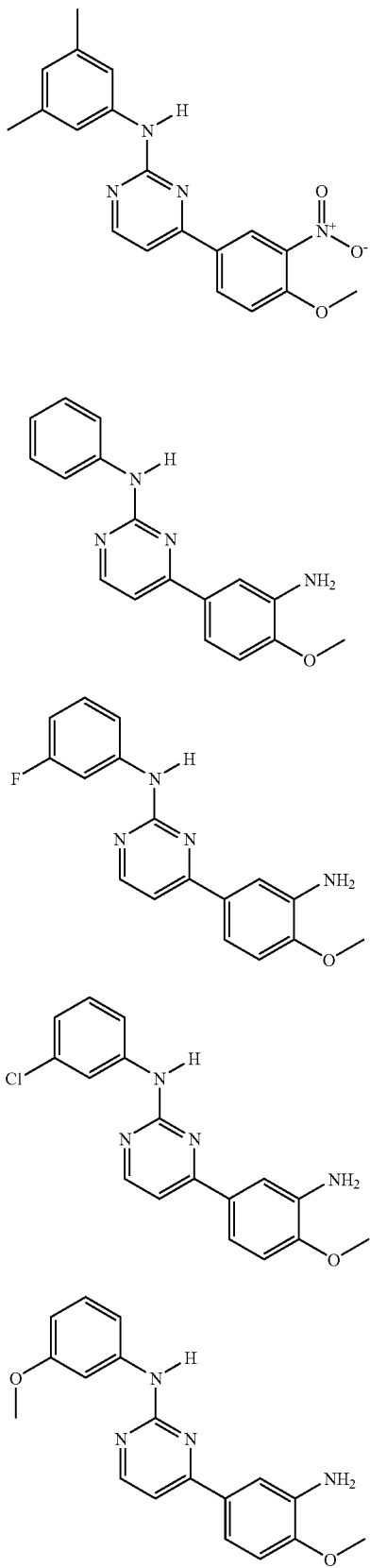

-continued
II-113
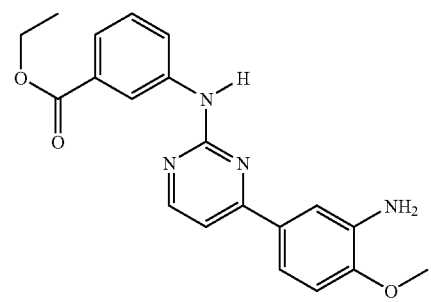
II-114
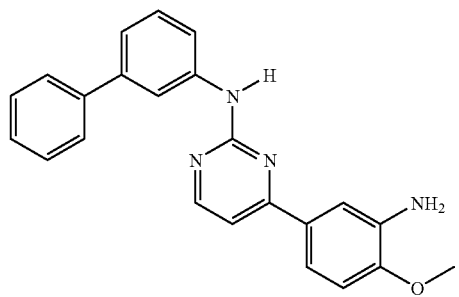
II-115
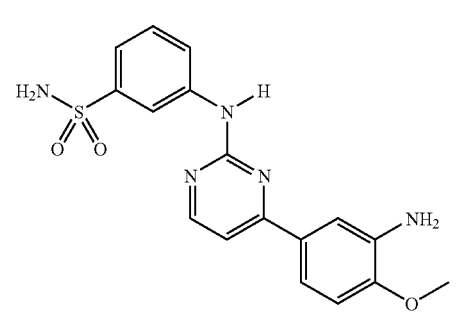
II-116
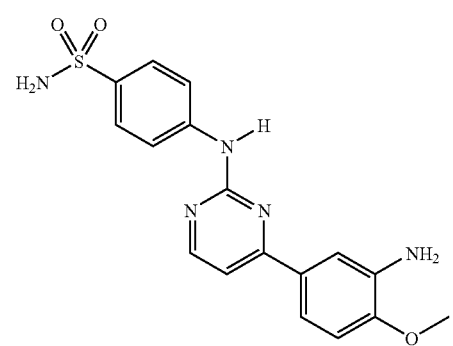
II-117
-continued
II-118
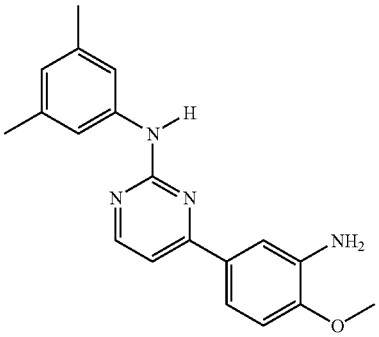
II-119
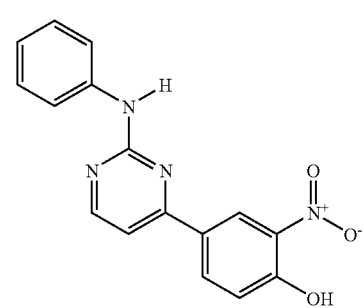
II-120
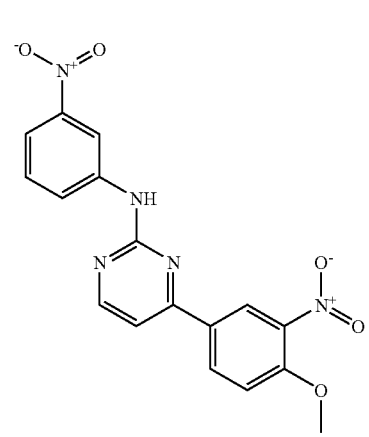
II-121
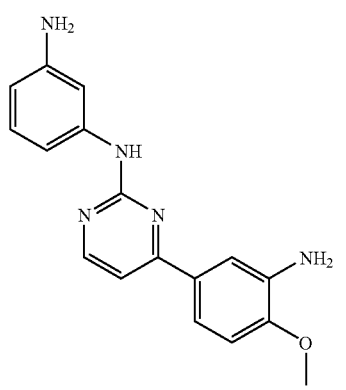

-continued
II-122
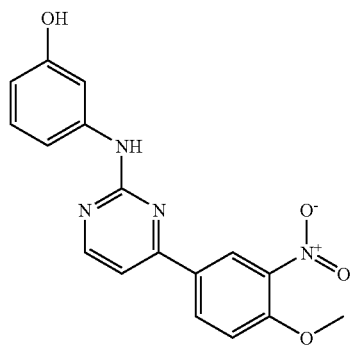
II-123
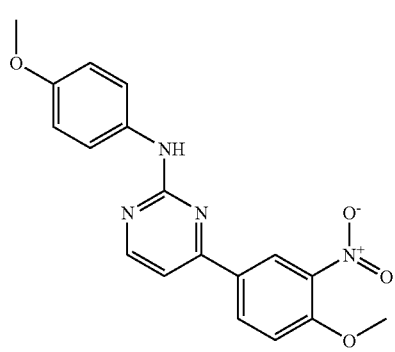
II-124
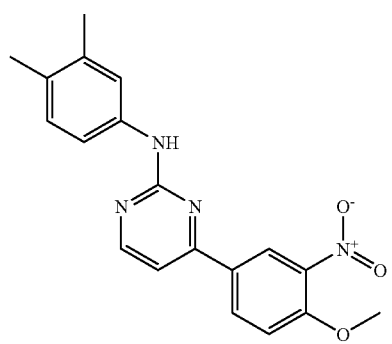
II-125
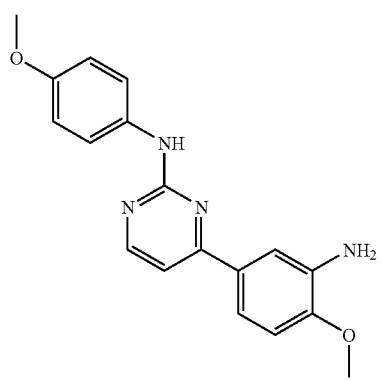
-continued
II-126
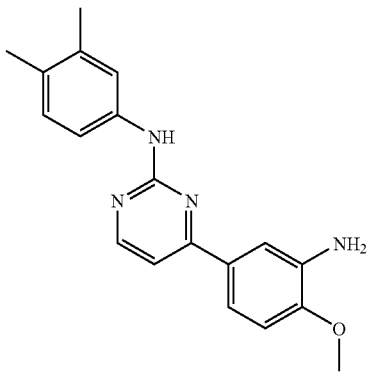
II-127
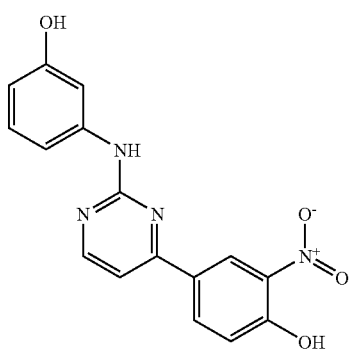
II-128
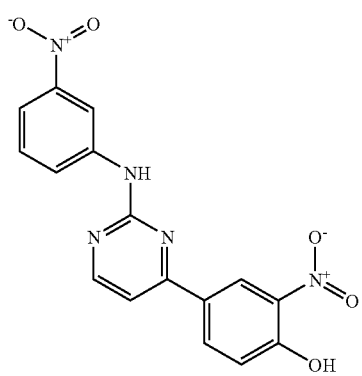
II-129
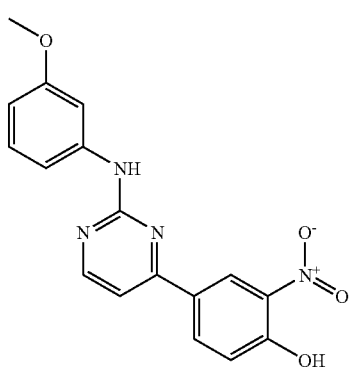

-continued
II-130
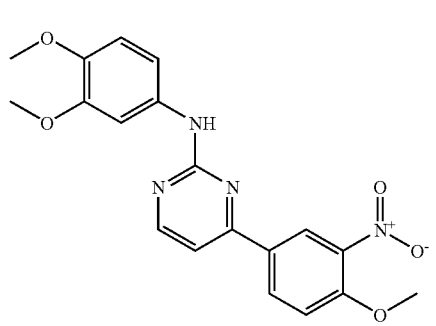
II-131
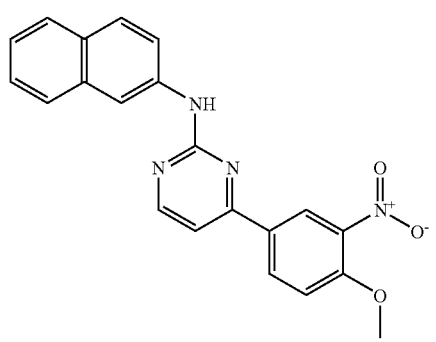
II-132
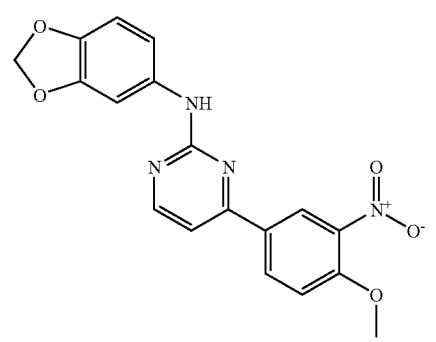
II-133
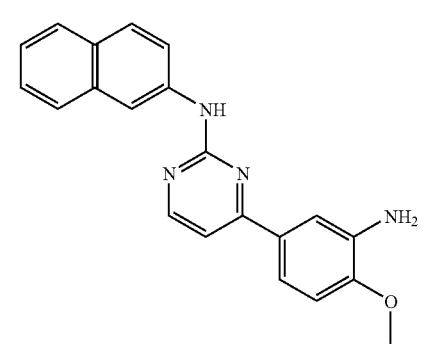
-continued
II-134
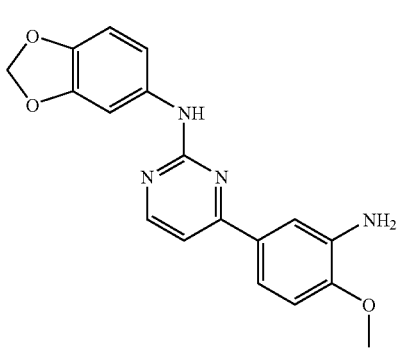
II-135
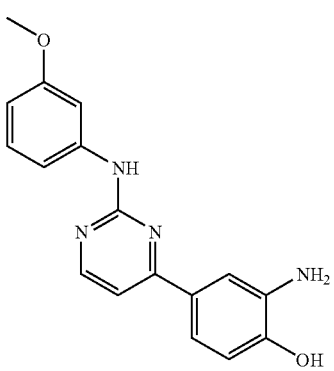
II-136
II-137
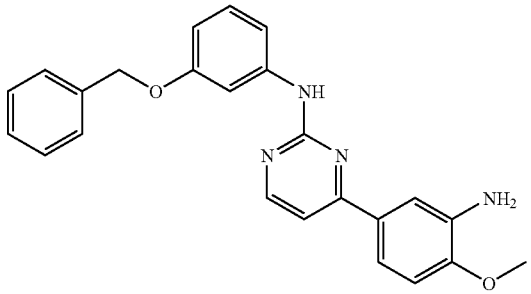

II-138
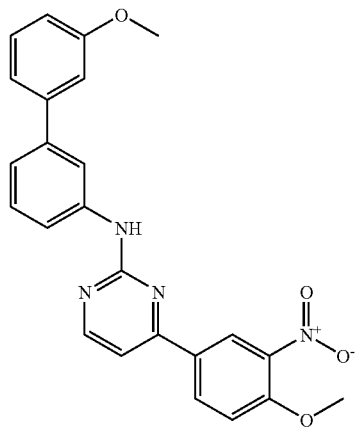
II-141
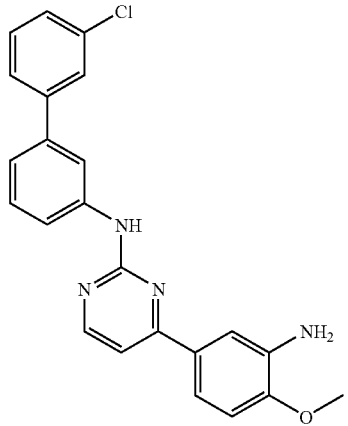
II-139
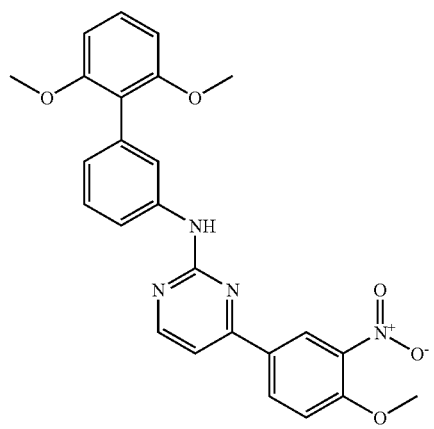
II-142
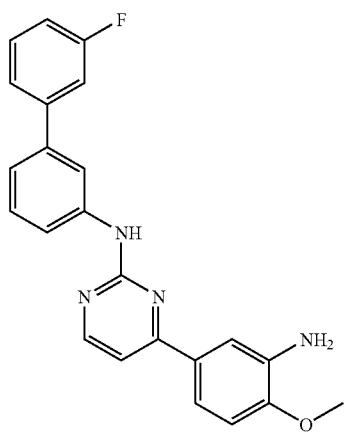
II-140
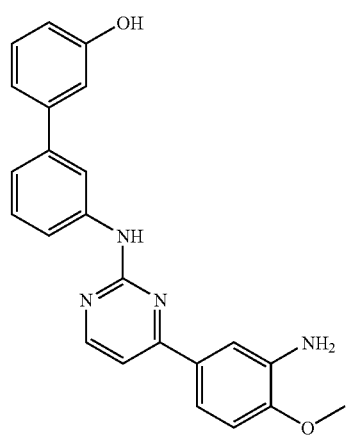
II-143
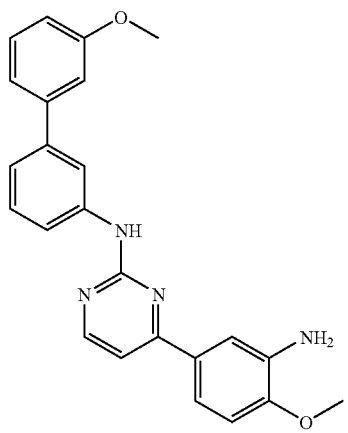

II-144
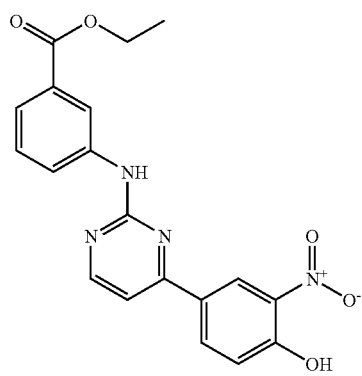
II-145
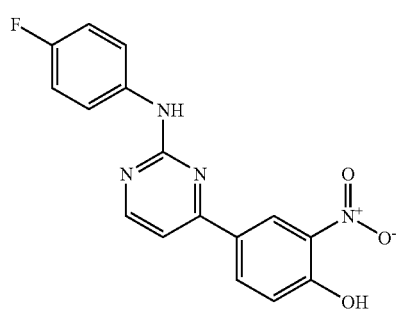
II-146
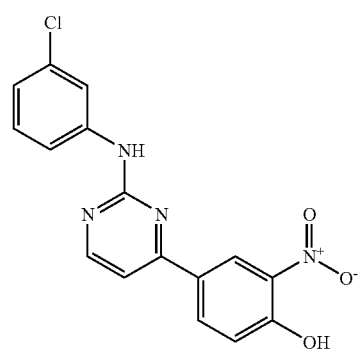
II-147
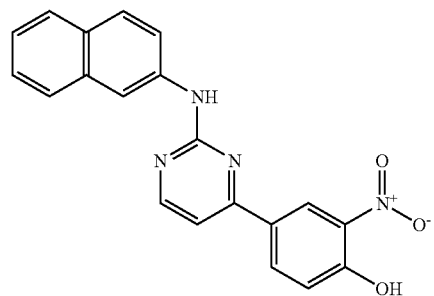
II-148
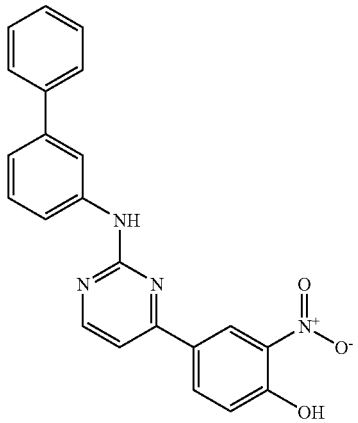
II-149
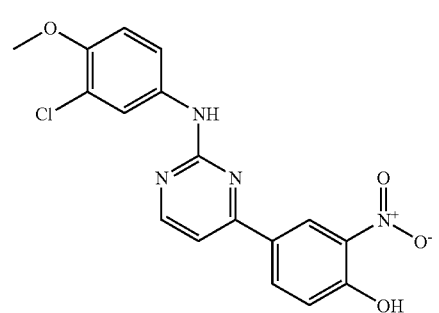
II-150
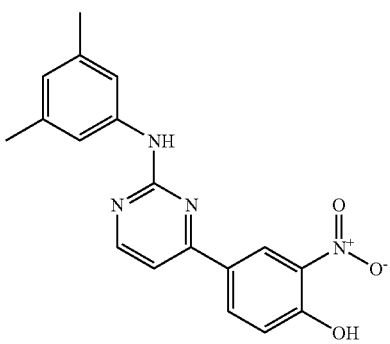

-continued

II-151
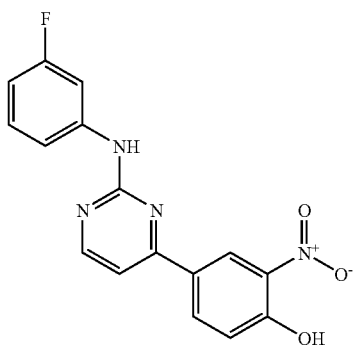

II-152
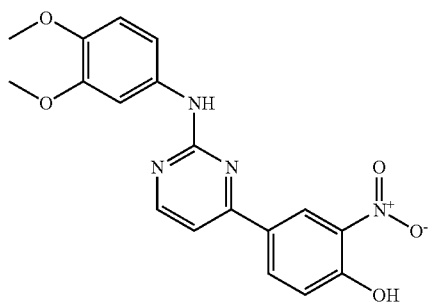

II-153
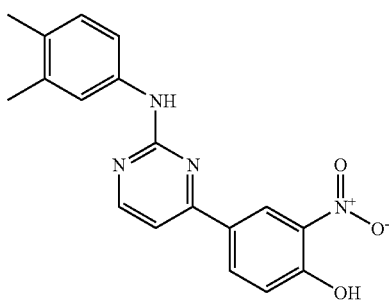

II-154
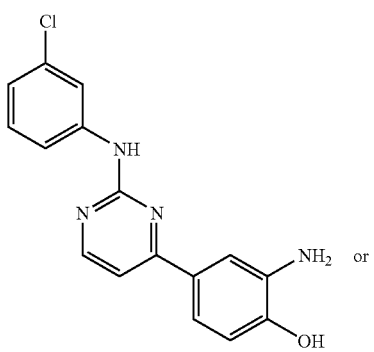

-continued

II-155
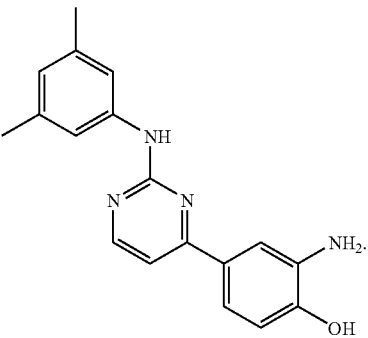

16. A pharmaceutical composition comprising a compound according to claim 1, and a pharmaceutically acceptable carrier, adjuvant, or vehicle.

17. The composition according to claim 16, further comprising an additional therapeutic agent selected from a chemotherapeutic or anti-proliferative agent, a treatment for Alzheimer's Disease, a treatment for Parkinson's Disease, an agent for treating Multiple Sclerosis (MS), a treatment for asthma, an agent for treating schizophrenia, an anti-inflammatory agent, an immunomodulatory or immunosuppressive agent, a neurotrophic factor, an agent for treating cardiovascular disease, an agent for treating destructive bone disorders, an agent for treating liver disease, an agent for treating a blood disorder, or an agent for treating an immunodeficiency disorder.

18. A method of treating or lessening the severity of a disease or disorder selected from allergic or type I hypersensitivity reaction, asthma, transplant rejection, rheumatoid arthritis or Familial amyotrophic lateral sclerosis (FALS), comprising administering to a subject in need thereof a compound of claim 1 or A composition of claim 16.

19. The method of claim 18, comprising the further step of administering to said patient an additional therapeutic agent selected from a treatment for Alzheimer's Disease, a treatment for asthma, an anti-inflammatory agent, or an immunomodulatory or immunosuppressive agent, wherein:

said additional therapeutic agent is appropriate for the disease being treated; and said additional therapeutic agent is administered together with said composition as a single dosage form or separately from said composition as part of a multiple dosage form.

* * * * *